US012643930B2

(12) United States Patent
Sahin et al.

(10) Patent No.: US 12,643,930 B2
(45) Date of Patent: Jun. 2, 2026

(54) IL2 AGONISTS

(71) Applicant: BioNTech SE, Mainz (DE)

(72) Inventors: Ugur Sahin, Mainz (DE); Sina Fellermeier-Kopf, Mainz (DE); Alexander Muik, Mainz (DE); Mathias Vormehr, Mainz (DE); Lena Mareen Kranz, Mainz (DE)

(73) Assignee: BioNTech SE, Mainz (DE)

( * ) Notice: Subject to any disclaimer, the term of this patent is extended or adjusted under 35 U.S.C. 154(b) by 1107 days.

(21) Appl. No.: 17/621,396

(22) PCT Filed: Jun. 23, 2020

(86) PCT No.: PCT/EP2020/067479
§ 371 (c)(1),
(2) Date: Dec. 21, 2021

(87) PCT Pub. No.: WO2020/260270
PCT Pub. Date: Dec. 30, 2020

(65) Prior Publication Data
US 2022/0356223 A1    Nov. 10, 2022

(30) Foreign Application Priority Data

Jun. 24, 2019    (WO) ................. PCT/EP2019/066648

(51) Int. Cl.
*C07K 14/55*    (2006.01)
*A61P 35/00*    (2006.01)
(52) U.S. Cl.
CPC .............. *C07K 14/55* (2013.01); *A61P 35/00* (2018.01); *C07K 2319/30* (2013.01); *C07K 2319/31* (2013.01)
(58) Field of Classification Search
None
See application file for complete search history.

(56) References Cited

FOREIGN PATENT DOCUMENTS

| CN | 106659757 | 5/2017 | |
| JP | 2014-502967 | 2/2014 | |
| JP | 2017-518361 | 7/2017 | |
| WO | 2012/088446 | 6/2012 | |
| WO | WO2015/164815 | 10/2015 | |
| WO | WO-2015164815 A1 * | 10/2015 | ............. A61K 38/00 |
| WO | 2018/091003 | 5/2018 | |
| WO | WO2020020783 | 1/2020 | |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*

Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Levin et al., "Exploiting a natural conformational switch to engineer an interleukin-2 'superkine'", Nature, vol. 484, No. 7395, Mar. 25, 2012, pp. 529-533.
Carmenate et al., "Human IL-2 mutein with higher antitumor efficacy than wild type IL-2", The Journal of Immunology, American Association of Immunologists, US, vol. 190, No. 12, Jun. 15, 2013, pp. 6230-6238.
Leon et al., "Combining computational and experimental biology to develop therapeutically valuable IL2 muteins", Seminars in Oncology, vol. 45, No. 1-2, Jan. 1, 2018, pp. 95-104.
International Preliminary Report On Patentability dated Dec. 28, 2021 for International Application No. PCT/EP2020/067479, 10 pages.
Thanos, C. D. et al. "Hot-spot mimicry of a cytokine receptor by a small molecule" PNAS (2006) vol. 103(42), pp. 15422-15427.
Mei, Longcan et al. "Site-Mutation of Hydrophobic core Residues Synchronically Poise Super Interleukin 2 for Signaling: Identifying Distant Structural Effects through Affordable Computations" International Journal of Molecular Sciences (2018) vol. 19(3) , pp. 1-23.
English Summary of Office Action for Japanese Patent Application No. JP2021-577041 dated Feb. 25, 2025, 2 pages.
Stauber, Deborah J. et al. "Crystal structure of the IL-2 signaling complex: paradigm for a heterotrimeric cytokine receptor" Proc Natl Acad Sci (2006) vol. 103(8), pp. 2788-2793.
Jarczak Dominik et al. "Cytokine Storm-Definition, Causes, and Implications" International Journal of Molecular Sciences (2022), vol. 23, p. 11740.
Baylot, Virginie et al. "TCTP has a crucial role in the different stages of prostate cancer malignant progression" Stem Cell to Disease, Results and Problems in Cell Differentiation 64 (2017), pp. 255-261.

(Continued)

*Primary Examiner* — Brian Gangle
*Assistant Examiner* — Andrea K Mccollum
(74) *Attorney, Agent, or Firm* — McDonnell, Boehnen, Hulbert & Berghoff, LLP

(57) ABSTRACT

The invention relates to variants of interleukin-2 (IL2). In particular, the invention relates to a polypeptide comprising a mutein of human IL2 or of a functional variant of human IL2, wherein the human IL2 or functional variant thereof is substituted such that affinity for the βγ IL2 receptor complex (IL2Rβγ) is enhanced. In one embodiment, the human IL2 or functional variant thereof is further substituted such that affinity for the αβγ IL2 receptor complex (IL2αβγ) is reduced. In one embodiment, the polypeptide activates effector T cells over regulatory T cells. The invention also relates to polynucleotides coding for the polypeptides of the invention, host cells comprising the polynucleotides, pharmaceutical compositions comprising the polypeptides, polynucleotides or host cells, therapeutic or prophylactic methods of treatment using the polypeptides, polynucleotides, host cells or pharmaceutical compositions and medical preparations comprising the polypeptides, polynucleotides, host cells or pharmaceutical compositions.

8 Claims, 29 Drawing Sheets

Specification includes a Sequence Listing.

(56)     References Cited

OTHER PUBLICATIONS

Colman P.M. "Effects of amino acid sequence changes on antibody-antigen interactions" Research in Immunology (1994), pp. 33-36.
Badri H. et al. "Optimization of radiation dosing schedules for proneural glioblastoma" J. Mathematical Biology (2016) vol. 72, pp. 1301-1336.
Klein, C., et al., 2017, "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines", Oncoimmunology, 6(3), pp. 1-15.

* cited by examiner

A

Human IL2Rα (CD25)

B

Human IL2Rβ (CD122)

A

B

A

A

B

A

| | Day | | |
|---|---|---|---|
| | 17 | 24 | 31 |
| hAlb-hIL2_A4s8 + gp70 vaccine | * | **** | **** |
| hAlb-hIL2_A4s8 | ns | ns | ns |
| gp70 vaccine | ns | ns | ns |
| hAlb + irr vaccine | | | |

B

| | Day | | |
|---|---|---|---|
| | 17 | 24 | 31 |
| hAlb-IL2_A4s8 + gp70 vaccine | **** | *** | * |
| hAlb-hIL2_A4s8 | **** | ns | ns |
| gp70 vaccine | ns | ns | ns |
| hAlb + irr vaccine | | | |

| | Day | | |
|---|---|---|---|
| | 17 | 24 | 31 |
| ◆ hAlb-hIL2_A4s8 + gp70 vaccine | ns | *** | ** |
| ◇ hAlb-hIL2_A4s8 | ns | ns | ** |
| ● gp70 vaccine | ns | ns | * |
| ○ hAlb + irr vaccine | | | |

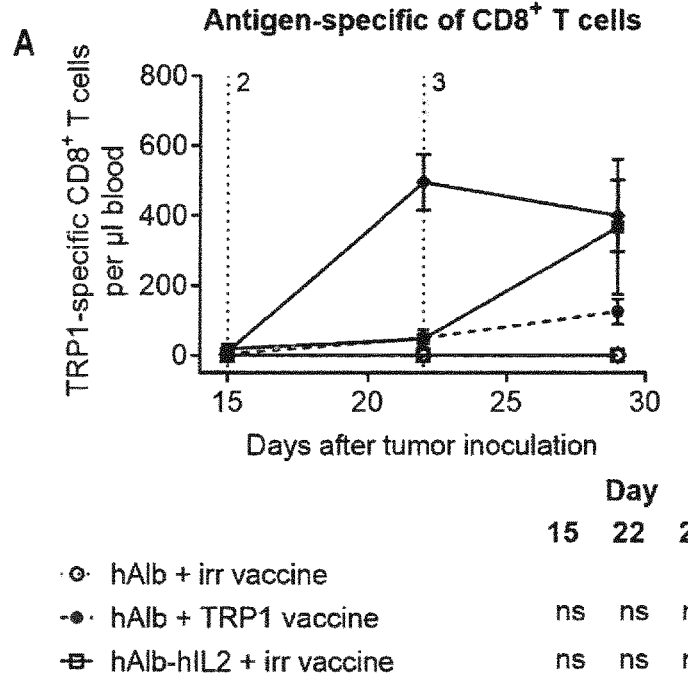

A

Antigen-specific of CD8⁺ T cells

|  | Day | | |
|---|---|---|---|
|  | 15 | 22 | 29 |
| ·o· hAlb + irr vaccine |  |  |  |
| ·●· hAlb + TRP1 vaccine | ns | ns | ns |
| -□- hAlb-hIL2 + irr vaccine | ns | ns | ns |
| -■- hAlb-hIL2 + TRP1 vaccine | ns | ns | **** |
| -◇- hAlb-hIL2_A4s8 + irr vaccine | ns | ns | ns |
| -◆- hAlb-hIL2_A4s8 + TRP1 vaccine | ns | **** | **** |

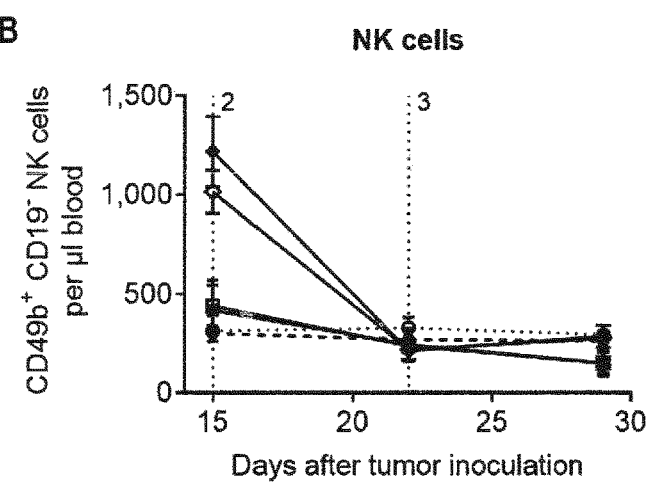

B

NK cells

|  | Day | | |
|---|---|---|---|
|  | 15 | 22 | 29 |
| ·o· hAlb + irr vaccine |  |  |  |
| ·●· hAlb + TRP1 vaccine | ns | ns | ns |
| -□- hAlb-hIL2 + irr vaccine | ns | ns | ns |
| -■- hAlb-hIL2 + TRP1 vaccine | ns | ns | ns |
| -◇- hAlb-hIL2_A4s8 + irr vaccine | **** | ns | ns |
| -◆- hAlb-hIL2_A4s8 + TRP1 vaccine | **** | ns | ns |

| | Day | | |
|---|---|---|---|
| | 15 | 22 | 29 |
| ·O· hAlb + irr vaccine | | | |
| -●· hAlb + TRP1 vaccine | ns | ns | ns |
| -⊟- hAlb-hIL2 + irr vaccine | **** | ns | ns |
| -■- hAlb-hIL2 + TRP1 vaccine | **** | ns | ns |
| -◇- hAlb-hIL2_A4s8 + irr vaccine | ns | ns | ns |
| -◆- hAlb-hIL2_A4s8 + TRP1 vaccine | ns | ns | ns |

- ·o·   hAlb + irr vaccine
- ·●·   hAlb + TRP1 vaccine   ns
- ·⊟·   hAlb-hIL2 + irr vaccine   ns
- ·■·   hAlb-hIL2 + TRP1 vaccine   ****
- ·◇·   hAlb-hIL2_A4s8 + irr vaccine   ns
- ·◆·   hAlb-hIL2_A4s8 + TRP1 vaccine   ****

A

Days after tumor incoulation

B

B

CD8⁺ T cells/Treg cells
7 days after 2nd treatment

Antigen-specific CD8⁺ T cells/Treg cells
7 days after 2nd treatment

IL2 AGONISTS

CROSS-REFERENCE TO RELATED APPLICATIONS

This application is a U.S. national phase of International Application No. PCT/EP2020/067479, filed Jun. 23, 2020, which claims priority from International Application No. PCT/EP2019/066648, filed Jun. 24, 2019, the disclosure of each of which is hereby incorporated by reference in its entirety.

TECHNICAL FIELD

The invention relates to variants of interleukin-2 (IL2). In particular, the invention relates to a polypeptide comprising a mutein of human IL2 or of a functional variant of human IL2, wherein the human IL2 or functional variant thereof is substituted such that affinity for the $\beta\gamma$ IL2 receptor complex (IL2R$\beta\gamma$) is enhanced. In one embodiment, the human IL2 or functional variant thereof is further substituted such that affinity for the $\alpha\beta\gamma$ IL2 receptor complex (IL2R$\alpha\beta\gamma$) is reduced. In one embodiment, the polypeptide activates effector T cells over regulatory T cells. The invention also relates to polynucleotides coding for the polypeptides of the invention, host cells comprising the polynucleotides, pharmaceutical compositions comprising the polypeptides, polynucleotides or host cells, therapeutic or prophylactic methods of treatment using the polypeptides, polynucleotides, host cells or pharmaceutical compositions and medical preparations comprising the polypeptides, polynucleotides, host cells or pharmaceutical compositions.

BACKGROUND

The immune system plays an important role in cancer, autoimmunity, allergy as well as in pathogen-associated diseases. T cells and natural killer (NK) cells are important mediators of anti-tumor immune responses. CD8$^+$ T cells and NK cells can directly lyse tumor cells. CD4$^+$ T cells, on the other hand, can mediate the influx of different immune subsets including CD8$^+$ T cells and NK cells into the tumor. CD4$^+$ T cells are able to license dendritic cells (DCs) for the priming of anti-tumor CD8$^+$ T cell responses and can act directly on tumor cells via IFN$\gamma$ mediated MHC upregulation and growth inhibition. CD8$^+$ as well as CD4$^+$ tumor specific T cell responses can be induced via vaccination or by adoptive transfer of T cells.

Cytokines play an important role in immunity. For example, interleukin-2 (IL2) is a potent immune stimulator, activating diverse cells of the immune system, including T cells, B cells, monocytes and NK cells. IL2 is known to support the differentiation, proliferation, survival and effector functions of T cells and NK cells (Blattman, J. N. et al. Nat. Med. 9, 540-7 (2003) and has been used for decades in the treatment of late stage malignant melanoma (Maas, R. A., Dullens, H. F. & Den Otter, W. Cancer Immunol. Immunother. 36, 141-8 (1993). Hence, immunotherapies such as T cell vaccines or adoptive transfer of (naïve or T cell receptor transgenic or chimeric antigen receptor trans-genic) T cells or NK cells can benefit from simultaneous administration of cytokines like IL2. One disadvantage of recombinant IL2, however, is its short plasma half-life creating the necessity to frequently inject high amounts of the cytokine. This leads to severe side effects such as vascular leak syndrome (VLS) (Rosenberg, S. A. et al. N. Engl. J. Med. 316, 889-97 (1987)). A second disadvantage of IL2 is its inherent ability to stimulate regulatory T cells (T$_{reg}$ cells). T$_{reg}$ cells are correlated with reduced survival of cancer patients as they can suppress the function of anti-tumor effector T cells and NK cells (Nishikawa, H. & Sakaguchi. Curr. Opin. Immunol. 27, 1-7 (2014)). T$_{reg}$ cell activation may exacerbate immune suppression, potentially compromising the intended therapeutic response. IL2 signals via the IL2 receptor which exists as a high- and an intermediate-affinity version. The high-affinity IL2 receptor (IL2R$\alpha\beta\gamma$) consists of CD25 (IL2R$\alpha$), CD122 (IL2R$\beta$) and CD132 (IL2R$\gamma$) and is expressed on T$_{reg}$ cells as well as activated CD4$^+$ and CD8$^+$ T cells. The intermediate-affinity receptor (IL2R$\beta\gamma$) lacks CD25 and is prevalent on naïve and memory T cells as well as NK cells. As a result, IL2 preferentially stimulates CD25 expressing T$_{reg}$ cells (Todd, J. A. et al. PLOS Med. 13, e1002139 (2016)) as well as activated CD4$^+$ and CD8$^+$ T cells and high doses of IL2 are needed to activate naïve and memory T cells and NK cells. Attempts to alter IL2 in such a way that it loses preference for CD25 expressing cells, thereby relatively increasing the stimulatory potential of naïve and memory T cells as well as NK cells was shown to improve its anti-tumoral potential (Arenas-Ramirez, N. et al. Sci. Transl. Med. 8, 1-13 (2016)).

There is a need for novel strategies to increase the effectiveness of IL2, in particular when used in the context of immunotherapy, in particular cancer immunotherapy, e.g., when used in combination with vaccines, in particular cancer vaccines, and other immunotherapies such as adoptive transfer of (naïve or T cell receptor transgenic or chimeric antigen receptor transgenic) T and NK cells, and/or checkpoint blockade.

Described herein are variants of human IL2 that preferentially activate cells which express the intermediate-affinity IL2 receptor IL2R$\beta\gamma$ in relation to cells which express the high-affinity IL2 receptor IL2R$\alpha\beta\gamma$. In particular, described herein are appropriate modifications of IL2 enhancing binding to (and thus activation of) cells expressing IL2R$\beta\gamma$. These modifications may be used in combination with modifications preventing effective binding to (and thus activation of) cells expressing IL2R$\alpha\beta\gamma$. An IL2 variant able to selectively activate the intermediate-affinity IL2 receptors on certain T cells such as memory T cells, naïve T cells and effector T cells as well as NK cells in preference to the high-affinity IL2 receptors on regulatory T cells is expected to have an improved therapeutic index over wild type IL2 and a reduced toxicity profile. An IL2 variant with an improved therapeutic index would have a significantly expanded range of use in the treatment of disorders requiring immune system stimulation, for example in the treatment of cancer (as a direct and/or adjunct therapy). In particular, administration of IL2 variant RNA is a promising approach to boost the therapeutic efficacy of multiple T and NK cell-based (cancer) immunotherapies.

The present disclosure provides novel IL2 variants. Specifically, variants of IL2 are described that contain mutations enhancing IL2R$\beta\gamma$ binding, in particular CD122 binding ("mut$\beta\gamma$") and optionally further contain mutations affecting IL2R$\alpha\beta\gamma$ binding, in particular CD25 binding ("mut$\alpha$"). In particular, variants of IL2 are described herein reducing expansion of T$_{reg}$ cells and increasing effector T-cell and NK-cell stimulation, preferably IL2R$\beta\gamma^+$ effector T-cell and NK-cell stimulation. The IL2 variant hAlb-hIL2_A4s8 described herein shows, compared to wild-type IL2, a markedly reduced capacity to activate T$_{reg}$ cells and increased ability to stimulate effector immune cells, preferably IL2R$\beta\gamma^+$ effector immune cells like CD8$^+$ T cells and NK cells already at lower concentrations. In vivo, treatment with nanoparticulate mRNA encoding wild-type IL2 or the selected IL2 variant with mutations affecting both IL2Rα binding and IL2Rβ binding (hAlb-hIL2_A4s8) targeted to the liver of mice for systemic availability strongly inhibited tumor growth, with hIL2_A4s8 being most effective. Whereas hAlb-hIL2 increases mainly antigen-specific T cells and $T_{reg}$ cells, hAlb-hIL2_A4s8 activates NK cells and elevates both antigen-specific and non-antigen-specific CD8$^+$ T-cell numbers without expanding $T_{reg}$ cells. Treatment with hAlb-hIL2_A4s8 strongly synergizes with RNA vaccination by expanding vaccine-induced CD8$^+$ T cell responses while avoiding stimulation and expansion of $T_{reg}$ cells, and augments the anti-tumoral efficacy of PD-L1 immune checkpoint blockade by specifically expanding pre-existing antigen-specific CD8$^+$ T cells.

SUMMARY

In a first aspect, provided herein is a polypeptide comprising a mutein of human interleukin-2 (IL2) or of a functional variant of human IL2, wherein the human IL2 or the functional variant thereof is substituted at at least position 80 (leucine), position 81 (arginine), position 85 (leucine) and position 92 (isoleucine) relative to wild type human IL2 and numbered in accordance with wild type human IL2, wherein the substitution enhances the affinity for the βγ IL2 receptor complex (IL2Rβγ) and wherein the human IL2 or the functional variant thereof is not substituted at position 86 (isoleucine) relative to wild type human IL2 and numbered in accordance with wild type human IL2.

In one embodiment, position 80 (leucine) is substituted by phenylalanine, position 81 (arginine) is substituted by glutamic acid, position 85 (leucine) is substituted by valine and position 92 (isoleucine) is substituted by phenylalanine relative to wild type human IL2 and numbered in accordance with wild type human IL2.

In one embodiment, the human IL2 or the functional variant thereof is further substituted at position 74 (glutamine) relative to wild type human IL2 and numbered in accordance with wild type human IL2. In one embodiment, position 74 (glutamine) is substituted by histidine relative to wild type human IL2 and numbered in accordance with wild type human IL2.

In a second aspect, provided herein is a polypeptide comprising a mutein of human IL2 or of a functional variant of human IL2, wherein the human IL2 or the functional variant thereof is substituted at at least position 80 (leucine) by phenylalanine, position 81 (arginine) by glutamic acid, position 85 (leucine) by valine and position 92 (isoleucine) by phenylalanine relative to wild type human IL2 and numbered in accordance with wild type human IL2.

In one embodiment, the human IL2 or the functional variant thereof is further substituted at position 74 (glutamine) by histidine relative to wild type human IL2 and numbered in accordance with wild type human IL2.

In a third aspect, provided herein is a polypeptide comprising a mutein of human IL2 or of a functional variant of human IL2, wherein the human IL2 or the functional variant thereof is substituted at at least position 74 (glutamine) by histidine, position 80 (leucine) by phenylalanine, position 81 (arginine) by glutamic acid, position 85 (leucine) by valine and position 92 (isoleucine) by phenylalanine relative to wild type human IL2 and numbered in accordance with wild type human IL2.

In one embodiment of the second and third aspect, the substitution enhances the affinity for IL2Rβγ.

In one embodiment, the substituted IL2 or functional variant thereof (IL2 mutein) described above has an amino acid sequence identical to wild type IL2 at the other, non-substituted residues. In one embodiment, the IL2 mutein described above has amino acid modifications such as amino acid substitutions at one or more sites in or at the other residues of wild type human IL2. In one embodiment, such amino acid substitutions result in relatively decreased affinity for IL2Rαβγ when compared to wild type IL2 (also termed "mutα" mutations herein). In one embodiment, such amino acid substitutions are at amino acid residues that contact IL2Rα.

Thus, in one embodiment, the human IL2 or the functional variant thereof further comprises one or more amino acid substitutions which reduce the affinity for the alpha subunit of the αβγ IL2 receptor complex (IL2Rαβγ).

In one embodiment, the one or more amino acid substitutions which reduce the affinity for the alpha subunit of IL2Rαβγ reduce the affinity for IL2Rαβγ to a greater extent than for IL2Rβγ.

In one embodiment, the one or more amino acid substitutions which reduce the affinity for the alpha subunit of IL2Rαβγ comprise substitutions of the human IL2 or the functional variant thereof at at least one of positions 35 (lysine), 43 (lysine), 61 (glutamic acid) and 62 (glutamic acid) relative to wild type human IL2 and numbered in accordance with wild type human IL2. In one embodiment, if the amino acid residue is an acidic amino acid residue in wild type human IL2 the substitution is by a basic amino acid residue and if the amino acid residue is a basic amino acid residue in wild type human IL2 the substitution is by an acidic amino acid residue.

In different embodiments, the one or more amino acid substitutions which reduce the affinity for the alpha subunit of IL2Rαβγ comprise substitutions of the human IL2 or the functional variant thereof at at least the following positions relative to wild type human IL2 and numbered in accordance with wild type human IL2:

position 35,
    position 43,
    position 61,
    position 62,
    position 35 and position 43,
    position 35 and position 61,
    position 35 and position 62,
    position 43 and position 61,
    position 43 and position 62,
    position 61 and position 62,
    position 35, position 43 and position 61,
    position 35, position 43 and position 62,
    position 35, position 61 and position 62,
    position 43, position 61 and position 62, or
    position 35, position 43, position 61 and position 62.

In one embodiment, position 35 is substituted with glutamic acid. In one embodiment, position 43 is substituted with glutamic acid. In one embodiment, position 61 is substituted with lysine. In one embodiment, position 62 is substituted with lysine.

In one embodiment, position 35 is substituted. In one embodiment, position 35 is substituted with glutamic acid.

In one embodiment, position 43 is substituted. In one embodiment, position 43 is substituted with glutamic acid.

In one embodiment, position 61 is substituted. In one embodiment, position 61 is substituted with lysine.

In one embodiment, position 62 is substituted. In one embodiment, position 62 is substituted with lysine.

In one embodiment, positions 43 and 61 are substituted. In one embodiment, position 43 is substituted with glutamic acid and position 61 is substituted with lysine.

In one embodiment, positions 35, 43 and 61 are substituted. In one embodiment, position 35 is substituted with glutamic acid, position 43 is substituted with glutamic acid and position 61 is substituted with lysine.

In one embodiment, positions 61 and 62 are substituted. In one embodiment, position 61 is substituted with lysine and position 62 is substituted with lysine.

In one embodiment, the one or more amino acid substitutions which reduce the affinity for the alpha subunit of IL2Rαβγ comprise substitutions of the human IL2 or the functional variant thereof at position 43 (lysine) and position 61 (glutamic acid) relative to wild type human IL2 and numbered in accordance with wild type human IL2. In one embodiment, position 43 (lysine) is substituted by glutamic acid and position 61 (glutamic acid) is substituted by lysine.

In a fourth aspect, provided herein is a polypeptide comprising a mutein of human IL2 or of a functional variant of human IL2, wherein the human IL2 or the functional variant thereof is substituted at at least position 43 (lysine) by glutamic acid, position 61 (glutamic acid) by lysine, position 74 (glutamine) by histidine, position 80 (leucine) by phenylalanine, position 81 (arginine) by glutamic acid, position 85 (leucine) by valine and position 92 (isoleucine) by phenylalanine relative to wild type human IL2 and numbered in accordance with wild type human IL2.

In one embodiment of the second to fourth aspects, the human IL2 or the functional variant thereof is not substituted at position 86 (isoleucine) relative to wild type human IL2 and numbered in accordance with wild type human IL2.

In one embodiment, the human IL2 has the amino acid sequence according to SEQ ID NO: 1.

In one embodiment, the mutein of human IL2 or the functional variant thereof has a decreased ability to stimulate regulatory T cells compared to wild type human IL2.

In one embodiment, the mutein of human IL2 or the functional variant thereof has an increased ability to stimulate effector T cells compared to wild type human IL2.

The IL2 mutein described herein may be attached to a pharmacokinetic modifying group and, thus, may be an "extended-pharmacokinetic (PK) IL2".

In one embodiment, the polypeptide described herein is an extended pharmacokinetic (PK) polypeptide. In one embodiment, the extended-PK polypeptide comprises a fusion protein. In one embodiment, the fusion protein comprises a moiety of the mutein of human IL2 or the functional variant thereof and a moiety which is heterologous to human IL2 or the functional variant thereof. In one embodiment, the fusion protein comprises a moiety of the mutein of human IL2 or the functional variant thereof and a moiety selected from the group consisting of serum albumin, an immunoglobulin fragment, transferrin, Fn3, and variants thereof. In one embodiment, the serum albumin comprises mouse serum albumin or human serum albumin. In one embodiment, the immunoglobulin fragment comprises an immunoglobulin Fc domain.

In one aspect, provided herein is a polypeptide comprising an amino acid sequence selected from the group consisting of SEQ ID NOs: 2, 11, 13, and 22, such as SEQ ID NO: 2, SEQ ID NO: 11, SEQ ID NO: 13 or SEQ ID NO: 22 of the sequence listing.

The above described polypeptides are also termed "IL2 variant polypeptide" or simply "IL2 variant" herein.

In one aspect, provided herein is a polynucleotide encoding the polypeptide described herein. In one embodiment, the polynucleotide is RNA.

In one aspect, provided herein is a host cell comprising the polynucleotide described herein.

In one aspect, provided herein is the polypeptide described herein, the polynucleotide described herein, or the host cell described herein for pharmaceutical use. In one embodiment, the pharmaceutical use comprises a therapeutic or prophylactic treatment of a disease or disorder.

In one aspect, provided herein is the polypeptide described herein, the polynucleotide described herein, or the host cell described herein for use in a method for treating or preventing cancer in a subject.

In one aspect, provided herein is a pharmaceutical composition comprising the polypeptide described herein, the polynucleotide described herein, or the host cell described herein.

In one aspect, provided herein is a method of treating a subject comprising administering to the subject the polypeptide described herein, the polynucleotide described herein, the host cell described herein, or the pharmaceutical composition described herein.

In one aspect, provided herein is a method for inducing an immune response in a subject comprising administering to the subject the polypeptide described herein, the polynucleotide described herein, the host cell described herein, or the pharmaceutical composition described herein.

In one embodiment, the subject is further treated using one or more immunotherapies, e.g., using vaccination or adoptive transfer of T cells, such as T cell vaccines or adoptive transfer of (naïve or T cell receptor transgenic or chimeric antigen receptor transgenic) T cells or NK cells.

The effectiveness of vaccines, wherein the antigen is either delivered per se or as a polynucleotide, in particular as RNA encoding the antigen (e.g. RNA encoding a peptide or protein used for vaccination also referred to as "peptide or protein comprising an epitope for inducing an immune response against an antigen", "vaccine antigen" or simply "antigen" herein) can be increased by co-administering IL2 variant polypeptides described herein, wherein the IL2 variant polypeptide is either delivered per se or as a polynucleotide, in particular RNA encoding the IL2 variant polypeptide. The vaccine is particularly effective if the RNA encoding the IL2 variant polypeptide is targeted to the liver for systemic availability. Liver cells can be efficiently transfected and are able to produce large amounts of protein. Antigen-encoding RNA is preferably targeted to secondary lymphoid organs. Furthermore, the vaccine is particularly effective if an immune checkpoint inhibitor such as an anti-PD-L1 antibody is further administered.

In one embodiment, the method described herein further comprises administering to the subject a peptide or protein comprising an epitope for inducing an immune response specific for an antigen in the subject or a polynucleotide encoding the peptide or protein. In one embodiment, the polynucleotide encoding the peptide or protein is RNA.

In one embodiment, the method described herein is a method for treating or preventing cancer in a subject, wherein optionally the antigen is a tumor-associated antigen.

In one aspect, provided herein is a method for treating or preventing cancer in a subject comprising administering to the subject the polypeptide described herein, the polynucleotide described herein, the host cell described herein, or the pharmaceutical composition described herein.

In one embodiment, the method further comprises administering to the subject a peptide or protein comprising an epitope for inducing an immune response specific for a tumor-associated antigen in the subject or a polynucleotide encoding the peptide or protein. In one embodiment, the polynucleotide encoding the peptide or protein is RNA.

In one embodiment, the methods described herein comprise administering to a subject:

a. RNA encoding the IL2 variant polypeptide described herein; and b. RNA encoding a peptide or protein comprising an epitope for inducing an immune response specific for an antigen in the subject.

In one embodiment, the cancer is selected from the group consisting of melanoma, leukemia, lymphoma, lung cancer, breast cancer, prostate cancer, ovarian cancer, colon cancer, mesothelioma, renal cell carcinoma, and brain cancer.

In one embodiment, the methods described herein further comprise administering to the subject an immune checkpoint inhibitor. In one embodiment, the immune checkpoint inhibitor targets the interaction between (i) PD-1 and PD-L1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

In one embodiment, the RNA encoding the IL2 variant polypeptide described herein, the RNA encoding a peptide or protein comprising an epitope for inducing an immune response against an antigen in the subject, and optionally the immune checkpoint inhibitor are administered simultaneously or sequentially.

In one aspect, provided herein is a medical preparation comprising the polypeptide described herein, the polynucleotide described herein, the host cell described herein, or the pharmaceutical composition described herein.

In one embodiment, the medical preparation further comprises a peptide or protein comprising an epitope for inducing an immune response specific for an antigen in a subject or a polynucleotide encoding the peptide or protein. In one embodiment, the polynucleotide encoding the peptide or protein is RNA.

In one embodiment, the medical preparation comprises the polypeptide, polynucleotide, host cell, or pharmaceutical composition and the peptide or protein comprising an epitope or polynucleotide encoding the peptide or protein, respectively, in separate containers.

In one embodiment, the medical preparation comprises:

a. RNA encoding the IL2 variant polypeptide described herein; and b. RNA encoding a peptide or protein comprising an epitope for inducing an immune response specific for an antigen in a subject.

In one embodiment of the medical preparation, the RNA is present in a form selected from a liquid form, a solid form, or a combination thereof. In one embodiment, the solid form is a frozen form or a dehydrated form. In one embodiment, the dehydrated form is a freeze-dried or spray-dried form.

In one embodiment, the medical preparation further comprises an immune checkpoint inhibitor. In one embodiment, the immune checkpoint inhibitor targets the interaction between (i) PD-1 and PD-L1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

In one embodiment, the medical preparation is a kit. In one embodiment, the medical preparation comprises each component a. and b. in a separate container.

In one embodiment, the medical preparation is a pharmaceutical composition. In one embodiment, the pharmaceutical composition further comprises one or more pharmaceutically acceptable carriers, diluents and/or excipients.

In one embodiment, the medical preparation further comprises instructions for use of the medical preparation for treating or preventing cancer wherein optionally the antigen is a tumor-associated antigen.

In one aspect, provided herein is the medical preparation described herein for pharmaceutical use. In one embodiment, the pharmaceutical use comprises a therapeutic or prophylactic treatment of a disease or disorder.

In one aspect, provided herein is the medical preparation described herein for use in a method for treating or preventing cancer in a subject, wherein optionally the antigen is a tumor-associated antigen.

In one embodiment, the cancer is selected from the group consisting of melanoma, leukemia, lymphoma, lung cancer, breast cancer, prostate cancer, ovarian cancer, colon cancer, mesothelioma, renal cell carcinoma, and brain cancer.

In a further aspect, the invention relates to the IL2 variant polypeptide described herein, the polynucleotide encoding the IL2 variant polypeptide described herein, the host cell comprising the polynucleotide encoding the IL2 variant polypeptide described herein, or the pharmaceutical composition described herein for use in a method described herein.

Dose-response curves of STAT5 phosphorylation (pSTAT5) of $CD4^+CD25^+$ $T_{reg}$ cells (A), $CD8^+$ cytotoxic T cells (B) as well as CD56+NK cells (C). Human PBMCs were incubated with serial dilutions of hAlb-hIL2_A4 variant-containing supernatant and phosphorylation of STAT5 was subsequently analyzed in different lymphocyte subsets via flow cytometry. Supernatants of HEK293T/17 cells lipofected with mRNA encoding for hAlb only were used as negative control. Data shown are single values of one representative experiment fitted with a four parameter logarithmic fit to calculate $EC_{50}$ values.

Figure 2:
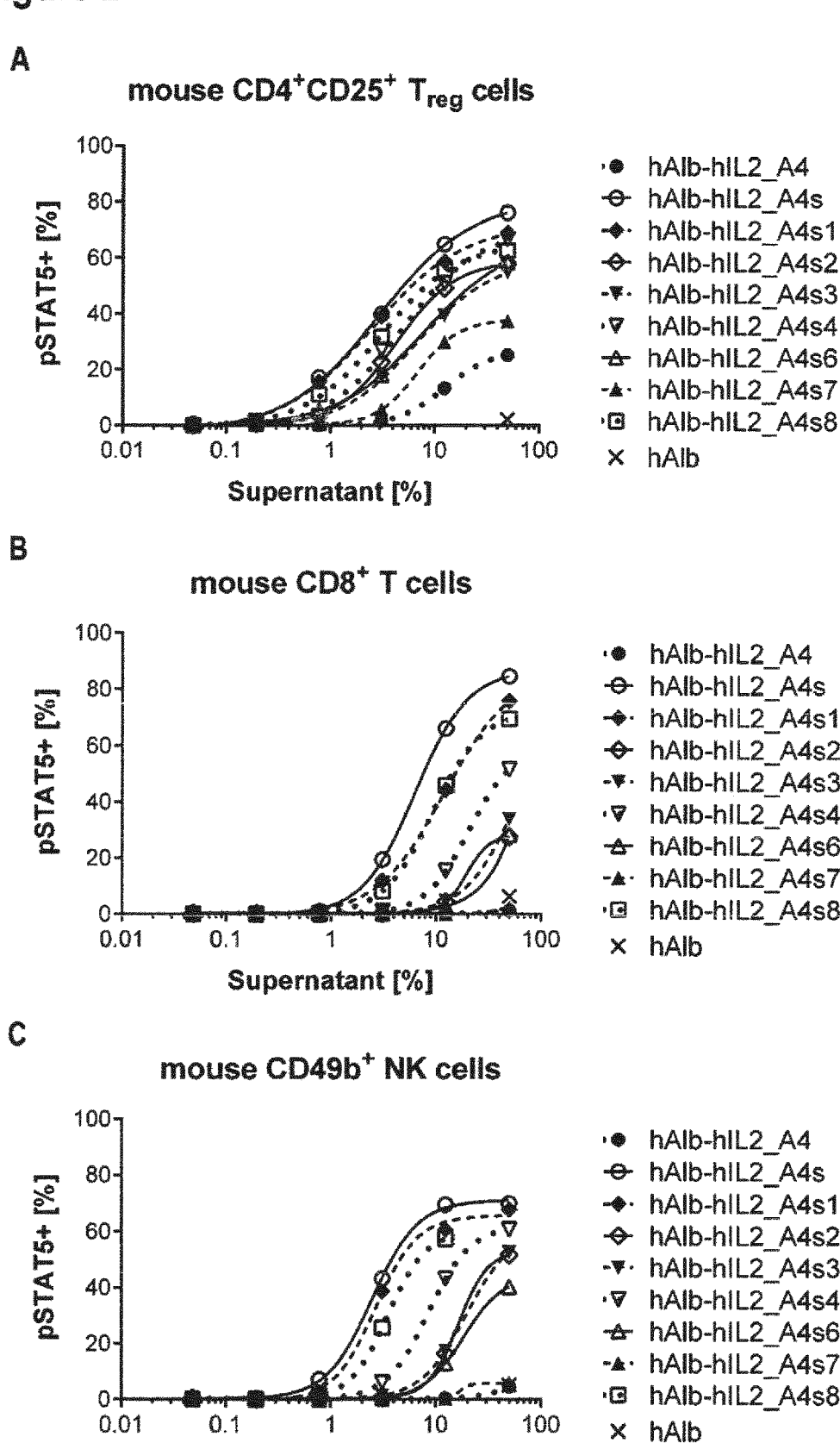

FIG. 2: Functional activity of hAlb-hIL2_A4 variants on different lymphocyte subsets in mouse splenocytes measured by IL2-mediated phosphorylation of STAT5.

Dose-response curves of STAT5 phosphorylation (pSTAT5) of $CD4^+CD25^+$ $T_{reg}$ cells (A), $CD8^+$ cytotoxic T cells (B) as well as NK cells (C). Balb/c splenocytes were incubated with serial dilutions of hAlb-hIL2_A4 variant-containing supernatant and phosphorylation of STAT5 was subsequently analyzed in different lymphocyte subsets via flow cytometry. Supernatants of HEK293T/17 cells lipofected with mRNA encoding for hAlb only were used as negative control. Data shown are single values of one representative experiment fitted with a four parameter logarithmic fit to calculate $EC_{50}$ values.

Figure 3:
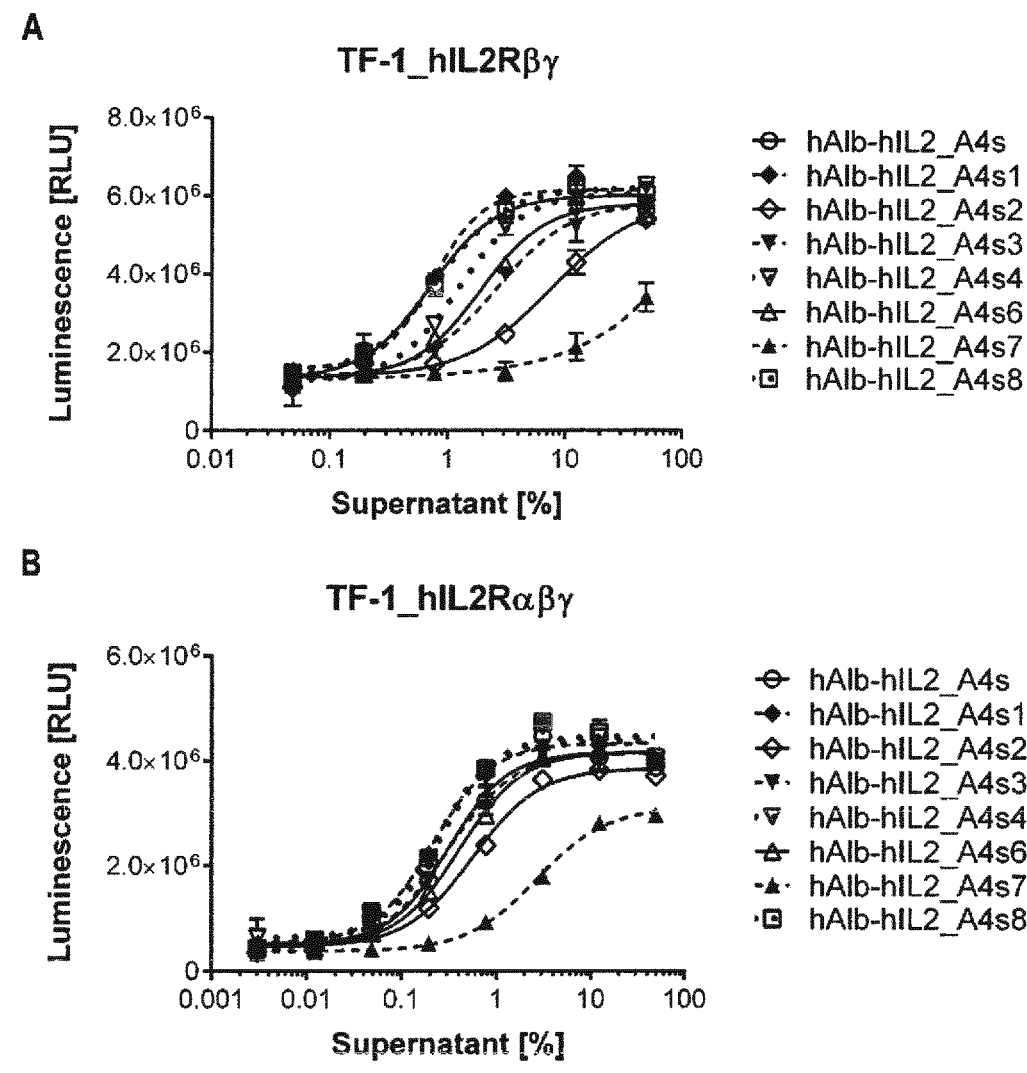

FIG. 3: Relative bioactivity of hAlb-hIL2_A4 variants in intermediate-affinity IL2 receptor (IL2Rβγ) and high-affinity IL2 receptor (IL2Rαβγ) dependent cell culture.

Proliferation responses of the intermediate-affinity IL2 receptor (IL2Rβγ) expressing human cell line TF-1_hIL2Rβγ (A) and the high-affinity IL2 receptor (IL2Rαβγ)-expressing human cell line TF-1_hIL2Rαβγ (B) are shown. Cell cultures were incubated for three days with serial dilutions of hAlb-hIL2_A4 variant-containing supernatants and proliferation was measured by quantitating viable cells via ATP amount using the CellTiter-Glo® 2.0 Assay. Data shown are mean±SD of n=2 technical replicates fitted with a four parameter logarithmic fit to calculate $EC_{50}$ values. RLU=relative luminescence units.

Figure 4:
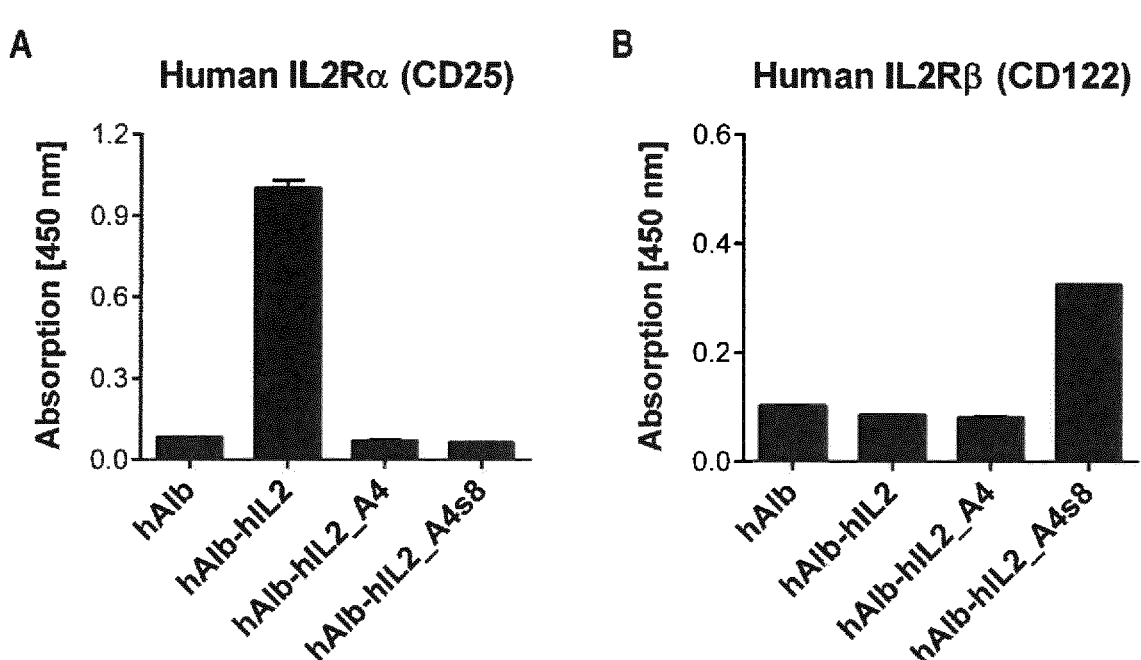

FIG. 4: Binding of human IL2Rα (CD25) and human IL2Rβ (CD122) by hAlb-hIL2_A4s8 in comparison to hAlb-hIL2_A4 and hAlb-hIL2.

100 ng plate-bound recombinant human CD25-Fc (A) or human CD122-Fc (B) was incubated with 1:2 diluted hAlb-hIL2 variant-containing supernatants and bound protein was detected via an HRP-conjugated anti-human Serum Albumin antibody. Supernatants of HEK293T/17 cells lipofected with mRNA encoding for hAlb only were used as negative control. Data shown are mean±SD of n=2 technical replicates.

Figure 5:
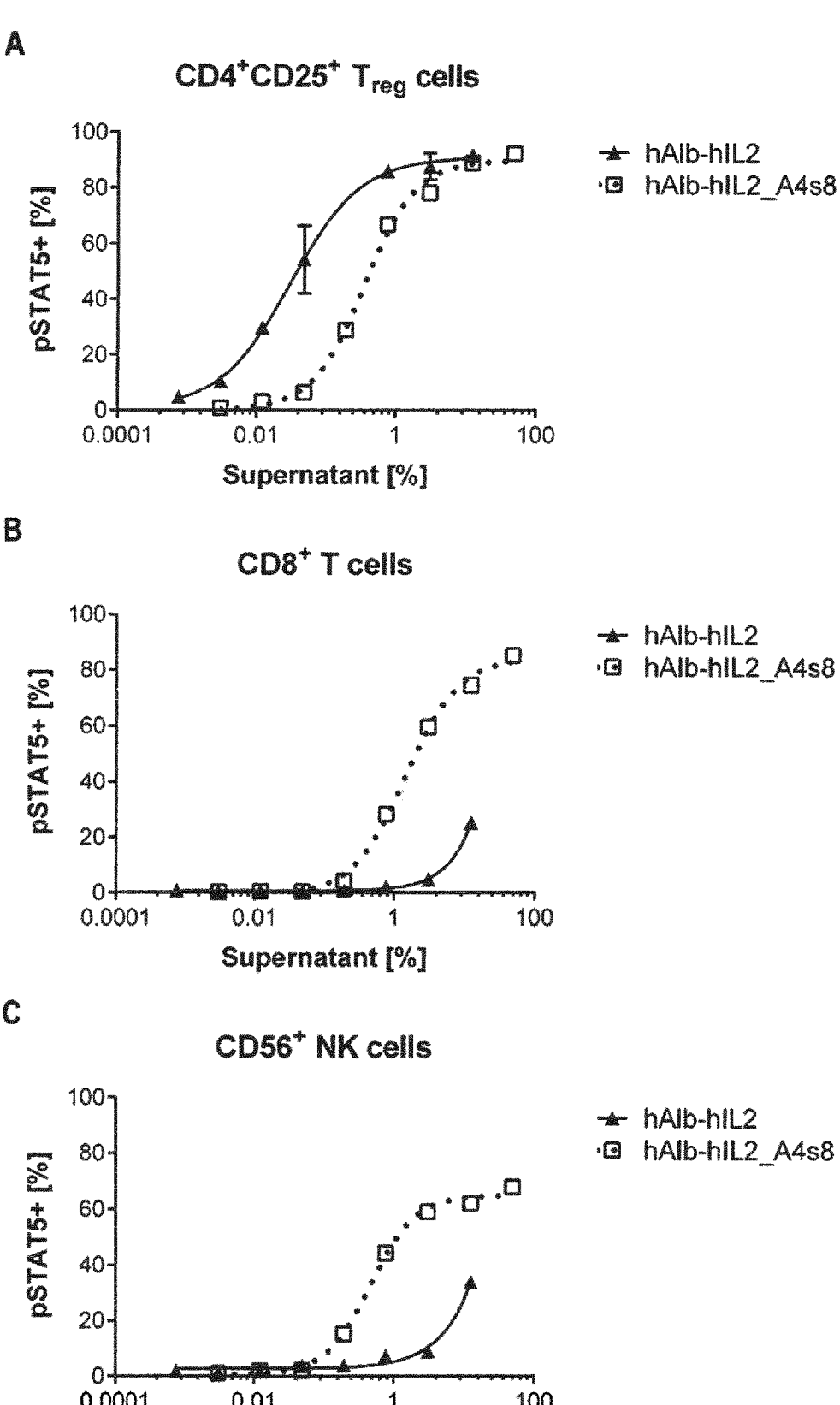

FIG. 5: Comparison of hAlb-hIL2_A4s8 with hAlb-hIL2 regarding functional activity on different immune cell subsets in human PBMCs measured by IL2-mediated phosphorylation of STAT5.

Dose-response curves of STAT5 phosphorylation (pSTAT5) of $CD4^+CD25^+$ $T_{reg}$ cells (A), $CD8^+$ cytotoxic T cells (B) and $CD56^+$ NK cells (C). Human PBMCs were incubated with serial dilutions of hAlb-hIL2 variant-containing supernatant and phosphorylation of STAT5 was subsequently analyzed in different lymphocyte subsets via flow cytometry. Data shown are mean±SD of n=2 technical replicates fitted with a four parameter logarithmic fit to calculate $EC_{50}$ values.

Figure 6:
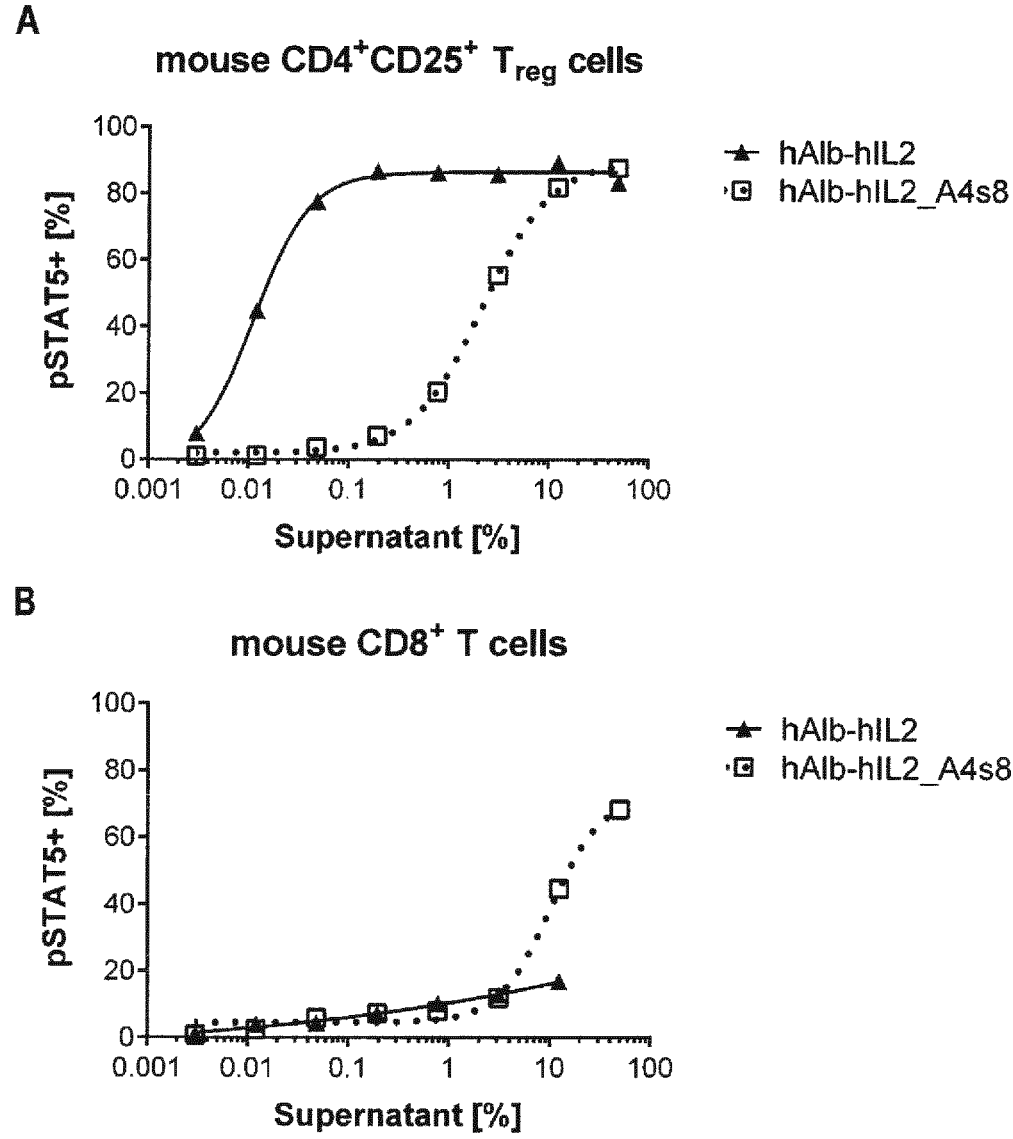

FIG. 6: Functional activity of hAlb-hIL2_A4s8 in comparison to hAlb-hIL2 on different T-cell subsets in mouse PBMCs measured by IL2-mediated phosphorylation of STAT5.

Dose-response curves of STAT5 phosphorylation (pSTAT5) of $CD4^+CD25^+$ $T_{reg}$ cells (A), and $CD8^+$ cytotoxic T cells (B). PBMCs isolated from whole blood of Balb/c mice were incubated with serial dilutions of hAlb-hIL2 variant-containing supernatants and phosphorylation of STAT5 was subsequently analyzed in different T-cell subsets via flow cytometry. Data shown are single values of one representative experiment fitted with a four parameter logarithmic fit to calculate $EC_{50}$ values.

Figure 7:
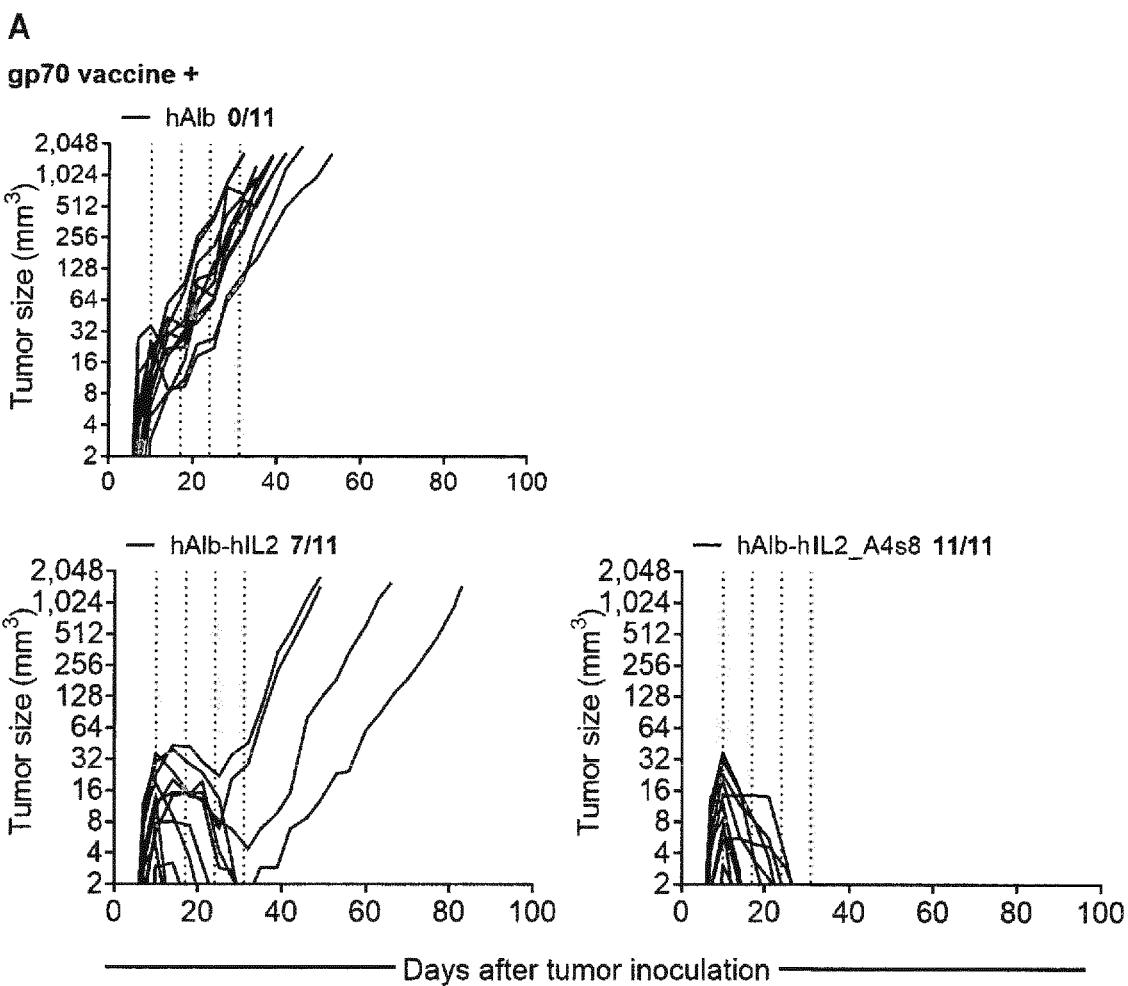
Figure 7:
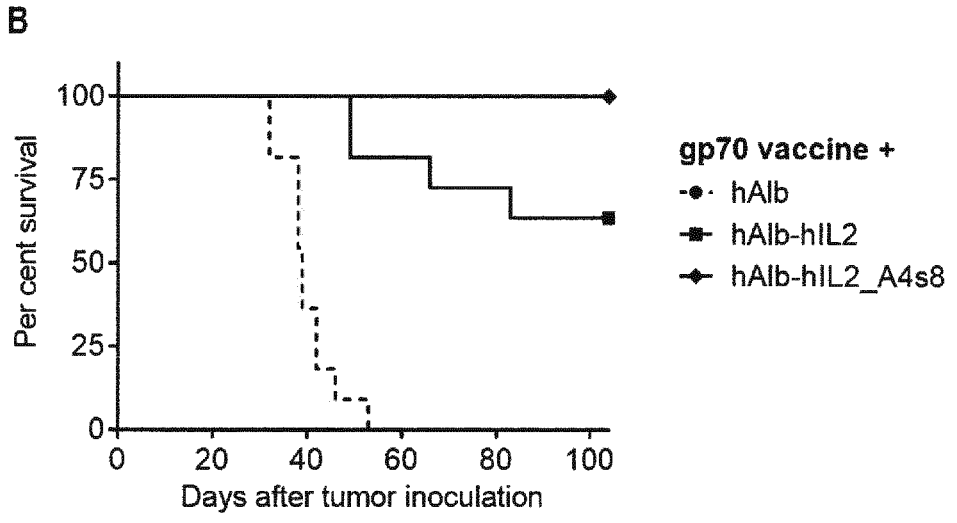

FIG. 7: Reduced tumor growth resulting in improved survival upon treatment with hAlb-hIL2_A4s8 compared to hAlb-hIL2 in combination with a therapeutic RNA vaccine in the murine colon carcinoma model CT26.

BALB/c mice (n=11 per group) were inoculated with $5\times10^5$ CT26 tumor cells subcutaneously (s.c.) and vaccinated intravenously (i.v.) four times weekly (day 10, 17, 24 and 31) with 20 µg RNA-LPX encoding the $CD8^+$ T-cell antigen gp70. RNAs coding for hAlb-hIL2_A4s8 or hAlb-hIL2 (3 µg each) and formulated as LNPs were administered i.v. concomitantly with the RNA vaccine. The control group received RNA vaccine with hAlb (not coding for any cytokine) formulated as LNPs. (A) Tumor growth of individual mice and (B) survival of mice treated with hAlb-hIL2 or hAlb-hIL2_A4s8 in combination with gp70 vaccine. Dotted lines indicate treatment days. Ratios in (A) represent the number of tumor-free mice over the total number of mice per group.

Figure 8:
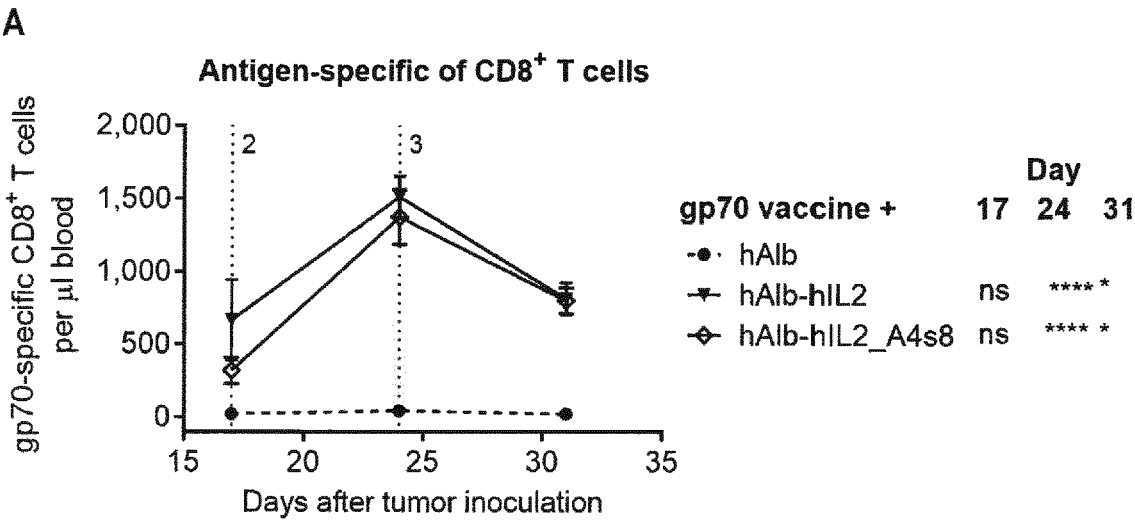
Figure 8:
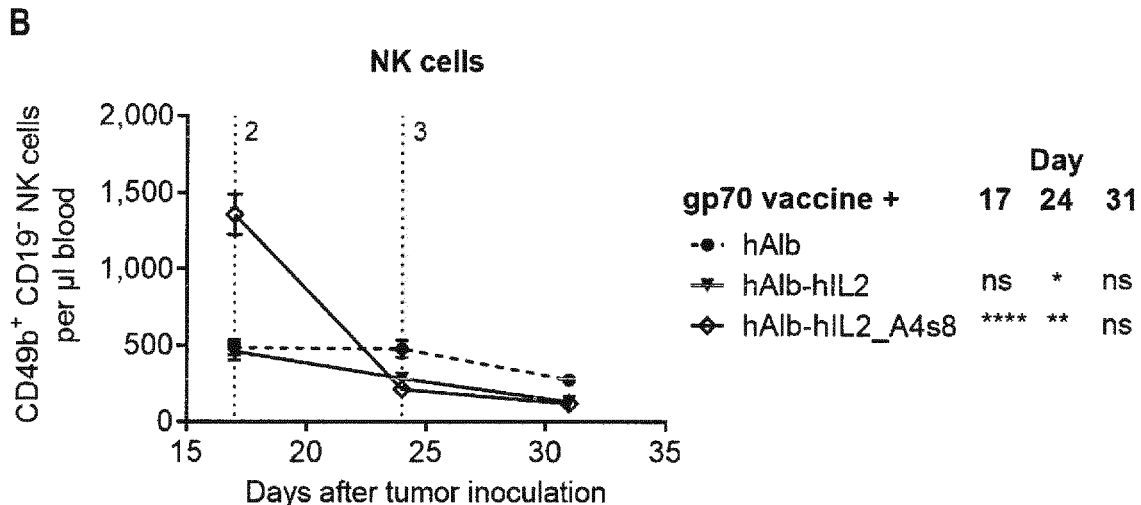

FIG. 8: Expansion of tumor antigen-specific $CD8^+$ T cells and NK cells upon treatment with hAlb-hIL2_A4s8 compared to hAlb-hIL2 in combination with a therapeutic RNA vaccine in the murine colon carcinoma model CT26.

(A) Absolute numbers of gp70-specific T cells and (B) NK cells per µL blood determined seven days after the first three treatments (day 17, 24 and 31) via flow cytometry from BALB/c mice described in Example 6 and FIG. 7. Dotted lines indicate treatment days, numbers at dotted lines indicate number of treatments. Mean±SEM. Statistical significance was determined using two-way ANOVA followed by Dunnett's multiple comparisons test. All analyses were two-tailed and carried out using GraphPad Prism 8. ns $P>0.05$, *$P<0.05$, $P<0.01$, *$P<0.001$, ****$P<0.0001$.

Figure 9:
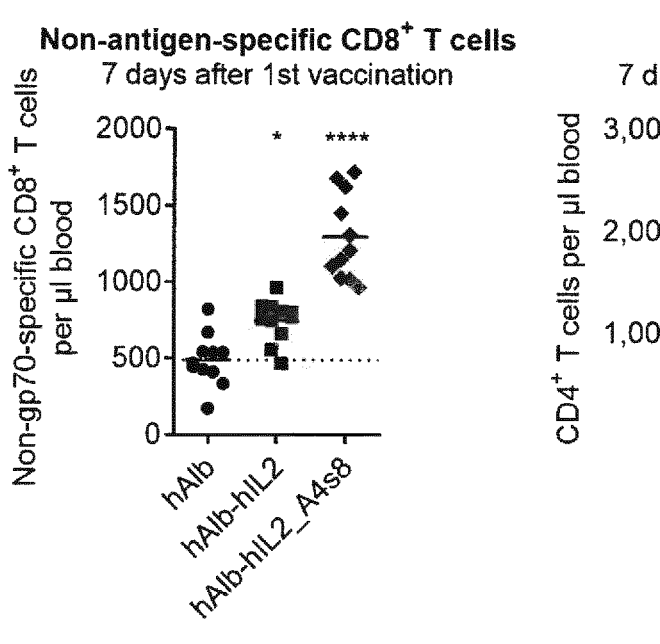
Figure 9:
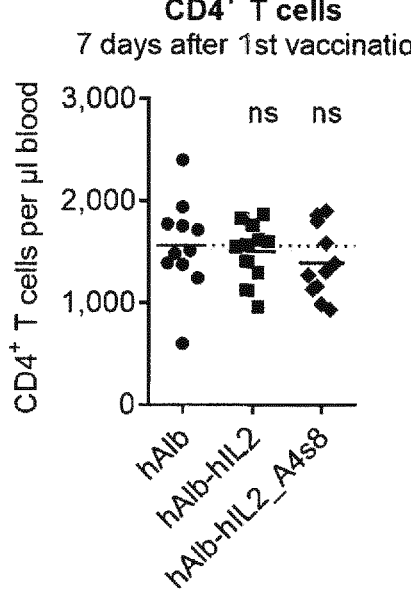
Figure 9:
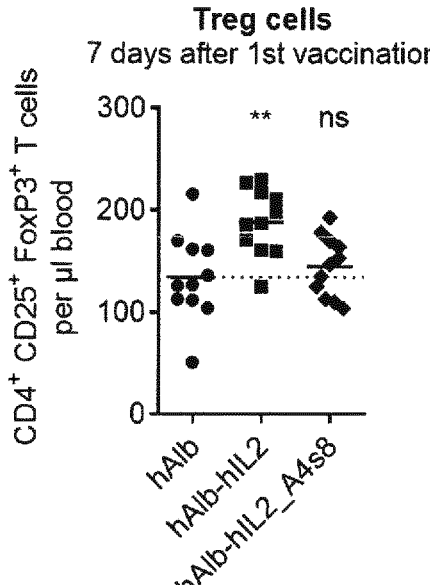
Figure 9:
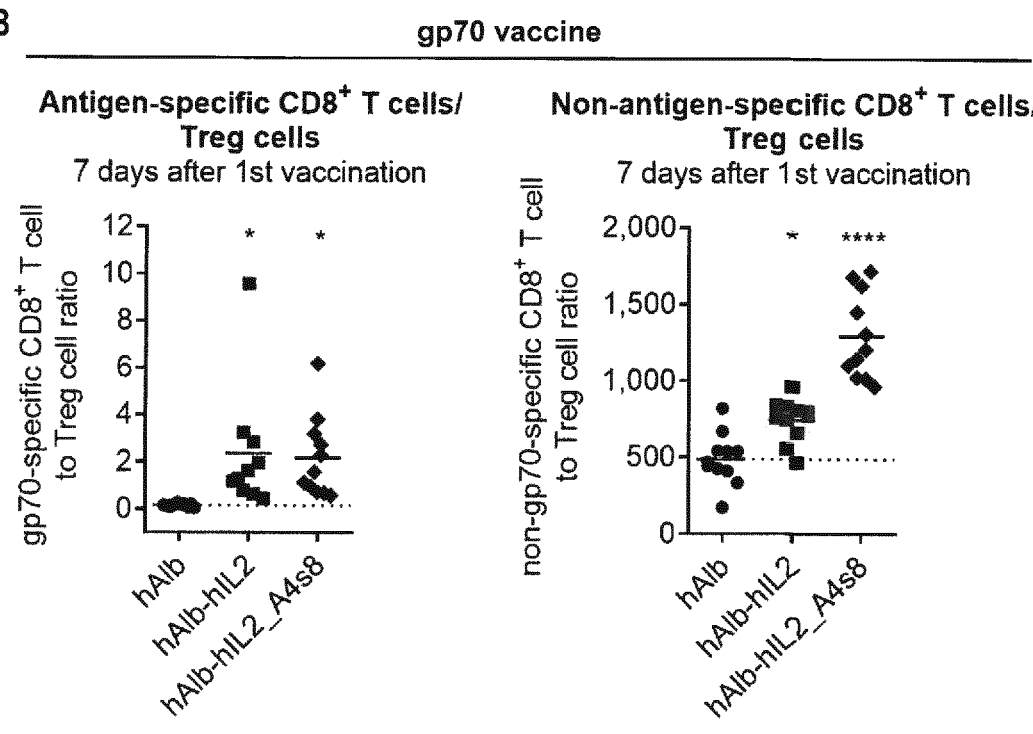

FIG. 9: Expansion of tumor antigen-specific $CD8^+$ T cells over $T_{reg}$ cells upon treatment with hAlb-hIL2_A4s8 compared to hAlb-hIL2 in combination with a therapeutic RNA vaccine in the murine colon carcinoma model CT26.

(A) Absolute numbers of non-antigen-specific $CD8^+$ T cells, $CD4^+$ T cells and $T_{reg}$ cells per µL blood determined seven days after the first treatment (day 17) via flow cytometry from BALB/c mice described in Example 6, FIG. 7 and FIG. 8. (B) Ratio of antigen-specific $CD8^+$ T cells (left) or non-antigen-specific $CD8^+$ T cells (right) over $T_{reg}$ cells. Dots represent individual mice, lines represent the group mean. Statistical significance was determined using one-way ANOVA followed by Dunnett's multiple comparisons test. All analyses were two-tailed and carried out using GraphPad Prism 8. ns $P>0.05$, *$P<0.05$, $P<0.01$, **$P<0.0001$.

Figure 10:
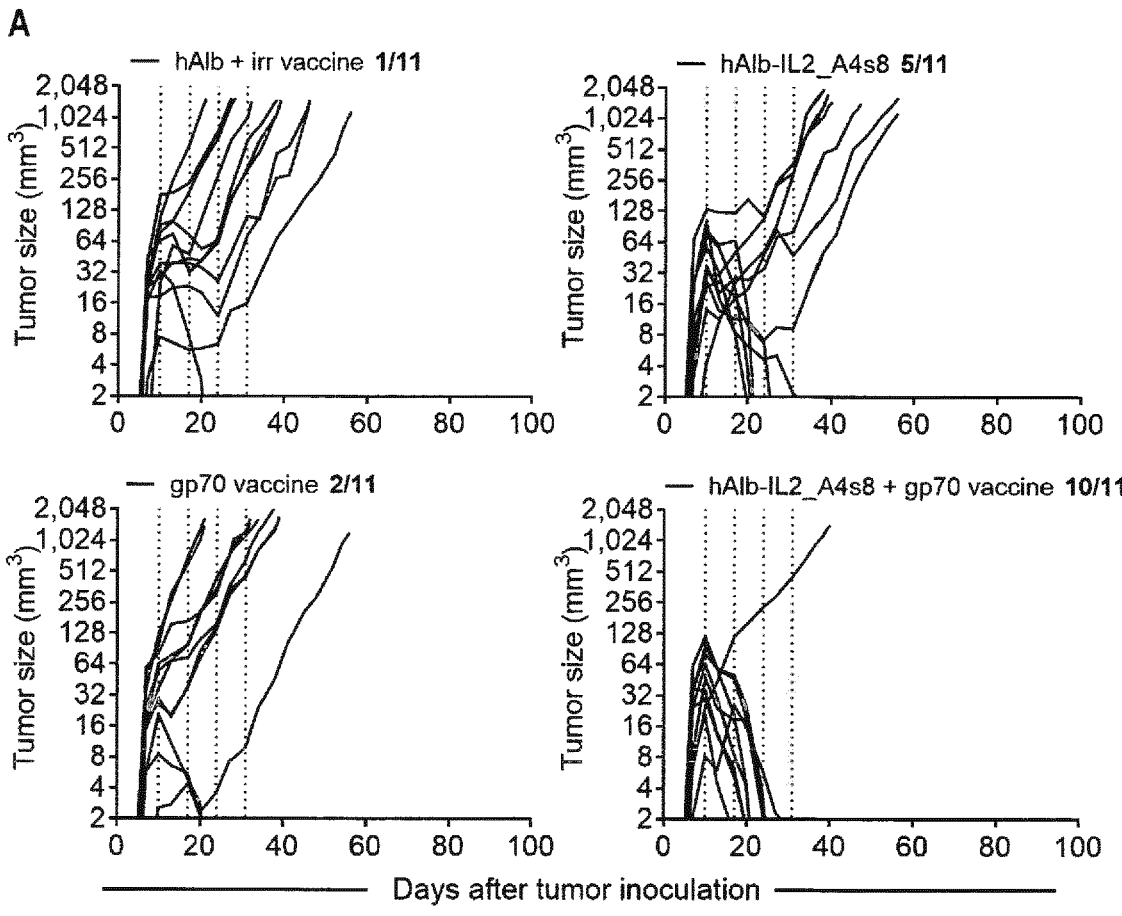
Figure 10:
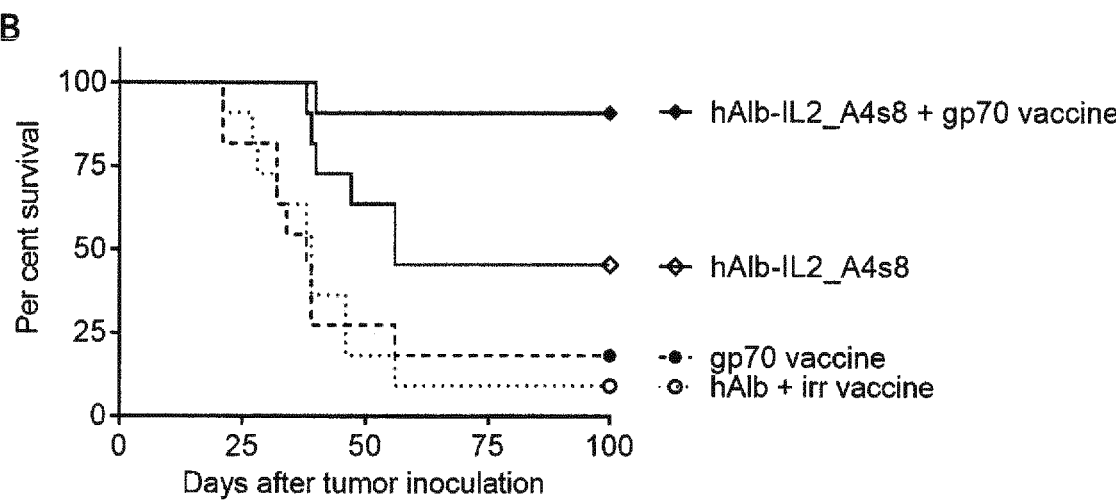

FIG. 10: Reduced tumor growth resulting in improved survival after treatment with hAlb-hIL2_A4s8 alone in the murine colon carcinoma model CT26.

BALB/c mice (n=11 per group) were inoculated with $5\times10^5$ CT26 tumor cells subcutaneously (s.c.) and treated intravenously (i.v.) four times weekly (day 10, 17, 24 and 31) with RNA coding for hAlb-hIL2_A4s8 and formulated as LNP, with or without concomitant i.v. vaccination with 20 µg gp70 RNA-LPX. The control group received an RNA vaccine not coding for any antigen (irr vaccine) with hAlb (not coding for any cytokine) formulated as LNPs, or gp70 vaccine alone. (A) Tumor growth of individual mice and (B) survival of mice treated with hAlb-hIL2_A4s8 with or without gp70 vaccine. Dotted lines indicate treatment days. Ratios in (A) represent the number of tumor-free mice over the total number of mice per group.

Figure 11:
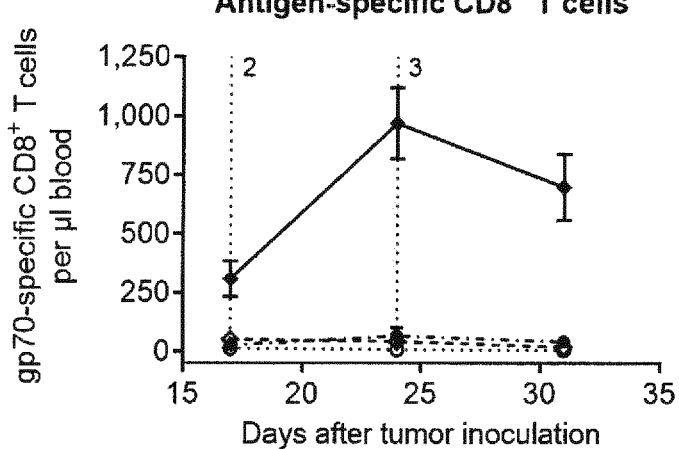
Figure 11:
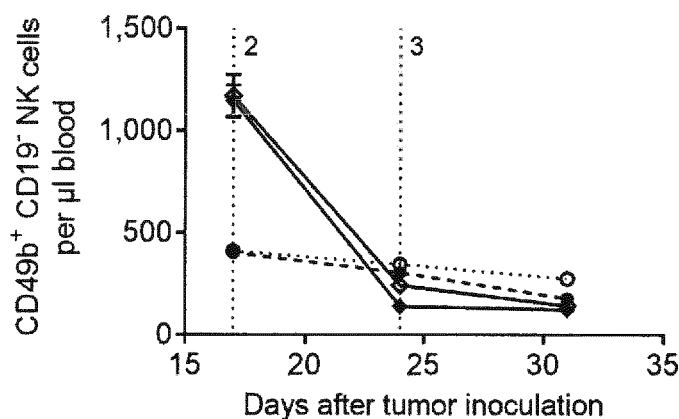
Figure 11:
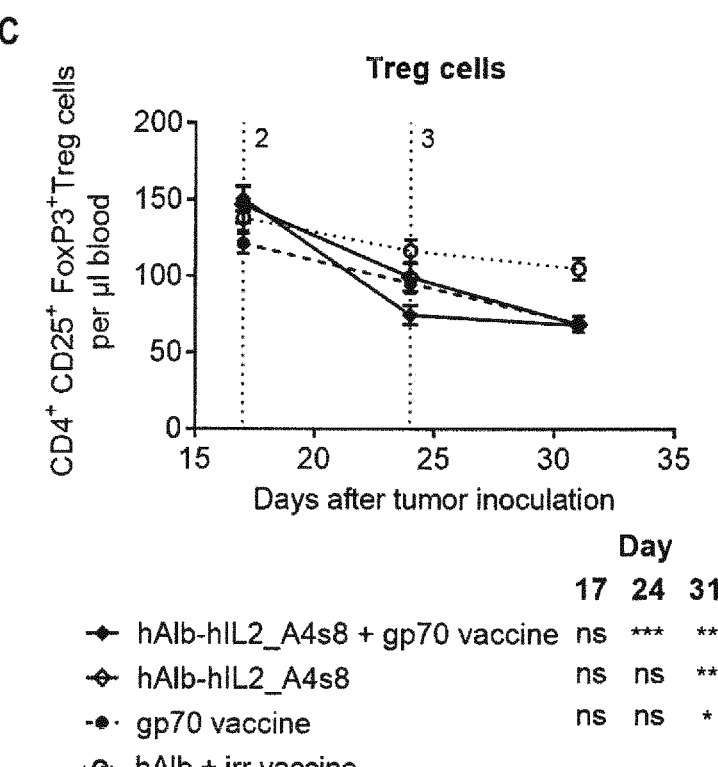

FIG. 11: Expansion of tumor antigen-specific $CD8^+$ T cells and NK cells while not affecting $T_{reg}$ cells upon treatment with hAlb-hIL2_A4s8 in the murine colon carcinoma model CT26.

(A) Absolute numbers of gp70-specific T cells, (B) NK cells, and (C) $T_{reg}$ cells per µL blood determined seven days after the first three treatments (day 17, 24 and 31) via flow cytometry from BALB/c mice described in Example 7 and FIG. 10. Dotted lines indicate treatment days, numbers at dotted lines indicate number of treatments. Mean±SEM. Statistical significance was determined using two-way ANOVA followed by Dunnett's multiple comparisons test. All analyses were two-tailed and carried out using GraphPad Prism 8. ns $P>0.05$, *$P<0.05$, $P<0.01$, *$P<0.001$, ****$P<0.0001$.

Figure 12:
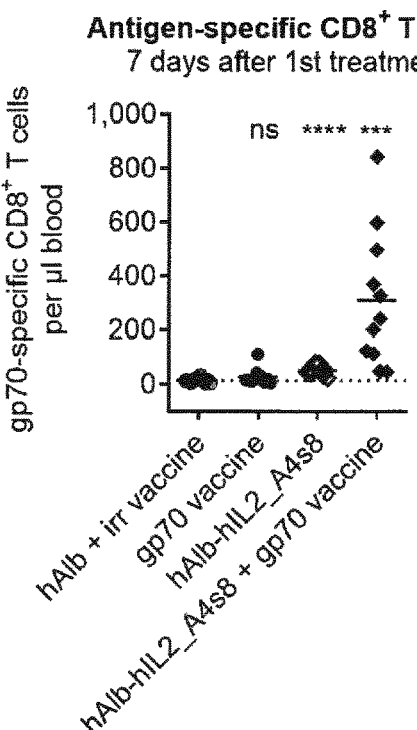
Figure 12:
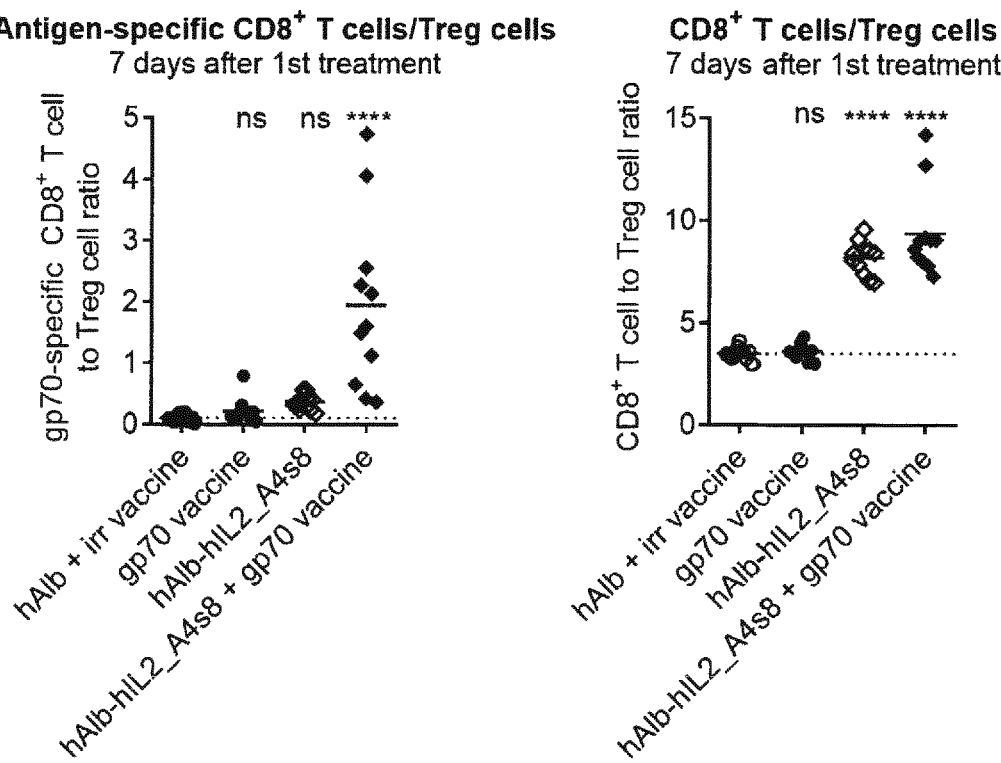
Figure 12:
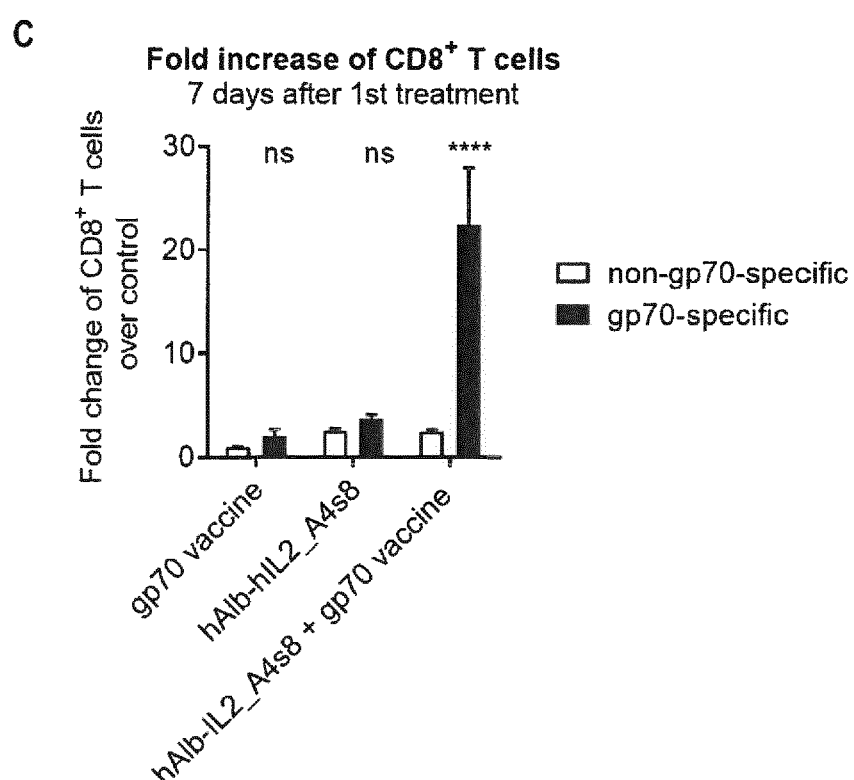

FIG. 12. Expansion of tumor antigen-specific $CD8^+$ T cells over $T_{reg}$ cells upon treatment with hAlb-hIL2_A4s8 in the murine colon carcinoma model CT26.

(A) Absolute numbers of antigen-specific $CD8^+$ T cells, total $CD8^+$ T cells and $CD4^+$ T cells per µL blood determined seven days after the first treatment (day 17) via flow cytometry from BALB/c mice described in Example 6, FIG. 10 and FIG. 11. (B) Ratio of antigen-specific $CD8^+$ T cells (left) or total $CD8^+$ T cells (right) over $T_{reg}$ cells. (C) Fold change of $CD8^+$ T-cell subsets in treated groups over the corresponding medians of $CD8^+$ T-cell subsets in the control group. Dots represent individual mice, lines represent the group mean. Mean±SEM. Statistical significance was determined using one-way ANOVA followed by Dunnett's multiple comparisons test. All analyses were two-tailed and carried out using GraphPad Prism 8. ns P>0.05, *P<0.05, P<0.01, *P<0.001, ****P<0.0001.

Figure 13:
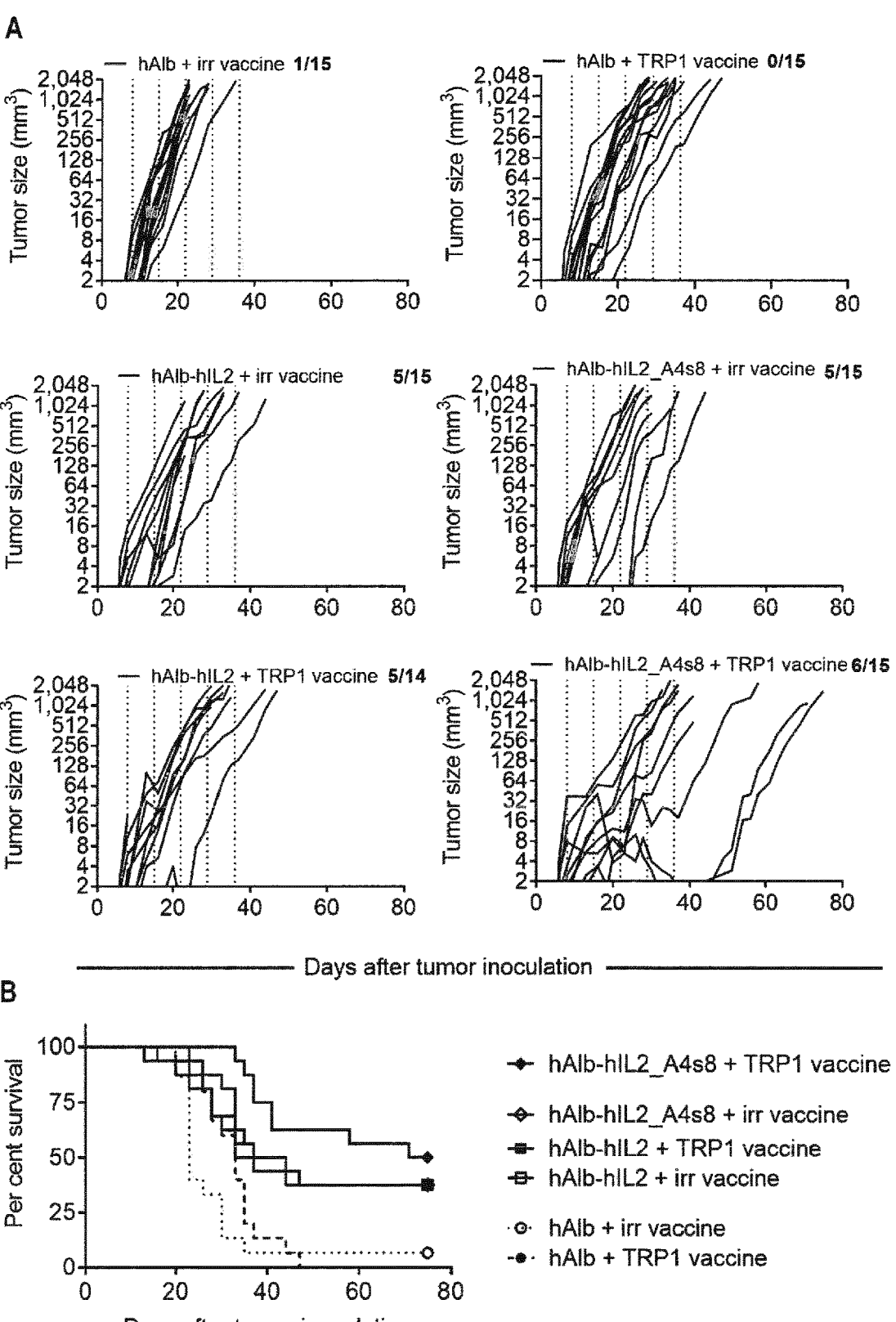

FIG. 13: Reduced tumor growth resulting in improved survival after treatment with hAlb-hIL2_A4s8 compared to hAlb-hIL2 in combination with a therapeutic RNA vaccine in the murine melanoma model B16.

C57BL/6 mice (n=15 per group) were inoculated subcutaneously (s.c.) with $3 \times 10^5$ B16-F10 melanoma cells and treated intravenously (i.v.) five times weekly (day 8, 15, 22, 29 and 36) with RNA coding for hAlb-hIL2 or hAlb-hIL2_A4s8 and formulated as LNP, with or without concomitant i.v. vaccination with 20 µg TRP1 RNA-LPX. The control group received an RNA vaccine not coding for any antigen (irr vaccine) with hAlb (not coding for any cytokine) formulated as LNPs, or hAlb with the TRP1 vaccine. (A) Tumor growth of individual mice and (B) survival of mice treated with hAlb-hIL2 or hAlb-hIL2_A4s8 with or without TRP1 vaccine. Dotted lines indicate treatment days. Ratios in (A) represent the number of tumor-free mice over the total number of mice per group.

Figure 14:
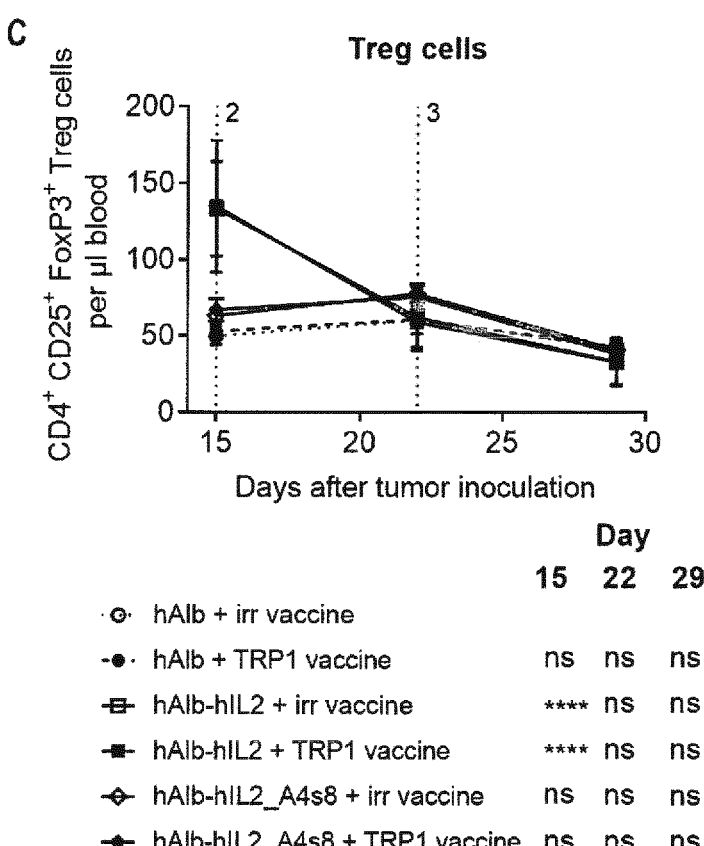

FIG. 14: Expansion of tumor antigen-specific CD8$^+$ T cells and NK cells while not affecting T$_{reg}$ cells upon treatment with hAlb-hIL2_A4s8 compared to hAlb-hIL2 in combination with a therapeutic RNA vaccine in the murine melanoma model B16.

(A) Absolute numbers of TRP1-specific T cells, (B) NK cells, and (C) T$_{reg}$ cells per µl blood determined seven days after the first three treatments (day 15, 22 and 29) via flow cytometry from C57BL/6 mice described in Example 8 and FIG. 13. Dotted lines indicate treatment days, numbers at dotted lines indicate number of treatments. Mean±SEM. Statistical significance was determined using two-way ANOVA followed by Dunnett's multiple comparisons test. All analyses were two-tailed and carried out using GraphPad Prism 8. ns P>0.05, *P<0.05, P<0.01, *P<0.001, ****P<0.0001.

Figure 15:
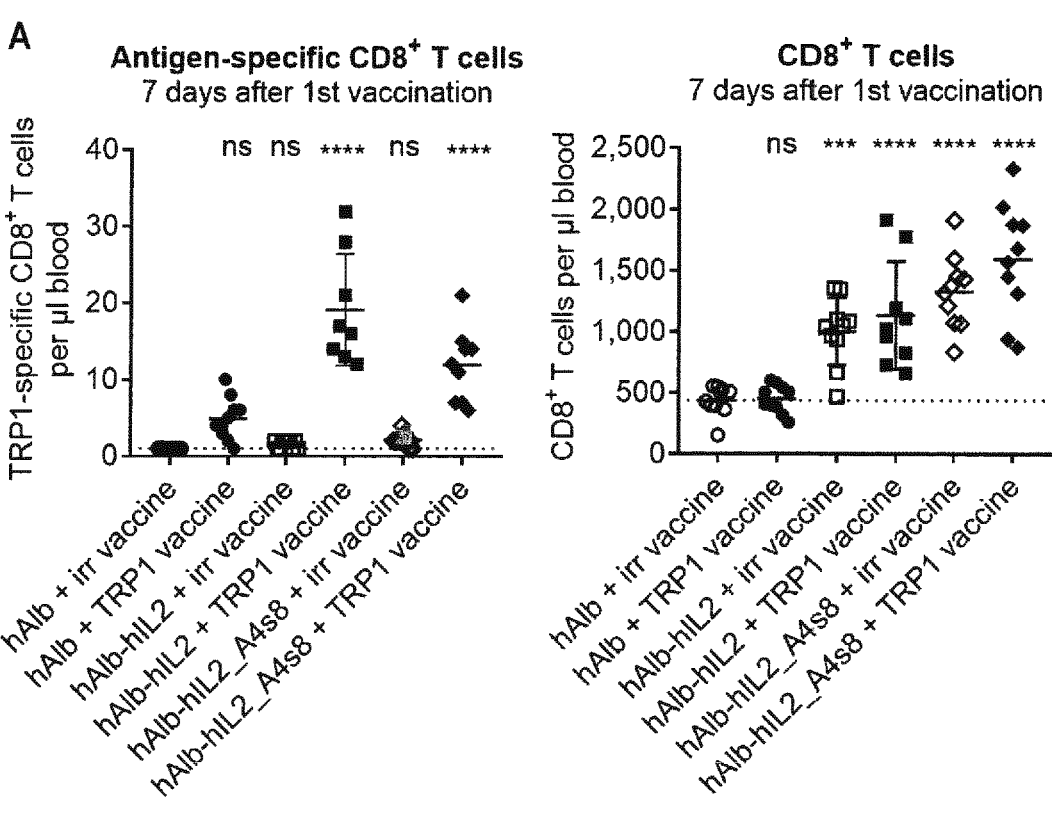
Figure 15:
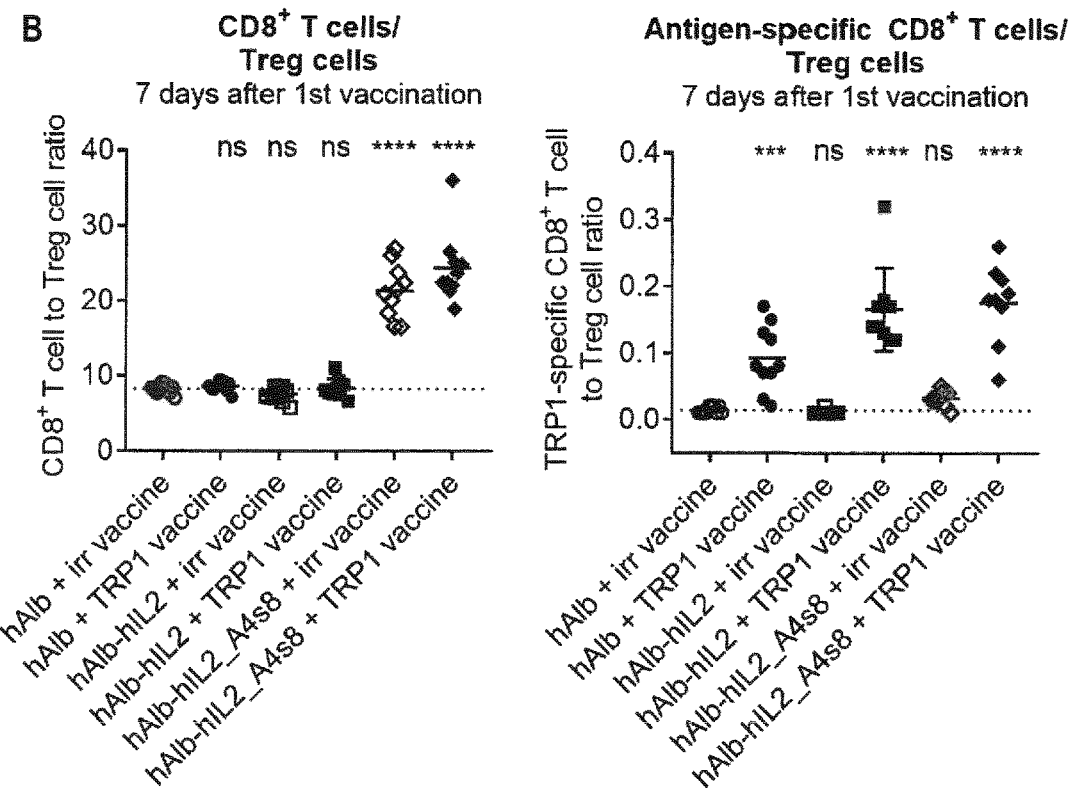
Figure 15:
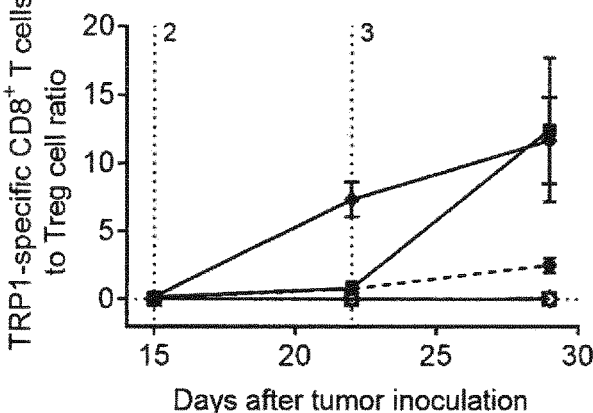
Figure 15:
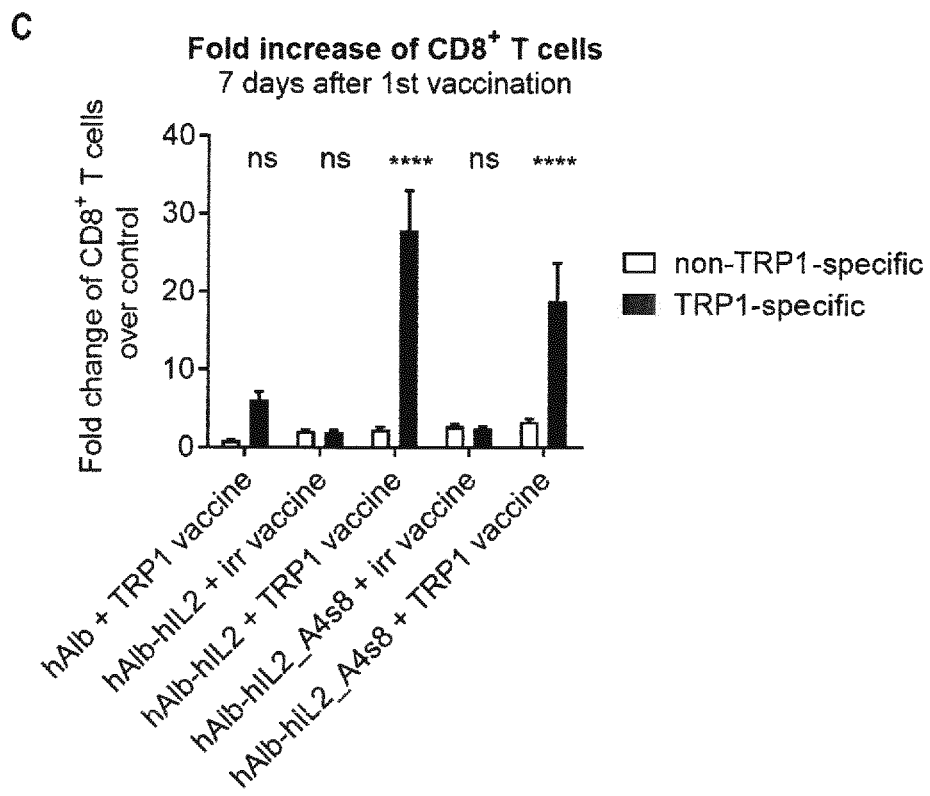

FIG. 15: Expansion of tumor antigen-specific CD8$^+$ T cells over T$_{reg}$ cells upon treatment with hAlb-hIL2_A4s8 and hAlb-hIL2 in combination with a therapeutic RNA vaccine in the murine melanoma model B16.

(A) Absolute numbers of antigen-specific CD8$^+$ T cells, total CD8$^+$ T cells and CD4$^+$ T cells per µL blood determined seven days after the first treatment (day 15) via flow cytometry from C57BL/6 mice described in Example 8, FIG. 13 and FIG. 14. (B) Ratio of total CD8$^+$ T cells (top left) and antigen-specific CD8$^+$ T cells (top right, bottom left) over T$_{reg}$ cells. (C) Fold change of CD8$^+$ T-cell subsets in treated groups over the corresponding medians of CD8$^+$ T-cell subsets in the control group. Dots represent individual mice, lines represent the group mean. Mean±SEM. Statistical significance was determined using one-way ANOVA followed by Dunnett's multiple comparisons test. All analyses were two-tailed and carried out using GraphPad Prism 8. ns P>0.05, *P<0.05, P<0.01, *P<0.001, ****P<0.0001.

Figure 16:
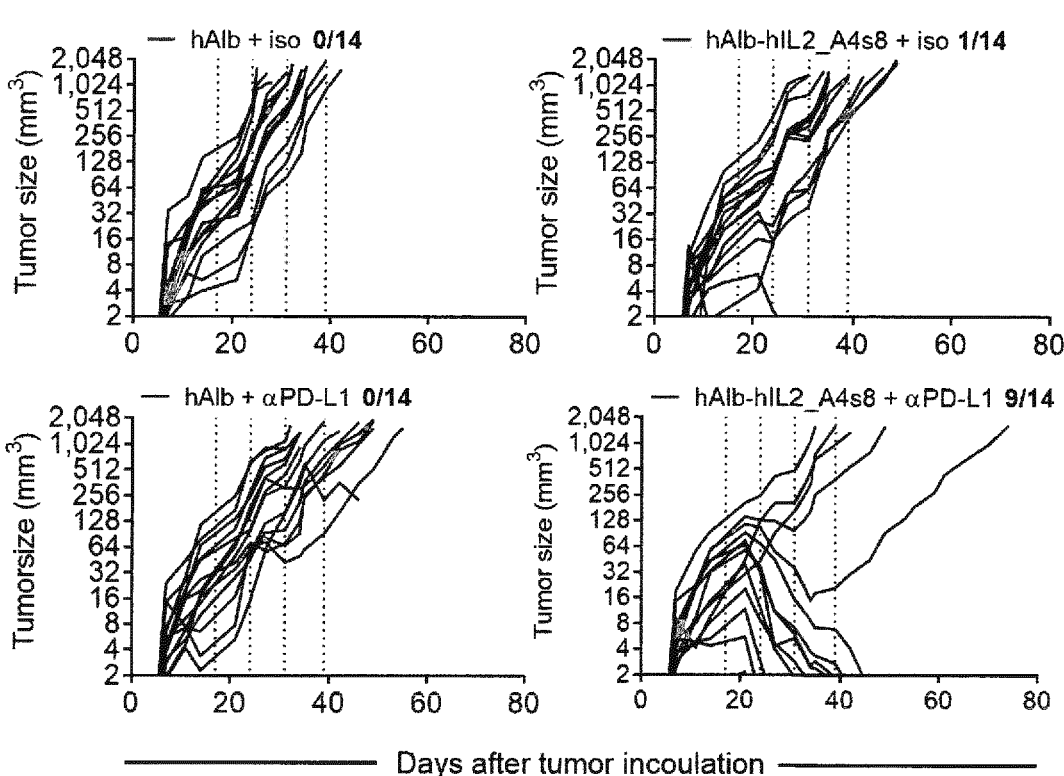
Figure 16:
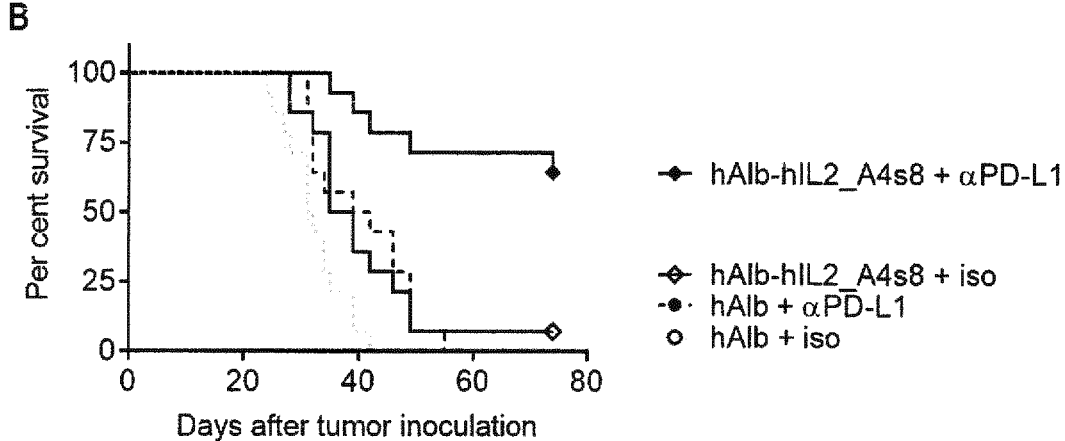

FIG. 16: Reduced tumor growth resulting in improved survival after treatment with hAlb-hIL2_A4s8 in combination with PD-L1 blockade in the murine colon carcinoma model MC38. C57BL/6 mice (n=14 per group) were inoculated subcutaneously (s.c.) with $7.5 \times 10^5$ MC38 colon carcinoma cells and treated i.v. four times weekly (day 17, 24, 32 and 39) with RNA coding for hAlb-hIL2_A4s8 and formulated as LNP, with or without concomitant intraperitoneal (i.p.) treatment with anti-PD-L1 antibody (first injection 200 µg, then 100 µg for all consecutive injections). Control groups received hAlb (not coding for any cytokine) formulated as LNPs and isotype control antibody, or hAlb and anti-PD-L1. Blood lymphocyte subsets and Adpgk-specific T-cell responses were determined seven days after the second treatment (day 31) via flow cytometry. (A) Tumor growth of individual mice and (B) survival of mice treated with hAlb-hIL2_A4s8 with or without anti-PD-L1 antibody. Dotted lines indicate treatment days. Ratios in (A) represent the number of tumor-free mice over the total number of mice per group.

Figure 17:
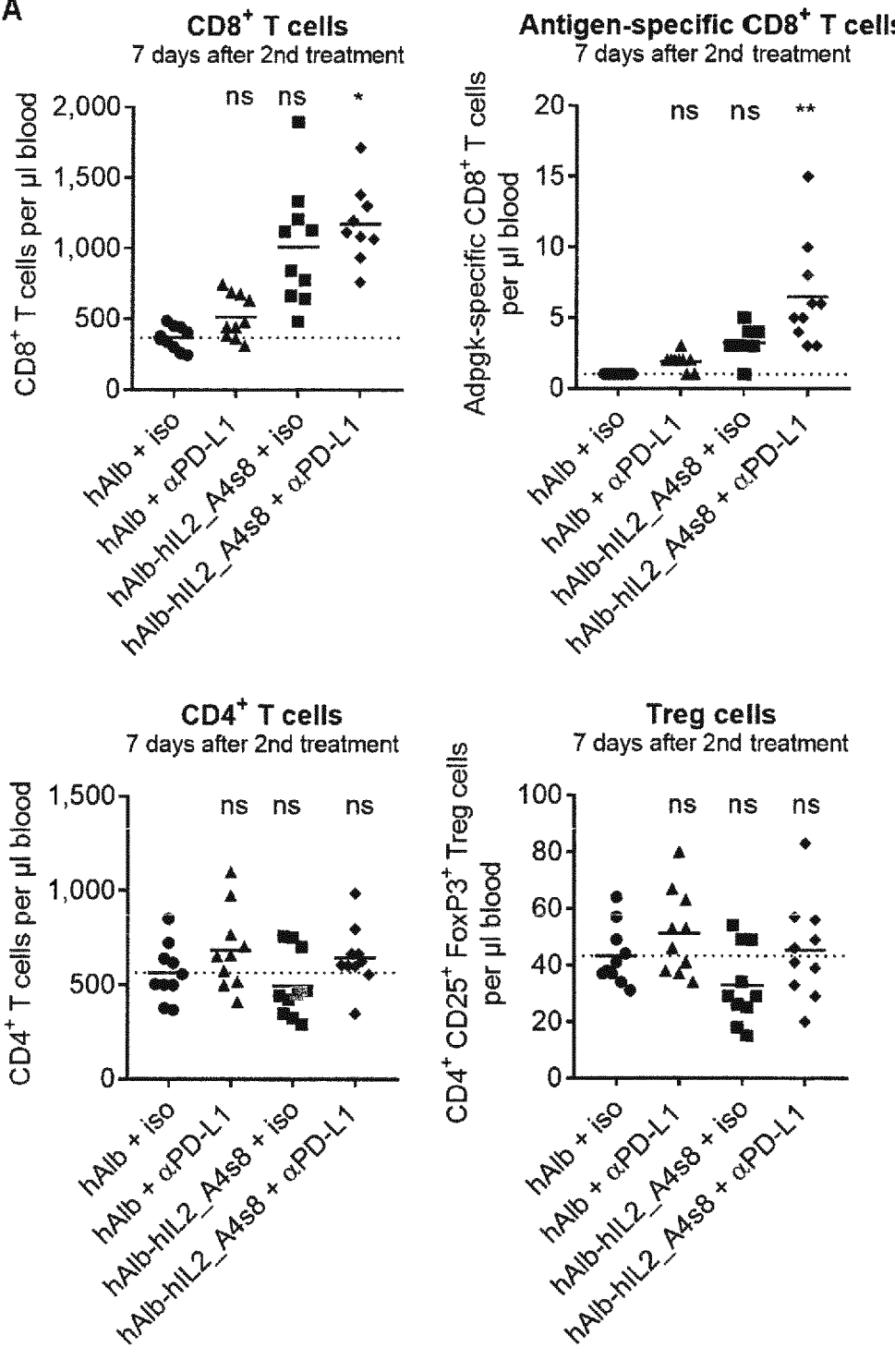
Figure 17:
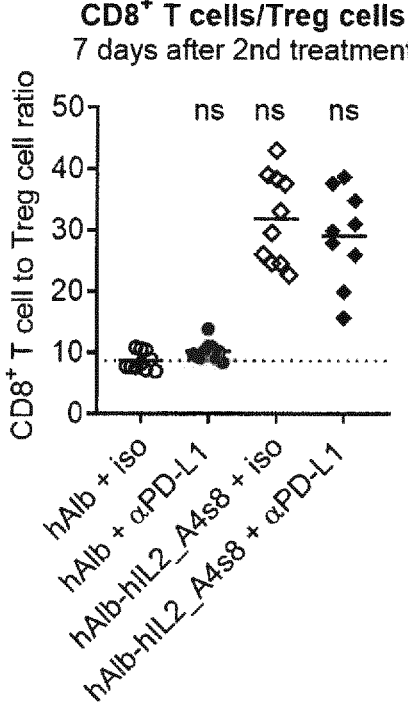
Figure 17:
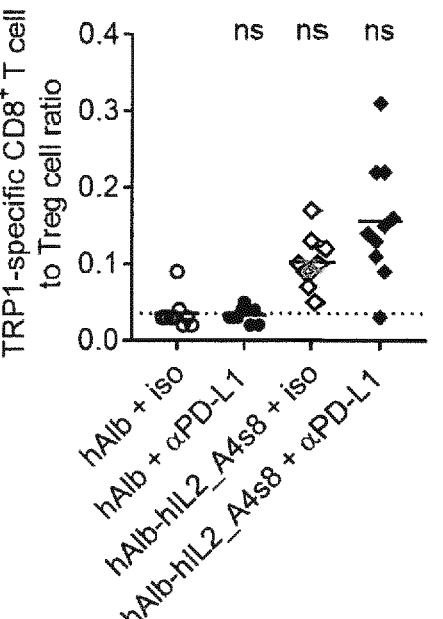

FIG. 17: Expansion of tumor antigen-specific CD8$^+$ T cells over T$_{reg}$ cells upon treatment with hAlb-hIL2_A4s8 in combination with PD-L1 blockade in the murine colon carcinoma model MC38. (A) Absolute numbers of total CD8$^+$ T cells, antigen-specific CD8$^+$ T cells, total CD4$^+$ T cells and T$_{reg}$ cells per µL blood determined seven days after the second treatment (day 31) via flow cytometry from C57BL/6 mice described in Example 9, FIG. 16. (B) Ratio of total CD8$^+$ T cells (left) and antigen-specific CD8$^+$ T cells (right) over T$_{reg}$ cells. Dots represent individual mice, lines represent the group mean. Statistical significance was determined using one-way ANOVA followed by Dunnett's multiple comparisons test. All analyses were two-tailed and carried out using GraphPad Prism 8. ns P>0.05, *P<0.05, P<0.01, *P<0.001, ****P<0.0001.

Figure 18:
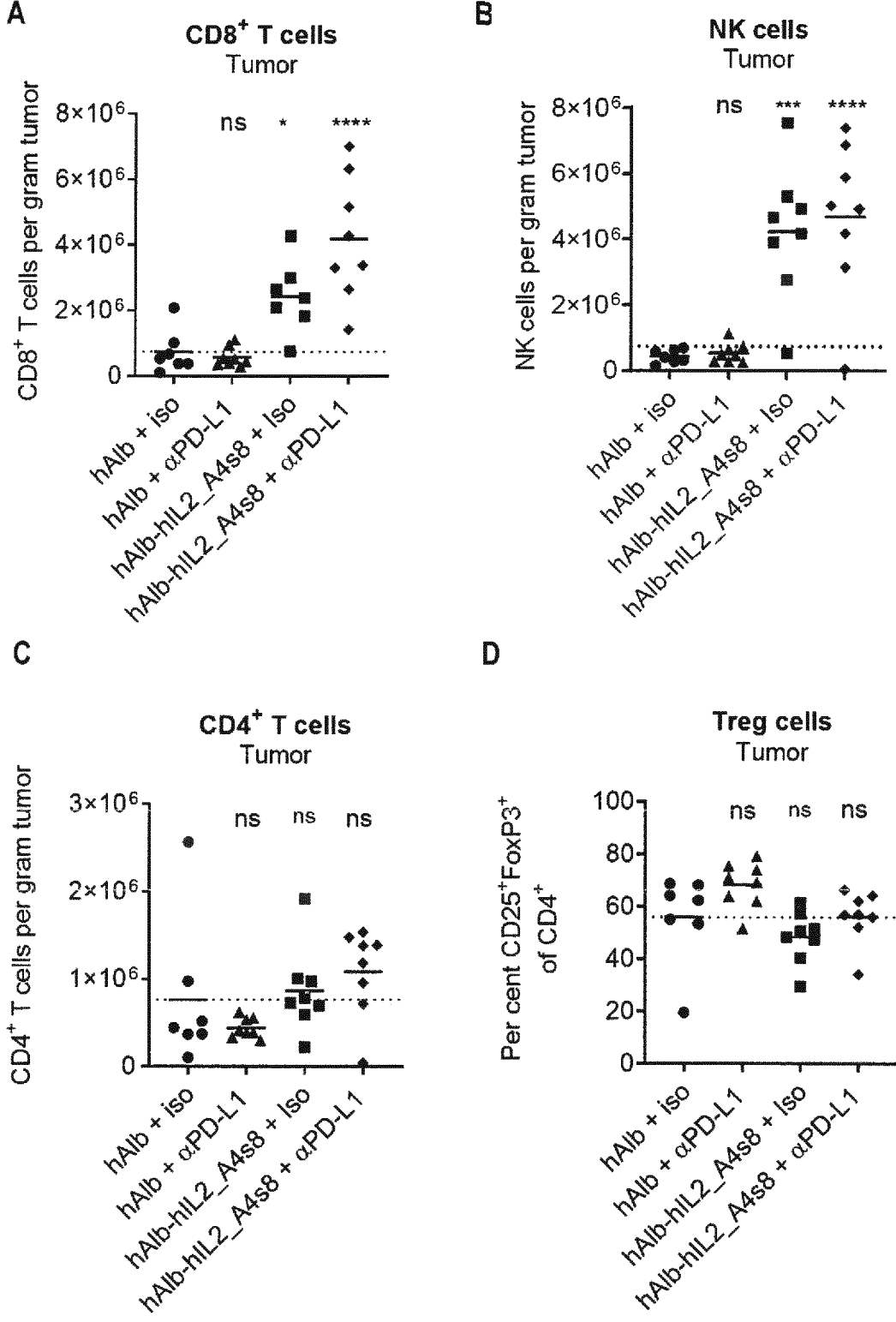
Figure 18:
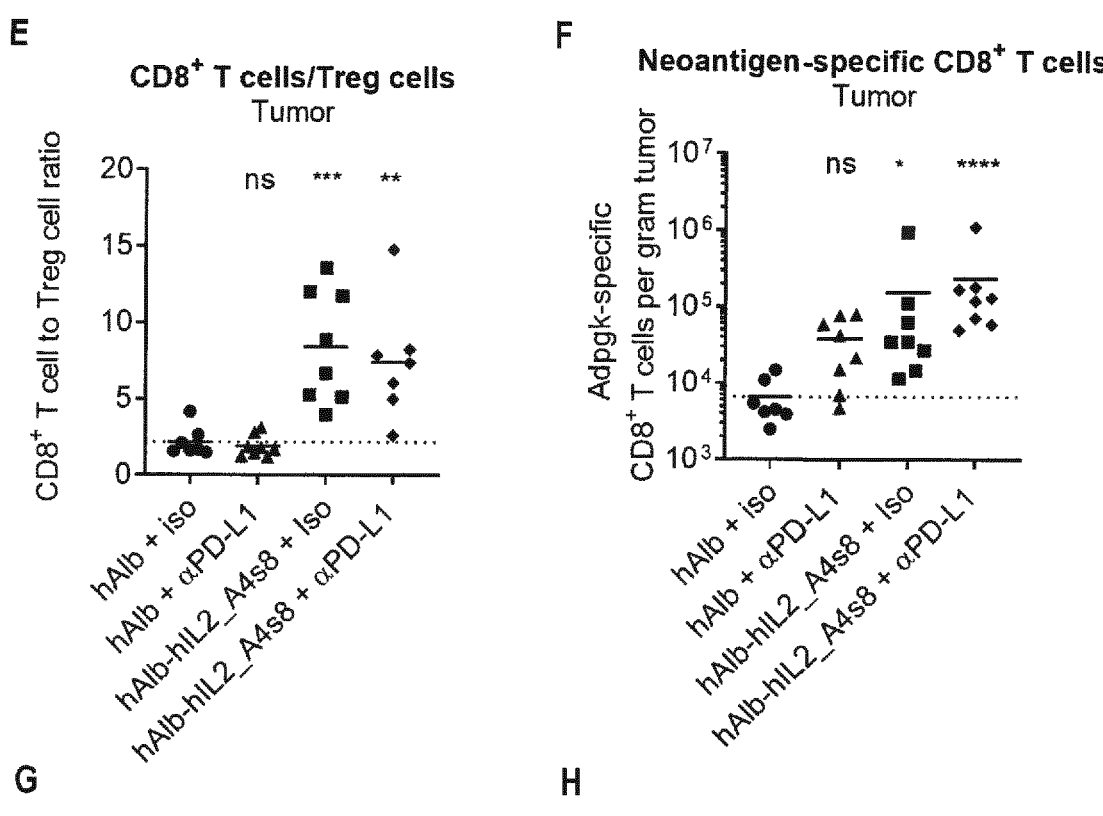
Figure 18:
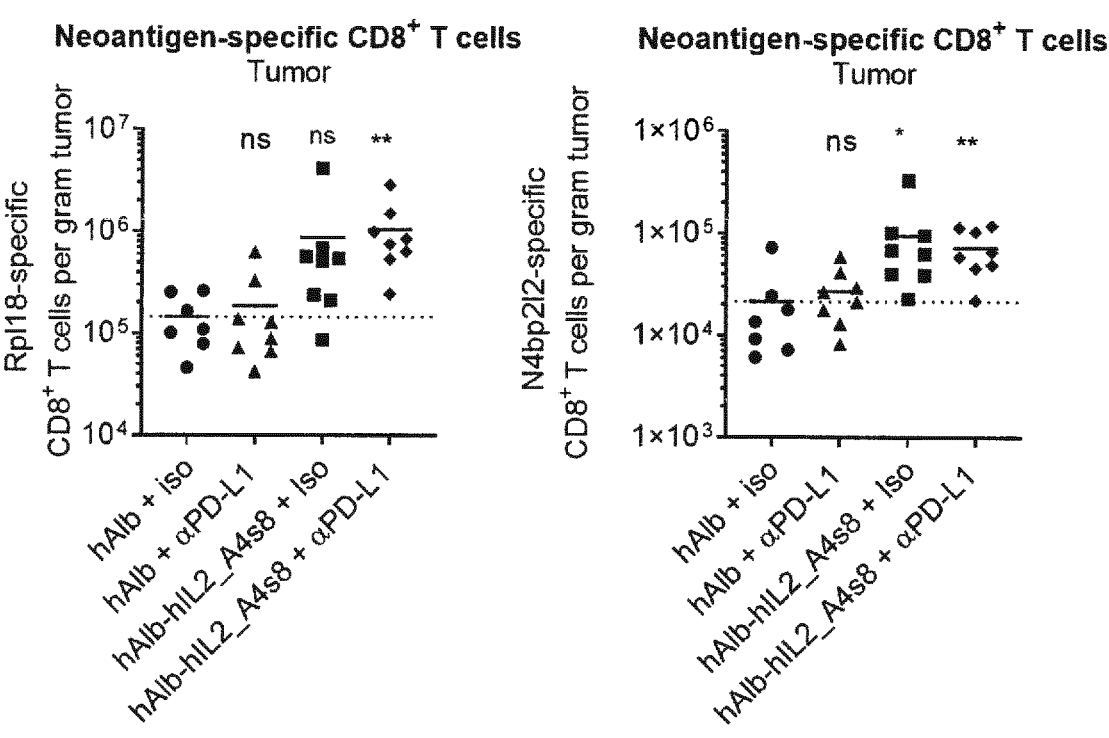
Figure 18:
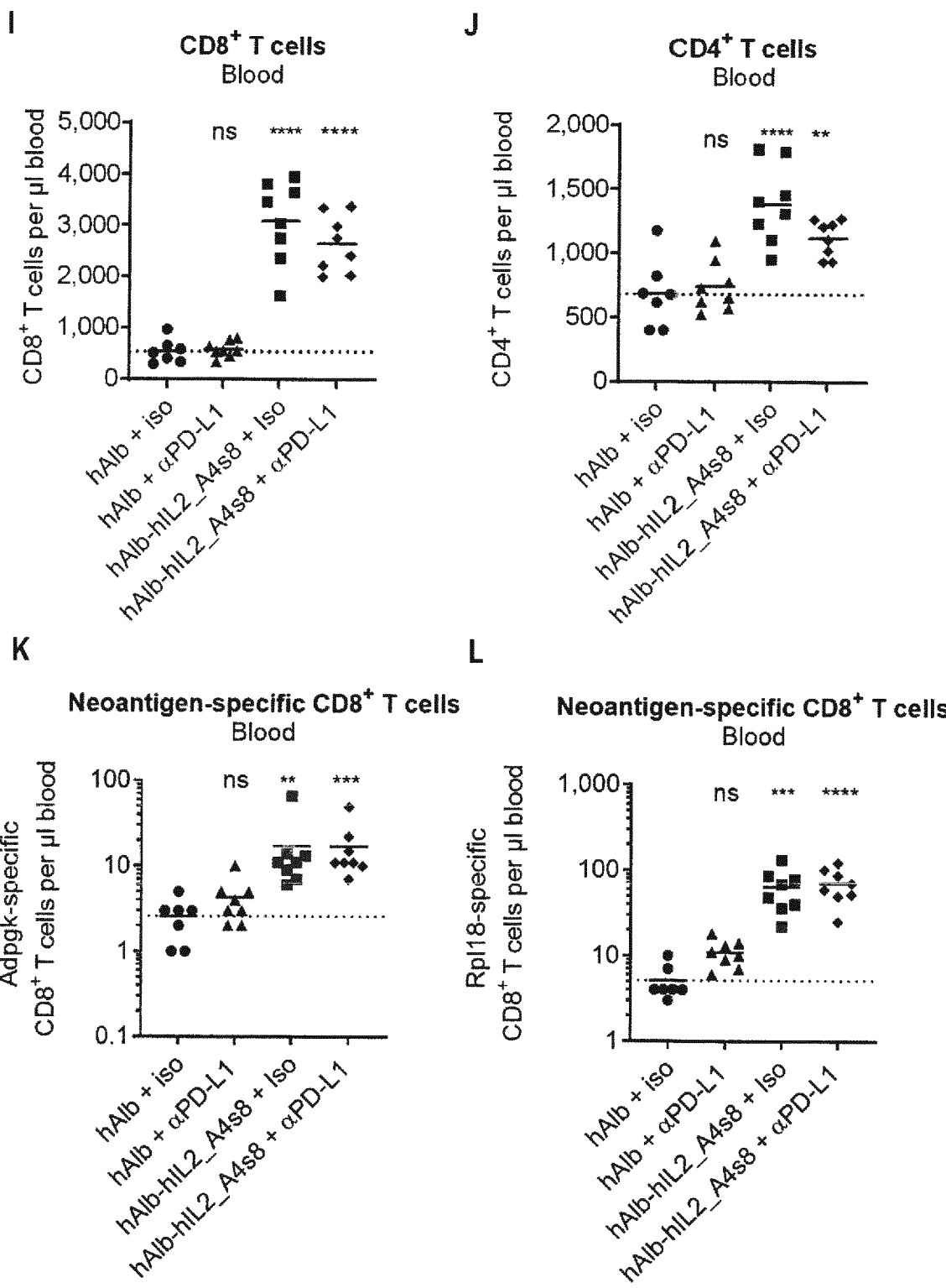
Figure 18:
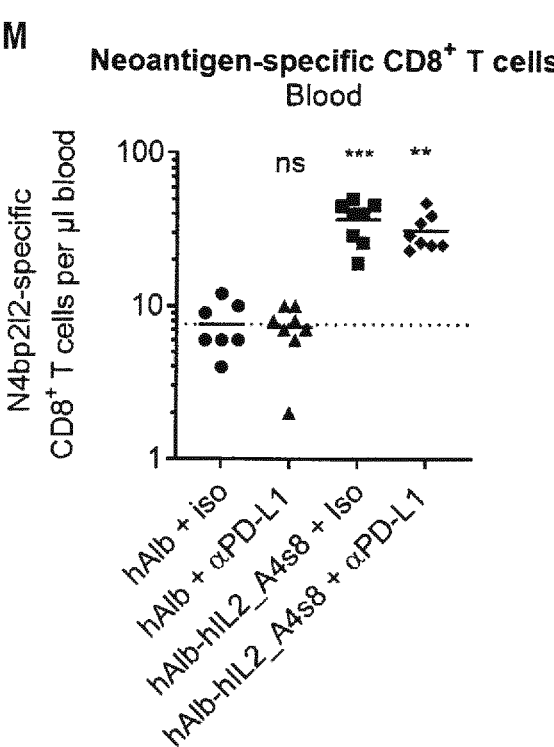

FIG. 18: Modulation of lymphocyte numbers in the tumor and the blood upon treatment with hAlb-hIL2_A4s8 in combination with PD-L1 checkpoint blockade in the murine tumor model MC38. C57BL/6 mice (n=7-8 per group) were inoculated subcutaneously (s.c.) with $7.5 \times 10^5$ MC38 colon carcinoma cells and 19 days later treated i.v. with LNP formulated RNA coding for hAlb-hIL2_A4s8 and concomitant i.p. treatment with anti-PD-L1 antibody. Control groups received one out of the two therapies or received no treatment at all (control for hAlb-hIL2_A4s8: hAlb RNA formulated as LNPs ('hAlb'); control for anti-PD-L1 antibody: Isotype antibody ('iso')). Tumor and blood of mice were sampled on day 24 and analyzed by flow cytometry. (A-H) Analysis of tumor infiltrating lymphocyte subsets. Numbers of (A) CD8$^+$ T cells, (B) NK cells and (C) CD4$^+$ T cells. (D) Fraction of CD25$^+$ FoxP3$^+$ T$_{reg}$ cells among CD4$^+$ T cells. (E) Ratio of CD8$^+$ T cells to T$_{reg}$ cells. Numbers of (F) Adpgk, (G) Rpl18 and (H) N4bp2l2 neoantigen-specific CD8$^+$ T cells. (I-M) Analysis of lymphocyte subsets in the blood. Numbers of (I) CD8$^+$ and (J) CD4$^+$ T cells as well as (K) Adpgk, (L) Rpl18 and (M) N4bp2l2 neoantigen-specific CD8$^+$ T cells. Statistical analysis was performed using a Kruskal-Wallis test (graphs with a log 10 scale) or one-way ANOVA test (graphs with a linear scale) followed by Dunn's or Dunnett's multiple comparison test, respectively. All analyses were two-tailed and carried out using GraphPad Prism 8. ns P>0.05, *P<0.05, P<0.01, *P<0.001, ****P<0.0001.

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU- PAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

In the following, definitions will be provided which apply to all aspects of the present disclosure. The following terms have the following meanings unless otherwise indicated. Any undefined terms have their art recognized meanings.

Definitions

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of binding.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, or even more.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 50 amino acids, but the terms "peptide", "protein" and "polypeptide" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, cytokines, and antigens for vaccination.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

By "variant" or "variant protein" or "variant polypeptide" herein is meant a protein that differs from a wild type protein by virtue of at least one amino acid modification. The parent polypeptide may be a naturally occurring or wild type (WT) polypeptide, or may be a modified version of a wild type polypeptide. Preferably, the variant polypeptide has at least one amino acid modification compared to the parent polypeptide, e.g. from 1 to about 20 amino acid modifications, and preferably from 1 to about 10 or from 1 to about 5 amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild type polypeptide, or a variant or engineered version of a wild type polypeptide.

By "wild type" or "WT" or "native" herein is meant an amino acid sequence that is found in nature, including allelic variations. A wild type protein or polypeptide has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all splice variants, posttranslationally modified variants, conformations, isoforms and species homologs, in particular those which are naturally expressed by cells. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:
  glycine, alanine;
  valine, isoleucine, leucine;
  aspartic acid, glutamic acid;
  asparagine, glutamine;
  serine, threonine;
  lysine, arginine; and
  phenylalanine, tyrosine.

16

Preferably the degree of similarity, preferably identity between a given amino acid sequence and an amino acid sequence which is a variant of said given amino acid sequence will be at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS: needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to cytokines such as IL2, one particular function is one or more immunomodulatory activities displayed by the amino acid sequence from which the fragment or variant is derived and/or binding to the receptor(s) the amino acid sequence from which the fragment or variant is derived binds to. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., binding to a target molecule or contributing to binding to a target molecule. In one embodiment, the modifications in the amino acid sequence of the parent molecule or sequence do not significantly affect or alter the binding affinity of the molecule or sequence. In different embodiments, binding of the functional fragment or functional variant may be reduced but still significantly present, e.g., binding of the functional variant may be at least 50%, at least 60%, at least 70%, at least 80%, or at least 90% of the parent molecule or sequence. However, in other embodiments, binding of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the antigens and cytokines (e.g., IL2) suitable for use herein may be altered such that they vary in sequence from the naturally occurring or native sequences from which they were derived, while retaining the desirable activity of the native sequences.

As used herein, an "instructional material" or "instructions" includes a publication, a recording, a diagram, or any other medium of expression which can be used to communicate the usefulness of the compositions and methods of the invention. The instructional material of the kit of the invention may, for example, be affixed to a container which contains the compositions of the invention or be shipped together with a container which contains the compositions. Alternatively, the instructional material may be shipped separately from the container with the intention that the instructional material and the compositions be used cooperatively by the recipient.

"Isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "genetic modification" or simply "modification" includes the transfection of cells with nucleic acid. The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, cells that are genetically modified to express a receptor polypeptide, e.g., IL2R or IL2R variant, and/or an antigen receptor, e.g., TCR or CAR, are stably transfected with nucleic acid encoding the receptor polypeptide and/or nucleic acid encoding the antigen receptor, while, generally, nucleic acid encoding a ligand polypeptide such as an IL2 variant and/or nucleic acid encoding antigen is transiently transfected into cells.

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a polynucleotide is preferably isolated.

Nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment of all aspects of the invention, nucleic acid such as nucleic acid encoding an IL2 variant, nucleic acid encoding an IL2R or IL2R variant, nucleic acid encoding an antigen receptor or nucleic acid encoding a vaccine antigen is expressed in cells, in particular cells of a subject treated to provide the IL2 variant, IL2R or IL2R variant, antigen receptor or vaccine antigen. In one embodiment of all aspects of the invention, the nucleic acid is transiently expressed in cells of the subject. Thus, in one embodiment, the nucleic acid is not integrated into the genome of the cells. In one embodiment of all aspects of the invention, the nucleic acid is RNA, preferably in vitro transcribed RNA.

The nucleic acids described herein may be recombinant and/or isolated molecules.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA may have modified ribonucleotides. Examples of modified ribonucleotides include, without limitation, 5-methylcytidine, pseudouridine and/or 1-methyl-pseudouridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) tail. Thus, the 3'-UTR is upstream of the poly(A) sequence (if present), e.g. directly adjacent to the poly(A) sequence.

In some embodiments, the RNA according to the present disclosure comprises a 3'-poly(A) sequence. As used herein, the term "poly(A) sequence" or "poly-A tail" refers to an uninterrupted or interrupted sequence of adenylate residues which is typically located at the 3' end of an RNA molecule. Poly(A) sequences are known to those of skill in the art and may follow the 3' UTR in the RNAs described herein. The poly(A) sequence may be of any length. In some embodiments, a poly(A) sequence comprises or consists of at least 20, at least 30, at least 40, at least 80, or at least 100 and up to 500, up to 400, up to 300, up to 200, or up to 150 nucleotides, and, in particular, about 100 nucleotides.

In some embodiments, the poly(A) sequence only consists of A nucleotides. In some embodiments, the poly(A) sequence essentially consists of A nucleotides, but is interrupted by a random sequence of the four nucleotides (A, C, G, and U), as disclosed in WO 2016/005324 A1, hereby incorporated by reference. Such random sequence may be 5 to 50, 10 to 30, or 10 to 20 nucleotides in length. A poly(A) cassette present in the coding strand of DNA that essentially consists of dA nucleotides, but is interrupted by a random sequence having an equal distribution of the four nucleotides (dA, dC, dG, dT) and having a length of e.g. 5 to 50 nucleotides shows, on DNA level, constant propagation of plasmid DNA in E. coli and is still associated, on RNA level, with the beneficial properties with respect to supporting RNA stability and translational efficiency.

In some embodiments, no nucleotides other than A nucleotides flank a poly(A) sequence at its 3' end, i.e., the poly(A) sequence is not masked or followed at its 3' end by a nucleotide other than A.

In the context of the present disclosure, the term "transcription" relates to a process, wherein the genetic code in a DNA sequence is transcribed into RNA. Subsequently, the RNA may be translated into peptide or protein.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "linked," "fused", or "fusion" are used interchangeably. These terms refer to the joining together of two or more elements or components or domains.

Cytokines are a category of small proteins (~5-20 kDa) that are important in cell signaling. Their release has an effect on the behavior of cells around them. Cytokines are involved in autocrine signalling, paracrine signalling and endocrine signalling as immunomodulating agents. Cytokines include chemokines, interferons, interleukins, lympho-kines, and tumor necrosis factors but generally not hormones or growth factors (despite some overlap in the terminology). Cytokines are produced by a broad range of cells, including immune cells like macrophages, B lympho-cytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

Interleukin-2 (IL2) is a cytokine that induces proliferation of antigen-activated T cells and stimulates natural killer (NK) cells. The biological activity of IL2 is mediated through a multi-subunit IL2 receptor complex (IL2R) of three polypeptide subunits that span the cell membrane: p55 (IL2Rα, the alpha subunit, also known as CD25 in humans), p75 (IL2Rβ, the beta subunit, also known as CD122 in humans) and p64 (IL2Rγ, the gamma subunit, also known as CD132 in humans). T cell response to IL2 depends on a variety of factors, including: (1) the concentration of IL2; (2) the number of IL2R molecules on the cell surface; and (3) the number of IL2R occupied by IL2 (i.e., the affinity of the binding interaction between IL2 and IL2R (Smith, "Cell Growth Signal Transduction is Quantal" In Receptor Activation by Antigens, Cytokines, Hormones, and Growth Factors 766:263-271, 1995)). The IL2:IL2R complex is internalized upon ligand binding and the different components undergo differential sorting. When administered as an intravenous (i.v.) bolus, IL2 has a rapid systemic clearance (an initial clearance phase with a half-life of 12.9 minutes followed by a slower clearance phase with a half-life of 85 minutes) (Konrad et al., Cancer Res. 50:2009-2017, 1990).

In eukaryotic cells human IL2 is synthesized as a precursor polypeptide of 153 amino acids, from which 20 amino acids are removed to generate mature secreted IL2. Recombinant human IL2 has been produced in E. coli, in insect cells and in mammalian COS cells.

Outcomes of systemic IL2 administration in cancer patients are far from ideal. While 15 to 20 percent of patients respond objectively to high-dose IL2, the great majority do not, and many suffer severe, life-threatening side effects, including nausea, confusion, hypotension, and septic shock. The severe toxicity associated with high-dose IL2 treatment is largely attributable to the activity of natural killer (NK) cells. Attempts to reduce serum concentration by reducing dose and adjusting dosing regimen have been attempted, and while less toxic, such treatments were also less efficacious.

According to the disclosure, in certain embodiments, the IL2 variant polypeptides described herein comprise a pharmacokinetic modifying group. In one embodiment, the IL2 variant portion or mutein described herein is attached to a pharmacokinetic modifying group. The resulting molecule, hereafter referred to as "extended-pharmacokinetic (PK) IL2," has a prolonged circulation half-life relative to free IL2. The prolonged circulation half-life of extended-PK IL2 permits in vivo serum IL2 concentrations to be maintained within a therapeutic range, potentially leading to the enhanced activation of many types of immune cells, including T cells. Because of its favorable pharmacokinetic profile, extended-PK IL2 can be dosed less frequently and for longer periods of time when compared with unmodified IL2.

As used herein, "half-life" refers to the time taken for the serum or plasma concentration of a compound such as a peptide or protein to reduce by 50%, in vivo, for example due to degradation and/or clearance or sequestration by natural mechanisms. An extended-PK interleukin (IL) suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

As used herein, "human IL2" or "wild type human IL2" means IL2, whether native or recombinant, having the normally occurring 133 amino acid sequence of native human IL2 (less the signal peptide, consisting of an additional 20 N-terminal amino acids), whose amino acid sequence is described in Fujita, et. al, PNAS USA, 80, 7437-7441 (1983), with or without an additional N-terminal Methionine which is necessarily included when the protein is expressed as an intracellular fraction in E. coli. In one embodiment, human IL2 comprises the amino acid sequence of SEQ ID NO: 1. In one embodiment, a functional variant of human IL2 comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1. In one embodiment, a functional variant of human IL2 binds to the IL2 receptor.

In certain embodiments described herein, the IL2 variant portion or mutein is fused to a heterologous polypeptide (i.e., a polypeptide that is not IL2 and preferably is not a variant of IL2). The heterologous polypeptide can increase the circulating half-life of IL2. As discussed in further detail infra, the polypeptide that increases the circulating half-life may be serum albumin, such as human or mouse serum albumin.

As used herein, "IL2 mutein" means a variant of IL2 (including functional variants thereof), in particular a polypeptide wherein specific substitutions to the IL2 protein have been made.

In one embodiment, substitutions to the human IL2 protein have been made enhancing IL2Rβγ ("mutβγ") binding, in particular CD122 binding. For example, the IL2 muteins may be characterized by amino acid substitutions of the native IL2 polypeptide chain such amino acid substitutions resulting, for example, in relatively increased affinity for IL2Rβγ when compared to wild type IL2, such that IL2 mediated stimulation no longer requires engagement of the IL2Rα. Such mutants are potent IL2 signaling agonists. Particularly preferred embodiments include the following: leucine (Leu) residue at position 80, arginine (Arg) residue at position 81, leucine (Leu) residue at position 85 and isoleucine (Ile) residue at position 92, relative to wild type human IL2 and numbered in accordance with wild type human IL2.

In one embodiment, further substitutions to the human IL2 protein have been made affecting IL2Rαβγ binding, in particular CD25 binding ("mutα"). For example, the IL2 muteins may also be characterized by amino acid substitutions of the native IL2 polypeptide chain such amino acid substitutions resulting, for example, in relatively decreased affinity for IL2Rαβγ, in particular the a subunit thereof, when compared to wild type IL2 (i.e., the IL2 muteins in addition to the "mutβγ" mutations also comprise "mutα" mutations). These mutations can be at amino acid residues that contact IL2Rα. Particularly preferred embodiments include the following: lysine (Lys) residue at position 35, lysine (Lys) residue at position 43, glutamic acid (Glu) residue at position 61 and glutamic acid (Glu) residue at position 62, relative to wild type human IL2 and numbered in accordance with wild type human IL2, or any combination thereof.

IL2 muteins may have an amino acid sequence identical to wild type IL2 at the other, non-substituted residues (i.e., the IL2 muteins comprise "mutβγ" and optionally "mutα" mutations, e.g., those mutations in which the sequence of SEQ ID NO: 2 or 11 differs from the sequence of SEQ ID NO: 1). However, the IL2 muteins may also be characterized by amino acid insertions, deletions, substitutions and modifications at one or more sites in or at the other residues of the native IL2 polypeptide chain. In accordance with this invention any such insertions, deletions, substitutions and modifications may result in an IL2 mutein that has enhanced affinity for IL2Rβγ while optionally having reduced affinity for IL2Rαβγ.

The substituted amino acid residue(s) can be, but are not necessarily, conservative substitutions.

By "numbered in accordance with wild type IL2" we mean identifying a chosen amino acid with reference to the position at which that amino acid normally occurs in the mature sequence of wild type IL2. Where insertions or deletions are made to the IL2 mutein, one of skill in the art will appreciate that an amino acid normally occurring at a certain position may be shifted in position in the mutein. However, the location of the shifted amino acid can be readily determined by inspection and correlation of the flanking amino acids with those flanking the amino acid in wild type IL2.

The IL2 variant polypeptides described herein and polynucleotides coding therefor can be produced by any suitable method known in the art. Such methods include introducing appropriate nucleotide changes into the nucleic acid encoding IL2 or by in vitro synthesis of the IL2 polynucleotide or protein. For example, a DNA sequence encoding the IL2 variant polypeptide described herein may be constructed and those sequences may be expressed in a suitably transformed host or in any other suitable expression system. This method will produce the IL2 variant polypeptides described herein and/or RNA encoding therefor. However, the IL2 variant polypeptides described herein and polynucleotides coding therefor may also be produced, albeit less preferably, by chemical synthesis.

IL2 variant polypeptides described herein may bind IL2Rβγ with an affinity that is greater than the affinity with which wild type IL2 binds IL2Rβγ. In one embodiment, IL2 variant polypeptides described herein may bind IL2Rαβγ with an affinity that is lower than the affinity with which wild type IL2 binds IL2Rαβγ.

Affinity of IL2 variant polypeptides described herein to IL2Rβγ may be at least 2-fold, at least 5-fold, at least 10-fold, at least 20-fold, at least 50-fold, or at least 100-fold greater than the affinity with which wild type IL2 binds IL2Rβγ. Further, affinity of IL2 variant polypeptides described herein to IL2Rαβγ may be at least 2-fold, at least 5-fold, at least 10-fold, at least 20-fold, at least 50-fold, or at least 100-fold lower than the affinity with which wild type IL2 binds IL2Rαβγ.

IL2 variant polypeptides described herein may have a decreased ability to stimulate regulatory T cells than wild type IL2, in particular when compared to the ability to stimulate effector T cells and/or NK cells.

IL2 variant polypeptides described herein may have a mutation (e.g., a deletion, addition, or substitution) of 1, 2, 3, 4, 5, 6, 7, 8, 9, 10, 11, 12, 13, 14, 15, 16, 17, 18, 19, 20, or more amino acid residues relative to wild type IL2.

IL2 variant polypeptides described herein may include an amino acid sequence that is at least about 50%, at least about 65%, at least about 70%, at least about 80%, at least about 85%, at least about 87%, at least about 90%, at least about 95%, at least about 97%, at least about 98%, or at least about 99% identical to wild type IL2.

In one embodiment, the IL2 variant polypeptides described herein have one or more, preferably all of the following properties:

1) Agonist action at IL2Rβγ. This property can be evaluated directly in in vitro proliferation assays with cell lines dependent on IL2.
2) Loss of capacity, as compared to wild type IL2, to stimulate in vitro and/or in vivo populations of regulatory T cells. This property can be assessed, for instance, by studying the ability of the muteins, as compared to those of wild type IL2, to induce expansion of regulatory T cells.
3) Increased therapeutic effect with respect to the native IL2 in animal models. This property can be assessed, for example, by comparing the antitumor or anti-metastatic effect of the IL2 variant polypeptides described herein and the wild type IL2 as monotherapy in transplantable tumor models (e.g. B16 melanoma). It can also be evaluated through the potentiating effect of the cellular and/or humoral response to a vaccine of interest.

Many immune cells transiently up-regulate IL2Rαβγ upon activation to increase IL2 sensitivity when mounting an immunological response, including priming of CD8 T cells. Since some IL2Rαβγ binding by IL2 may be necessary, the present invention envisions the use of a mixture of IL2Rβγ-selective IL2 variant polypeptides described herein in combination with IL2 (including functional variants thereof) that does not demonstrate preferential affinity towards IL2Rβγ, such as wild type IL2. In certain embodiments, the molar ratio of IL2Rβγ-selective IL2 variant polypeptides described herein to IL2 that does not demonstrate preferential affinity towards IL2Rβγ is from 50:1 to 1:1, 20:1 to 2:1, 10:1 to 5:1, or 5:1 to 3:1.

IL2 variant polypeptides described herein can be prepared as fusion or chimeric polypeptides that include an IL2 variant portion and a heterologous polypeptide (i.e., a polypeptide that is not IL2 or a variant thereof). The IL2 variants may be fused to an extended-PK group, which increases circulation half-life. Non-limiting examples of extended-PK groups are described infra. It should be understood that other PK groups that increase the circulation half-life of cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Immunoglobulin Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann, Expert Opin Biol Ther, 2016 July; 16(7):903-15 which is herein incorporated by reference in its entirety. As used herein, an "extended-PK IL" refers to an interleukin (IL) moiety (including an IL variant moiety) in combination with an extended-PK group. In one embodiment, the extended-PK IL is a fusion protein in which an IL moiety is linked or fused to an extended-PK group. An exemplary fusion protein is an HSA/IL2 fusion in which an IL2 moiety is fused with HSA.

In certain embodiments, the serum half-life of an extended-PK IL is increased relative to the IL alone (i.e., the IL not fused to an extended-PK group). In certain embodiments, the serum half-life of the extended-PK IL is at least 20, 40, 60, 80, 100, 120, 150, 180, 200, 400, 600, 800, or 1000% longer relative to the serum half-life of the IL alone. In certain embodiments, the serum half-life of the extended-PK IL is at least 1.5-fold, 2-fold, 2.5-fold, 3-fold, 3.5-fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the IL alone. In certain embodiments, the serum half-life of the extended-PK IL is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

In certain embodiments, the extended-PK group includes serum albumin, or fragments thereof or variants of the serum albumin or fragments thereof (all of which for the purpose of the present disclosure are comprised by the term "albumin"). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular IL2 (or variant thereof). The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In one embodiment, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off. In a most preferred embodiment, the "processed form of an albumin fusion protein" refers to an albumin fusion protein product which has undergone N-terminal signal peptide cleavage, herein also referred to as a "mature albumin fusion protein".

In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, mouse, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789.

The terms, human serum albumin (HSA) and human albumin (HA) are used interchangeably herein. The terms, "albumin and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the disclosure, albumin may be naturally occurring albumin or a fragment or variant thereof. Albumin may be human albumin and may be derived from any vertebrate, especially any mammal. In one embodiment, albumin comprises the amino acid sequence of SEQ ID NO: 23 or an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 23.

Preferably, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used. In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In another preferred embodiment, the therapeutic proteins fused at the N- and C-termini are different therapeutic proteins. In one embodiment, the different therapeutic proteins may be useful to treat or prevent the same or a related disease, disorder, or condition.

In one embodiment, the therapeutic protein(s) is (are) joined to the albumin through (a) peptide linker(s). A linker peptide between the fused portions may provide greater physical separation between the moieties and thus maximize the accessibility of the therapeutic protein portion, for instance, for binding to its cognate receptor. The linker peptide may consist of amino acids such that it is flexible or more rigid. The linker sequence may be cleavable by a protease or chemically.

As used herein, the term "Fc region" refers to the portion of a native immunoglobulin formed by the respective Fc domains (or Fc moieties) of its two heavy chains. As used herein, the term "Fc domain" refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term "Fc domain"). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species.

Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended-PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, which is herein incorporated by reference in its entirety. In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain aspects, the extended-PK IL, suitable for use according to the disclosure, can employ one or more peptide linkers. As used herein, the term "peptide linker" refers to a peptide or polypeptide sequence which connects two or more domains (e.g., the extended-PK moiety and an IL moiety such as IL2) in a linear amino acid sequence of a polypeptide chain. For example, peptide linkers may be used to connect an IL2 moiety to a HSA domain.

Linkers suitable for fusing the extended-PK group to e.g. IL2 are well known in the art. Exemplary linkers include glycine-serine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

In addition to, or in place of, the heterologous polypeptides described above, an IL2 variant polypeptide described herein can contain sequences encoding a "marker" or "reporter". Examples of marker or reporter genes include β-lactamase, chloramphenicol acetyltransferase (CAT), adenosine deaminase (ADA), aminoglycoside phosphotransferase, dihydrofolate reductase (DHFR), hygromycin-B-hosphotransferase (HPH), thymidine kinase (TK), β-galactosidase, and xanthine guanine phosphoribosyltransferase (XGPRT).

The IL2 variant polypeptides described herein may act on immune effector cells that may be present endogenously in a subject or following administration of the immune effector cells. Accordingly, immune effector cells may be provided to a subject by administration of immune effector cells, e.g., naïve or antigen receptor-transgenic immune effector cells. Particularly preferred "immune effector cells" are cells which, either naturally or following transfection with nucleic acid encoding one or more IL2R polypeptides, are responsive to IL2. Such responsiveness includes activation, differentiation, proliferation, survival and/or indication of one or more immune effector functions. The cells include, in particular, cytotoxic cells such as cells with lytic potential, in particular lymphoid cells, and are preferably T cells, in particular effector T cells, such as cytotoxic lymphocytes, preferably selected from cytotoxic T cells, natural killer (NK) cells, and lymphokine-activated killer (LAK) cells. Upon activation, these cells may trigger the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells. The cells used in connection with the present invention will preferably be autologous cells, although heterologous cells or allogenic cells can be used.

The term "effector functions" in the context of the present invention includes any functions mediated by components of the immune system that result, for example, in the killing of diseased cells such as tumor cells, or in the inhibition of tumor growth and/or inhibition of tumor development, including inhibition of tumor dissemination and metastasis. Preferably, the effector functions in the context of the present invention are T cell mediated effector functions. Such functions comprise in the case of a helper T cell (CD4$^+$ T cell) the release of cytokines and/or the activation of CD8$^+$ lymphocytes (CTLs) and/or B cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term "immune effector cell" or "immunoreactive cell" in the context of the present invention relates to a cell which exerts effector functions during an immune reaction. An "immune effector cell" in one embodiment is capable of binding an antigen such as an antigen presented in the context of MHC on a cell or expressed on the surface of a cell and mediating an immune response. For example, immune effector cells comprise T cells (cytotoxic T cells, helper T cells, tumor infiltrating T cells), B cells, natural killer cells, neutrophils, macrophages, and dendritic cells. Preferably, in the context of the present invention, "immune effector cells" are T cells, preferably CD4$^+$ and/or CD8$^+$ T cells. According to the invention, the term "immune effector cell" also includes a cell which can mature into an immune cell (such as T cell, in particular T helper cell, or cytolytic T cell) with suitable stimulation. Immune effector cells comprise CD34$^+$ hematopoietic stem cells, immature and mature T cells and immature and mature B cells. The differentiation of T cell precursors into a cytolytic T cell, when exposed to an antigen, is similar to clonal selection of the immune system.

Preferably, an "immune effector cell" recognizes an antigen with some degree of specificity, in particular if presented in the context of MHC or present on the surface of diseased cells such as cancer cells. Preferably, said recognition enables the cell that recognizes an antigen to be responsive or reactive. If the cell is a helper T cell (CD4$^+$ T cell) such responsiveness or reactivity may involve the release of cytokines and/or the activation of CD8$^+$ lymphocytes (CTLs) and/or B cells. If the cell is a CTL such responsiveness or reactivity may involve the elimination of cells, i.e., cells characterized by expression of an antigen, for example, via apoptosis or perforin-mediated cell lysis. According to the invention, CTL responsiveness may include sustained calcium flux, cell division, production of cytokines such as IFN-$\gamma$ and TNF-$\alpha$, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen and are responsive or reactive are also termed "antigen-responsive CTL" herein.

In one embodiment, the immune effector cells are antigen receptor (e.g., chimeric antigen receptor (CAR) or T cell receptor (TCR)) expressing immune effector cells. In one embodiment, the immune effector cells are CAR-expressing immune effector cells. In one embodiment, the immune effector cells are TCR-expressing immune effector cells. In one embodiment, the immune effector cells are antigen receptor (e.g., chimeric antigen receptor (CAR) or T cell receptor (TCR)) transgenic immune effector cells.

The immune effector cells to be used according to the invention may express an endogenous antigen receptor such as T cell receptor or B cell receptor or may lack expression of an endogenous antigen receptor.

A "lymphoid cell" is a cell which, optionally after suitable modification, e.g. after transfer of an antigen receptor such as a TCR or a CAR, is capable of producing an immune response such as a cellular immune response, or a precursor cell of such cell, and includes lymphocytes, preferably T lymphocytes, lymphoblasts, and plasma cells. A lymphoid cell may be an immune effector cell as described herein. A preferred lymphoid cell is a T cell which can be modified to express an antigen receptor on the cell surface. In one embodiment, the lymphoid cell lacks endogenous expression of a T cell receptor.

The terms "T cell" and "T lymphocyte" are used interchangeably herein and include T helper cells (CD4$^+$ T cells) and cytotoxic T cells (CTLs, CD8$^+$ T cells) which comprise cytolytic T cells. The term "antigen-specific T cell" or similar terms relate to a T cell which recognizes the antigen to which the T cell is targeted and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as IFN-$\gamma$) can be measured.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4$^+$ T cells because they express the CD4 glycoprotein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8$^+$ T cells since they express the CD8 glycoprotein on their surface. These cells recognize their targets by binding to antigen associated with MHC class I, which is present on the surface of nearly every cell of the body.

As used herein the term "effector T cell" or "Teff" refers to T cells which are not regulatory and includes T helper cells and cytotoxic T cells. Furthermore, the term "effector T cell" or "Teff" includes activated T cells and non-activated T cells and thus, cells which have encountered antigen and/or costimulatory molecules as well as cells which have not encountered antigen and/or costimulatory molecules. Thus, the term "effector T cell" also includes naïve T cells. T cells express CD25 when they are activated. According to the invention, effector T cells may be CD25$^+$ T cells or CD25$^-$ T cells, and are preferably CD25$^-$ T cells.

"Regulatory T cells", "T$_{reg}$ cells" or "Tregs" are a subpopulation of T cells that modulate the immune system, maintain tolerance to self-antigens, and prevent autoimmune disease. Tregs are immunosuppressive and generally suppress or downregulate induction and proliferation of effector T cells. Tregs express the biomarkers CD4, FoxP3, and CD25.

As used herein, the term "naïve T cell" refers to mature T cells that, unlike activated or memory T cells, have not encountered their cognate antigen within the periphery. Naïve T cells are commonly characterized by the surface expression of L-selectin (CD62L), the absence of the activation markers CD25, CD44 or CD69 and the absence of the memory CD45RO isoform.

As used herein, the term "memory T cells" refers to a subgroup or subpopulation of T cells that have previously encountered and responded to their cognate antigen. At a second encounter with the antigen, memory T cells can reproduce to mount a faster and stronger immune response than the first time the immune system responded to the antigen. Memory T cells may be either CD4$^+$ or CD8$^+$ and usually express CD45RO.

All T cells have a T cell receptor (TCR) existing as a complex of several proteins. In the majority of T cells, the actual T cell receptor is composed of two separate peptide chains, which are produced from the independent T cell receptor alpha and beta (TCR$\alpha$ and TCR$\beta$) genes and are called $\alpha$- and $\beta$-TCR chains. A much less common (2% of total T cells) group of T cells, the $\gamma\delta$ T cells (gamma delta T cells) possess a distinct T cell receptor (TCR) on their surface, which is made up of one $\gamma$-chain and one $\delta$-chain.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4$^-$CD8$^-$) cells. As they progress through their development they become double-positive thymocytes (CD4$^+$ CD8$^+$), and finally mature to single-positive (CD4$^+$CD8$^-$ or CD4$^-$ CD8$^+$) thymocytes that are then released from the thymus to peripheral tissues.

T cells may generally be prepared in vitro or ex vivo, using standard procedures. For example, T cells may be isolated from bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A sample comprising T cells may, for example, be peripheral blood mononuclear cells (PBMC).

As used herein, the term "NK cell" or "Natural Killer cell" refers to a subset of peripheral blood lymphocytes defined by the expression of CD56 or CD16 and the absence of the T cell receptor. As provided herein, the NK cell can also be differentiated from a stem cell or progenitor cell.

Immune effector cells may express naturally or following modification (e.g., ex vivo/in vitro or in vivo in a subject to be treated) an IL2R or IL2R variant. Further, immune effector cells may express naturally or following modification (e.g., ex vivo/in vitro or in vivo in a subject to be treated) an antigen receptor such as a T cell receptor (TCR) or chimeric antigen receptor (CAR) binding antigen or a procession product thereof, in particular when present on or presented by a target cell.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered (genetically modified) to express CARs specifically directed towards antigens on the patient's tumor cells, then infused back into the patient.

The term "CAR" (or "chimeric antigen receptor") is synonymous with the terms "chimeric T cell receptor" and "artificial T cell receptor" and relates to an artificial receptor comprising a single molecule or a complex of molecules which recognizes, i.e. binds to, a target structure (e.g. an antigen) on a target cell such as a cancer cell (e.g. by binding of an antigen binding domain to an antigen expressed on the surface of the target cell) and may confer specificity onto an immune effector cell such as a T cell expressing said CAR on the cell surface. Preferably, recognition of the target structure by a CAR results in activation of an immune effector cell expressing said CAR. A CAR may comprise one or more protein units said protein units comprising one or more domains as described herein. The term "CAR" does not include T cell receptors.

A CAR comprises a target-specific binding element otherwise referred to as an antigen binding moiety or antigen binding domain that is generally part of the extracellular domain of the CAR. The antigen binding domain recognizes a ligand that acts as a cell surface marker on target cells associated with a particular disease state. Specifically, the CAR targets the antigen such as tumor antigen on a diseased cell such as tumor cell.

In one embodiment, the binding domain in the CAR binds specifically to the antigen. In one embodiment, the antigen to which the binding domain in the CAR binds is expressed in a cancer cell (tumor antigen). In one embodiment, the antigen is expressed on the surface of a cancer cell. In one embodiment, the binding domain binds to an extracellular domain or to an epitope in an extracellular domain of the antigen. In one embodiment, the binding domain binds to native epitopes of the antigen present on the surface of living cells.

In one embodiment, an antigen binding domain comprises a variable region of a heavy chain of an immunoglobulin (VH) with a specificity for the antigen and a variable region of a light chain of an immunoglobulin (VL) with a specificity for the antigen. In one embodiment, an immunoglobulin is an antibody. In one embodiment, said heavy chain variable region (VH) and the corresponding light chain variable region (VL) are connected via a peptide linker. Preferably, the antigen binding moiety portion in the CAR is a scFv.

The CAR is designed to comprise a transmembrane domain that is fused to the extracellular domain of the CAR. In one embodiment, the transmembrane domain is not naturally associated with one of the domains in the CAR. In one embodiment, the transmembrane domain is naturally associated with one of the domains in the CAR. In one embodiment, the transmembrane domain is modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions of particular use in this invention may be derived from (i.e. comprise at least the transmembrane region(s) of) the alpha, beta or zeta chain of the T cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain.

In some instances, the CAR of the invention comprises a hinge domain which forms the linkage between the transmembrane domain and the extracellular domain.

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

In one embodiment, the CAR comprises a primary cytoplasmic signaling sequence derived from CD3-zeta. Further, the cytoplasmic domain of the CAR may comprise the CD3-zeta signaling domain combined with a costimulatory signaling region.

The identity of the co-stimulation domain is limited only in that it has the ability to enhance cellular proliferation and survival upon binding of the targeted moiety by the CAR. Suitable co-stimulation domains include CD28, CD137 (4-1BB), a member of the tumor necrosis factor receptor (TNFR) superfamily, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+CD137 (4-1BB) and CD28+CD134 (OX40).

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the CAR comprises a signal peptide which directs the nascent protein into the endoplasmic reticulum. In one embodiment, the signal peptide precedes the antigen binding domain. In one embodiment, the signal peptide is derived from an immunoglobulin such as IgG.

The term "antibody" includes an immunoglobulin comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody binds, preferably specifically binds with an antigen. Antibodies can be intact immunoglobulins derived from natural sources or from recombinant sources and can be immunoreactive portions or fragments of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab')$_2$, as well as single chain antibodies and humanized antibodies (Harlow et al., 1999, In: Using Antibodies: A Laboratory Manual, Cold Spring Harbor Laboratory Press, NY; Harlow et al., 1989, in: Antibodies: A Laboratory Manual, Cold Spring Harbor, New York; Houston et al., 1988, Proc. Natl. Acad. Sci. USA 85:5879-5883; Bird et al., 1988, Science 242:423-426).

Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, K, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The term "antibody fragment" refers to a portion of an intact antibody and typically comprises the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain", as used herein, refers to the larger of the two types of polypeptide chains present in antibody molecules in their naturally occurring conformations.

An "antibody light chain", as used herein, refers to the smaller of the two types of polypeptide chains present in antibody molecules in their naturally occurring conformations, K and A light chains refer to the two major antibody light chain isotypes.

According to the disclosure, a CAR which when present on a T cell recognizes an antigen such as on the surface of antigen presenting cells or diseased cells such as cancer cells, such that the T cell is stimulated, and/or expanded or exerts effector functions as described above.

A variety of methods may be used to introduce IL2 receptor polypeptides and/or antigen receptors such as CAR constructs into cells such as T cells to produce cells genetically modified to express the IL2 receptor polypeptides and/or antigen receptors. Such methods including non-viral-based DNA transfection, non-viral-based RNA transfection, e.g., mRNA transfection, transposon-based systems, and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems. In one embodiment of all aspects of the invention, cells are transfected either ex vivo or in vivo with nucleic acid encoding the IL2 receptor polypeptide and/or nucleic acid encoding the antigen receptor. In one embodiment, a combination of ex vivo and in vivo transfection may be used. Following ex vivo modification, cells may be administered to a subject being treated.

In one embodiment of all aspects of the invention, the cells described herein may be autologous, allogeneic or syngeneic to the subject to be treated. In one embodiment, the present disclosure envisions the removal of cells from a patient and the subsequent re-delivery of the (e.g., ex vivo modified and/or expanded) cells to the patient. In one embodiment, the present disclosure does not envision the removal of cells from a patient. In the latter case all steps of genetic modification of cells are performed in vivo.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The present disclosure also provides for the provision, e.g., administration, of an antigen molecule such as a peptide or protein antigen, for example to contact immune effector cells, in particular immune effector cells expressing an antigen receptor, e.g., immune effector cells which are genetically manipulated to express an antigen receptor, either ex vivo or in the subject being treated, with a cognate antigen molecule, wherein the antigen molecule or a procession product thereof, e.g., a fragment thereof, binds to the antigen receptor such as TCR or CAR carried by the immune effector cells. In one embodiment, the cognate antigen molecule is selected from the group consisting of the antigen expressed by a target cell to which the immune effector cells are targeted or a fragment thereof, or a variant of the antigen or the fragment. In one embodiment, the immune effector cells are contacted with the cognate antigen molecule under conditions such that expansion and/or activation of the immune effector cells occurs. In one embodiment, the step of contacting the immune effector cells with the cognate antigen molecule takes place in vivo or ex vivo.

The peptide and protein antigens suitable for use according to the disclosure typically include a peptide or protein comprising an epitope for inducing an immune response. The peptide or protein or epitope may be derived from a target antigen, i.e. the antigen against which an immune response is to be elicited. For example, the peptide or protein antigen or the epitope contained within the peptide or protein antigen may be a target antigen or a fragment or variant of a target antigen.

In one embodiment, the methods described herein comprise the step of administering the antigen molecule or a nucleic acid coding therefor to the subject. In one embodiment, the nucleic acid encoding the antigen molecule is expressed in cells of the subject to provide the antigen molecule. In one embodiment, expression of the antigen molecule is at the cell surface. In one embodiment, the antigen molecule is presented in the context of MHC. In one embodiment, the nucleic acid encoding the antigen molecule is transiently expressed in cells of the subject. In one embodiment, the nucleic encoding the antigen molecule is RNA. In one embodiment, the antigen molecule or the nucleic acid coding therefor is administered systemically. In one embodiment, after systemic administration of the nucleic acid encoding the antigen molecule, expression of the nucleic acid encoding the antigen molecule in spleen occurs. In one embodiment, after systemic administration of the nucleic acid encoding the antigen molecule, expression of the nucleic acid encoding the antigen molecule in antigen presenting cells, preferably professional antigen presenting cells occurs. In one embodiment, the antigen presenting cells are selected from the group consisting of dendritic cells, macrophages and B cells. In one embodiment, after systemic administration of the nucleic acid encoding the antigen molecule, no or essentially no expression of the nucleic acid encoding the antigen molecule in lung and/or liver occurs. In one embodiment, after systemic administration of the nucleic acid encoding the antigen molecule, expression of the nucleic acid encoding the antigen molecule in spleen is at least 5-fold the amount of expression in lung.

A peptide and protein antigen which is provided to a subject according to the invention (either by administering the peptide and protein antigen or a nucleic acid, in particular RNA, encoding the peptide and protein antigen), i.e., a vaccine antigen, preferably results in stimulation, priming and/or expansion of immune effector cells in the subject being administered the peptide or protein antigen or nucleic acid. Said stimulated, primed and/or expanded immune effector cells are preferably directed against a target antigen, in particular a target antigen expressed by diseased cells, tissues and/or organs, i.e., a disease-associated antigen. Thus, a vaccine antigen may comprise the disease-associated antigen, or a fragment or variant thereof. In one embodiment, such fragment or variant is immunologically equivalent to the disease-associated antigen. In the context of the present disclosure, the term "fragment of an antigen" or "variant of an antigen" means an agent which results in stimulation, priming and/or expansion of immune effector cells which stimulated, primed and/or expanded immune effector cells target the antigen, i.e. a disease-associated antigen, in particular when presented by diseased cells, tissues and/or organs. Thus, the vaccine antigen may correspond to or may comprise the disease-associated antigen, may correspond to or may comprise a fragment of the disease-associated antigen or may correspond to or may comprise an antigen which is homologous to the disease-associated antigen or a fragment thereof. If the vaccine antigen comprises a fragment of the disease-associated antigen or an amino acid sequence which is homologous to a fragment of the disease-associated antigen said fragment or amino acid sequence may comprise an epitope of the disease-associated antigen or a sequence which is homologous to an epitope of the disease-associated antigen. Thus, according to the disclosure, a vaccine antigen may comprise an immunogenic fragment of a disease-associated antigen or an amino acid sequence being homologous to an immunogenic fragment of a disease-associated antigen. An "immunogenic fragment of an antigen" according to the disclosure preferably relates to a fragment of an antigen which is capable of stimulating, priming and/or expanding immune effector cells carrying an antigen receptor binding to the antigen or cells expressing the antigen. It is preferred that the vaccine antigen (similar to the disease-associated antigen) provides the relevant epitope for binding by the antigen binding domain present in the immune effector cells. In one embodiment, the vaccine antigen (similar to the disease-associated antigen) is expressed on the surface of a cell such as an antigen-presenting cell so as to provide the relevant epitope for binding by immune effector cells. The vaccine antigen may be a recombinant antigen.

In one embodiment of all aspects of the invention, the nucleic acid encoding the vaccine antigen is expressed in cells of a subject to provide the antigen or a procession product thereof for binding by the antigen receptor expressed by immune effector cells, said binding resulting in stimulation, priming and/or expansion of the immune effector cells.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject such as T cells binding to the reference amino acid sequence or cells expressing the reference amino acid sequence induces an immune reaction having a specificity of reacting with the reference amino acid sequence. Thus, a molecule which is immunologically equivalent to an antigen exhibits the same or essentially the same properties and/or exerts the same or essentially the same effects regarding stimulation, priming and/or expansion of T cells as the antigen to which the T cells are targeted.

"Activation" or "stimulation", as used herein, refers to the state of an immune effector cell such as T cell that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

The term "antigen" relates to an agent comprising an epitope against which an immune response can be generated. The term "antigen" includes, in particular, proteins and peptides. In one embodiment, an antigen is presented or present on the surface of cells of the immune system such as antigen presenting cells like dendritic cells or macrophages. An antigen or a procession product thereof such as a T cell epitope is in one embodiment bound by an antigen receptor. Accordingly, an antigen or a procession product thereof may react specifically with immune effector cells such as T-lymphocytes (T cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells. A tumor antigen is typically expressed preferentially by cancer cells (e.g., it is expressed at higher levels in cancer cells than in non-cancer cells) and in some instances it is expressed solely by cancer cells. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A 11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, pI90 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "expressed on the cell surface" or "associated with the cell surface" means that a molecule such as a receptor or antigen is associated with and located at the plasma membrane of a cell, wherein at least a part of the molecule faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a molecule associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules.

The term "extracellular portion" or "exodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The term "epitope" refers to a part or fragment of a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

In one embodiment, the target antigen is a tumor antigen and the peptide or protein comprising an epitope or a fragment thereof (e.g., an epitope) is derived from the tumor antigen. The tumor antigen may be a "standard" antigen, which is generally known to be expressed in various cancers. The tumor antigen may also be a "neo-antigen", which is specific to an individual's tumor and has not been previously recognized by the immune system. A neo-antigen or neo-epitope may result from one or more cancer-specific mutations in the genome of cancer cells resulting in amino acid changes. If the tumor antigen is a neo-antigen, the peptide or protein comprising an epitope preferably comprises an epitope or a fragment of said neo-antigen comprising one or more amino acid changes.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a "pentatope") and RNA that encodes at least ten epitopes (termed a "decatope").

According to the various aspects of the invention, the aim is preferably to provide an immune response against cancer cells expressing a tumor antigen and to treat a cancer disease involving cells expressing a tumor antigen. Preferably the invention involves the administration of immune effector cells such as T cells targeted against cancer cells expressing a tumor antigen and/or vaccine antigen recognized by such cells.

The peptide and protein antigen can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T cell responses to the peptide or protein.

In one embodiment, vaccine antigen is recognized by an immune effector cell. Preferably, the vaccine antigen if recognized by an immune effector cell is able to induce in the presence of appropriate co-stimulatory signals, stimulation, priming and/or expansion of the immune effector cell carrying an antigen receptor recognizing the vaccine antigen. In the context of the embodiments of the present invention, the vaccine antigen is preferably presented or present on the surface of a cell, preferably an antigen presenting cell. Recognition of a disease-associated antigen on the surface of a diseased cell by the immune effector cells may result in an immune reaction against the antigen (or cell expressing the antigen).

In certain embodiments, immune checkpoint inhibitors are used in combination with other therapeutic agents described herein (e.g., RNA encoding an interleukin (IL)-2 variant polypeptide and optionally RNA encoding a peptide or protein comprising an epitope).

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint inhibitor" refers to a molecule that totally or partially reduces, inhibits, interferes with or modulates one or more checkpoint proteins. In certain embodiments, the immune checkpoint inhibitor prevents inhibitory signals associated with the immune checkpoint. In certain embodiments, the immune checkpoint inhibitor is an antibody, or fragment thereof that disrupts inhibitory signaling associated with the immune checkpoint. In certain embodiments, the immune checkpoint inhibitor is a small molecule that disrupts inhibitory signaling. In certain embodiments, the immune checkpoint inhibitor is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint inhibitor is an antibody, or fragment thereof, that prevents the interaction between CTLA-4 and CD80 or CD86. In certain embodiments, the immune checkpoint inhibitor is an antibody, or fragment thereof, that prevents the interaction between LAG3 and its ligands, or TIM-3 and its ligands. The checkpoint inhibitor may also be in the form of the soluble form of the molecules (or variants thereof) themselves, e.g., a soluble PD-L1 or PD-L1 fusion.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1.

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1.

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4.

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope.

"T Cell Membrane Protein-3 (TIM3)" is an inhibitory receptor involved in the inhibition of lymphocyte activity by inhibition of TH1 cell responses. Its ligand is galectin 9, which is upregulated in various types of cancers. The term "TIM3" as used herein includes human TIM3 (hTIM3), variants, isoforms, and species homologs of hTIM3, and analogs having at least one common epitope.

The "B7 family" refers to inhibitory ligands with undefined receptors. The B7 family encompasses B7-H3 and B7-H4, both upregulated on tumor cells and tumor infiltrating cells.

In certain embodiments, the immune checkpoint inhibitor suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

In certain embodiments, the immune checkpoint inhibitor is an antibody or an antigen-binding portion thereof, that disrupts or inhibits signaling from an inhibitory immunoregulator. In certain embodiments, the immune checkpoint inhibitor is a small molecule that disrupts or inhibits signaling from an inhibitory immunoregulator.

In certain embodiments, the inhibitory immunoregulator is a component of the PD-1/PD-L1 signaling pathway. Accordingly, certain embodiments of the disclosure provide for administering to a subject an antibody or an antigen-binding portion thereof that disrupts the interaction between the PD-1 receptor and its ligand, PD-L1. Antibodies which bind to PD-1 and disrupt the interaction between the PD-1 and its ligand, PD-L1, are known in the art. In certain embodiments, the antibody or antigen-binding portion thereof binds specifically to PD-1. In certain embodiments, the antibody or antigen-binding portion thereof binds specifically to PD-L1 and inhibits its interaction with PD-1, thereby increasing immune activity.

In certain embodiments, the inhibitory immunoregulator is a component of the CTLA4 signaling pathway. Accordingly, certain embodiments of the disclosure provide for administering to a subject an antibody or an antigen-binding portion thereof that targets CTLA4 and disrupts its interaction with CD80 and CD86.

In certain embodiments, the inhibitory immunoregulator is a component of the LAG3 (lymphocyte activation gene 3) signaling pathway. Accordingly, certain embodiments of the disclosure provide for administering to a subject an antibody or an antigen-binding portion thereof that targets LAG3 and disrupts its interaction with MHC class II molecules.

In certain embodiments, the inhibitory immunoregulator is a component of the B7 family signaling pathway. In certain embodiments, the B7 family members are B7-H3 and B7-H4. Accordingly, certain embodiments of the disclosure provide for administering to a subject an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity.

In certain embodiments, the inhibitory immunoregulator is a component of the TIM3 (T cell membrane protein 3) signaling pathway. Accordingly, certain embodiments of the disclosure provide for administering to a subject an antibody or an antigen-binding portion thereof that targets TIM3 and disrupts its interaction with galectin 9.

It will be understood by one of ordinary skill in the art that other immune checkpoint targets can also be targeted by antagonists or antibodies, provided that the targeting results in the stimulation of an immune response such as an anti-tumor immune response as reflected in, e.g., an increase in T cell proliferation, enhanced T cell activation, and/or increased cytokine production (e.g., IFN-γ, IL2).

It is particularly preferred according to the invention that the peptides, proteins or polypeptides described herein, in particular the IL2 variant polypeptides and/or vaccine antigens, are administered in the form of RNA encoding the peptides, proteins or polypeptides described herein. In one embodiment, different peptides, proteins or polypeptides described herein are encoded by different RNA molecules.

In one embodiment, the RNA is formulated in a delivery vehicle. In one embodiment, the delivery vehicle comprises particles. In one embodiment, the delivery vehicle comprises at least one lipid. In one embodiment, the at least one lipid comprises at least one cationic lipid. In one embodiment, the lipid forms a complex with and/or encapsulates the RNA. In one embodiment, the lipid is comprised in a vesicle encapsulating the RNA. In one embodiment, the RNA is formulated in liposomes.

According to the disclosure, after administration of the RNA described herein, at least a portion of the RNA is delivered to a target cell. In one embodiment, at least a portion of the RNA is delivered to the cytosol of the target cell. In one embodiment, the RNA is translated by the target cell to produce the encoded peptide or protein.

Some aspects of the disclosure involve the targeted delivery of the RNA disclosed herein (RNA encoding an IL2 variant polypeptide and/or RNA encoding a peptide or protein comprising an epitope).

In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding a peptide or protein comprising an epitope.

In one embodiment, the target cell is a spleen cell. In one embodiment, the target cell is an antigen presenting cell such as a professional antigen presenting cell in the spleen. In one embodiment, the target cell is a dendritic cell in the spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naïve lymphocytes and initiate an adaptive immune response.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl or diacyl chain, and the head group of the lipid typically carries the positive charge. Examples of cationic lipids include, but are not limited to 1,2-di-O-octadecenyl-3-trimethylammonium propane (DOTMA), dimethyldioctadecylammonium (DDAB); 1,2-dioleoyl-3-trimethylammonium propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-I-propanamium trifluoroacetate (DOSPA). Preferred are DOTMA, DOTAP, DODAC, and DOSPA. In specific embodiments, the cationic lipid is DOTMA and/or DOTAP.

An additional lipid may be incorporated to adjust the overall positive to negative charge ratio and physical stability of the RNA lipoplex particles. In certain embodiments, the additional lipid is a neutral lipid. As used herein, a "neutral lipid" refers to a lipid having a net charge of zero. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, cholesterol, and cerebroside. In specific embodiments, the additional lipid is DOPE, cholesterol and/or DOPC.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 nm to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol)*(the total number of negative charges in RNA)].

The spleen targeting RNA lipoplex particles described herein at physiological pH preferably have a net negative charge such as a charge ratio of positive charges to negative charges from about 1.9:2 to about 1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0.

RNA delivery systems have an inherent preference to the liver. This pertains to lipid-based particles, cationic and neutral nanoparticles, in particular lipid nanoparticles such as liposomes, nanomicelles and lipophilic ligands in bioconjugates. Liver accumulation is caused by the discontinuous nature of the hepatic vasculature or the lipid metabolism (liposomes and lipid or cholesterol conjugates).

In one embodiment of the targeted delivery of an IL2 variant polypeptide described herein, the target organ is liver and the target tissue is liver tissue. The delivery to such target tissue is preferred, in particular, if presence of the IL2 variant polypeptide in this organ or tissue is desired and/or if it is desired to express large amounts of the IL2 variant polypeptide and/or if systemic presence of the IL2 variant polypeptide, in particular in significant amounts, is desired or required.

In one embodiment, RNA encoding an IL2 variant polypeptide is administered in a formulation for targeting liver. Such formulations are described herein above.

For in vivo delivery of RNA to the liver, a drug delivery system may be used to transport the RNA into the liver by preventing its degradation. For example, polyplex nanomicelles consisting of a poly(ethylene glycol) (PEG)-coated surface and an mRNA-containing core is a useful system because the nanomicelles provide excellent in vivo stability of the RNA, under physiological conditions. Furthermore, the stealth property provided by the polyplex nanomicelle surface, composed of dense PEG palisades, effectively evades host immune defenses.

The peptides, proteins, polypeptides, RNA, RNA particles, immune effector cells and further agents, e.g., immune checkpoint inhibitors, described herein may be administered in pharmaceutical compositions or medicaments for therapeutic or prophylactic treatments and may be administered in the form of any suitable pharmaceutical composition which may comprise a pharmaceutically acceptable carrier and may optionally comprise one or more adjuvants, stabilizers etc. In one embodiment, the pharmaceutical composition is for therapeutic or prophylactic treatments, e.g., for use in treating or preventing a disease involving an antigen such as a cancer disease such as those described herein.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. In the context of the present disclosure, the pharmaceutical composition comprises peptides, proteins, polypeptides, RNA, RNA particles, immune effector cells and/or further agents as described herein.

The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The cytokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration. In one embodiment of all aspects of the invention, RNA encoding an IL2 variant polypeptide described herein and optionally RNA encoding an antigen is administered systemically.

The term "co-administering" as used herein means a process whereby different compounds or compositions (e.g., RNA encoding an IL2 variant polypeptide, RNA encoding a peptide or protein comprising an epitope and optionally an immune checkpoint inhibitor) are administered to the same patient. The RNA encoding an IL2 variant polypeptide and the RNA encoding a peptide or protein comprising an epitope may be administered simultaneously, at essentially the same time, or sequentially.

If administration takes place sequentially, the RNA encoding an IL2 variant polypeptide may be administered before or after administration of the RNA encoding a peptide or protein comprising an epitope. If administration takes place simultaneously the RNA encoding an IL2 variant polypeptide and the RNA encoding a peptide or protein comprising an epitope need not be administered within the same composition. The RNA encoding an IL2 variant polypeptide and the RNA encoding a peptide or protein comprising an epitope may be administered one or more times and the number of administrations of each component may be the same or different. In addition, the RNA encoding an IL2 variant polypeptide and the RNA encoding a peptide or protein comprising an epitope need not be administered at the same site.

The IL2 variant polypeptides, the polynucleotides encoding IL2 variant polypeptides, the host cells comprising the polynucleotide encoding the IL2 variant polypeptide, the pharmaceutical compositions and the methods of treatment described herein may be used in the therapeutic or prophylactic treatment of various diseases, in particular diseases in which provision of IL2, specifically of the IL2 variant polypeptides described herein, to a subject results in a therapeutic or prophylactic effect, such as cancer, autoimmune diseases, infectious diseases, vaccine adjuvant in cancer vaccine and conventional vaccine therapy, for immune stimulation in the elderly or otherwise immunocompromised individuals, as well as in HIV or human SCID patients, or other therapeutic application requiring general stimulation of the immune system in any suitable animal, preferably a mammal, most preferably human. IL2 has many effects. Some of these are stimulation of T cells, in particular memory T cells, naïve T cells and/or effector T cells, and/or NK cells. IL2 variant polypeptides described herein will have activities on cell types expressing only the intermediate affinity IL2 receptor, such as memory T cells, naïve T cells and/or effector T cells, but not the high affinity IL2 receptor, such as regulatory T cells. Accordingly, contemplated is use of the IL2 variant polypeptides, the polynucleotides encoding IL2 variant polypeptides, the host cells comprising the polynucleotide encoding the IL2 variant polypeptide, the pharmaceutical compositions and the methods of treatment described herein in the treatment of those diseases in which IL2 is expected to provide an effective therapy due to its T cell activity.

Alternatively, or in addition to methods of direct administration to patients, in some embodiments, IL2 variant polypeptides can be used in ex vivo methods. For example, cells (e.g., peripheral blood lymphocytes or purified populations of lymphocytes isolated from a patient and placed or maintained in culture) can be cultured in vitro in culture medium and the contacting step can be effected by adding the IL2 variant polypeptides, and/or polynucleotides encoding them to the culture medium. The culture step can include further steps in which the cells are stimulated or treated with other agents, e.g., to stimulate proliferation, or to expand a population of cells that is reactive to an antigen of interest (e.g., a cancer antigen or a viral antigen). The cells are then administered to the patient after they have been treated.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against diseased cells expressing an antigen such as cancer cells expressing a tumor antigen, and to treat a disease such as a cancer disease involving cells expressing an antigen such as a tumor antigen.

A pharmaceutical composition comprising RNA encoding a peptide or protein comprising an epitope may be administered to a subject to elicit an immune response against an antigen comprising said epitope in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response. A cellular immune response includes, without limitation, a cellular response directed to cells expressing an antigen and being characterized by presentation of an antigen with class I or class II MHC molecule. The cellular response relates to T lymphocytes, which may be classified as helper T cells (also termed CD4+ T cells) that play a central role by regulating the immune response or killer cells (also termed cytotoxic T cells, CD8+ T cells, or CTLs) that induce apoptosis in infected cells or cancer cells. In one embodiment, administering a pharmaceutical composition of the present disclosure involves stimulation of an anti-tumor CD8+ T cell response against cancer cells expressing one or more tumor antigens. In as specific embodiment, the tumor antigens are presented with class I MHC molecule.

"Cell-mediated immunity", "cellular immunity", "cellular immune response", or similar terms are meant to include a cellular response directed to cells characterized by expression of an antigen, in particular characterized by presentation of an antigen with class I or class II MHC. The cellular response relates to cells called T cells or T lymphocytes which act as either "helpers" or "killers". The helper T cells (also termed CD4$^+$ T cells) play a central role by regulating the immune response and the killer cells (also termed cytotoxic T cells, cytolytic T cells, CD8$^+$ T cells or CTLs) kill diseased cells such as cancer cells, preventing the production of more diseased cells.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

The peptides, proteins, polypeptides, RNA, RNA particles and further agents, e.g., immune checkpoint inhibitors, described herein may be used in the therapeutic or prophylactic treatment of diseases in which provision of a peptide or protein comprising an epitope for inducing an immune response against an antigen in a subject to said subject results in a therapeutic or prophylactic effect. For example, provision of an antigen or epitope which is derived from a virus may be useful in the treatment of a viral disease caused by said virus. Provision of a tumor antigen or epitope may be useful in the treatment of a cancer disease wherein cancer cells express said tumor antigen.

In one embodiment, the present disclosure envisions embodiments wherein RNA formulations such as RNA lipoplex particles as described herein targeting spleen tissue are administered. The RNA encodes, for example, a peptide or protein comprising an epitope as described, for example, herein. The RNA is taken up by antigen-presenting cells in the spleen such as dendritic cells to express the peptide or protein. Following optional processing and presentation by the antigen-presenting cells an immune response may be generated against the epitope resulting in a prophylactic and/or therapeutic treatment of a disease involving the epitope or an antigen comprising the epitope. In one embodiment, the immune response induced by the RNA described herein comprises presentation of an antigen or fragment thereof, such as an epitope, by antigen presenting cells, such as dendritic cells and/or macrophages, and activation of cytotoxic T cells due to this presentation. For example, peptides or proteins encoded by the RNAs or procession products thereof may be presented by major histocompatibility complex (MHC) proteins expressed on antigen presenting cells. The MHC peptide complex can then be recognized by immune cells such as T cells or B cells leading to their activation.

Accordingly, the present disclosure relates to RNA as described herein for use in a prophylactic and/or therapeutic treatment of a disease involving an antigen, preferably a cancer disease.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" or "disease involving an epitope" refers to any disease which implicates an antigen or epitope, e.g. a disease which is characterized by the presence of an antigen or epitope. The disease involving an antigen or epitope can be an infectious disease, or a cancer disease or simply cancer. As mentioned above, the antigen may be a disease-associated antigen, such as a tumor-associated antigen, a viral antigen, or a bacterial antigen and the epitope may be derived from such antigen. In one embodiment, a disease involving an antigen is a disease involving cells expressing an antigen, preferably on the cell surface.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. *chlamydia* or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the disclosure also comprises cancer metastases.

Combination strategies in cancer treatment may be desirable due to a resulting synergistic effect, which may be considerably stronger than the impact of a monotherapeutic approach. In one embodiment, the pharmaceutical composition is administered with an immunotherapeutic agent. As used herein "immunotherapeutic agent" relates to any agent that may be involved in activating a specific immune response and/or immune effector function(s). Examples of immunotherapeutic agents include vaccines such as T cell vaccines, immune effector cells, or a combination thereof. The present disclosure also contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (ILIβ), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin α5β1), Votumumab (tumor antigen CTAA 16.88), Zalutumumab (EGFR), and Zanolimumab (CD4).

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Construct Design and mRNA Production

In order to design variants of human IL2 (hIL2) that combine decreased binding to and activation of hIL2Rα

(CD25) with increased binding to and activation of hIL2Rβ (CD122) we introduced various mutations in the hIL2Rβ binding site of hIL2 mutein A4, which is described with reduced CD25 binding. Besides the amino acid substitutions K43E and E61K, which are the defining mutations of hIL2 mutein A4, the following additional mutations were introduced in the mature domain of hIL2:

hIL2_A4s: L80F, R81D, L85V, I86V, I92F
hIL2_A4s1: L80F, R81E, L85V, I86V, I92F
hIL2_A4s2: L80F, R81E, L85V, I86V, I92W
hIL2_A4s3: L80F, R81E, I92F
hIL2_A4s4: L80F, R81D, I92F
hIL2_A4s6: Q74H, L80F, R81E, I92F
hIL2_A4s7: Q74H, L80F, R81E, I92W
hIL2_A4s8: Q74H, L80F, R81E, L85V, I92F

Cytokine encoding mRNAs for in vitro transcription were based on the pST1-T7-AGA-dEarl-hAg-MCS-FI-A30LA70 plasmid-backbone and derivative DNA-constructs. These plasmid constructs contain a 5' UTR (untranslated region, a derivative of the 5'-UTR of *Homo sapiens* hemoglobin subunit alpha 1 (hAg)), a 3' FI element (where F is a 136 nucleotide long 3'-UTR fragment of amino-terminal enhancer of split mRNA and I is a 142 nucleotide long fragment of mitochondrially encoded 12S RNA both identified in *Homo sapiens*; WO 2017/060314) and a poly(A) tail of 100 nucleotides, with a linker after 70 nucleotides.

Cytokine and serum albumin (hAlb) encoding sequences originate from *Homo sapiens* and no changes in the resulting amino acid sequences were introduced except for the intended mutations in the hIL2 variants described above (hIL2: NP_000577.2; NCBI protein resource). For cytokine constructs the hIL2 variant was added to the C-terminus of hAlb and encoded proteins were equipped with an N-terminal signal peptide (SP) that is the native SP of the respective protein. In case of fusion proteins, only the SP of the N-terminal moiety was maintained, for further moieties only the mature portion (protein without SP) was encoded. A stop-codon was introduced for the most C-terminal moiety only. Different protein moieties in the cytokine and hAlb fusion constructs were separated by a 30-nucleotide long linker sequence encoding for glycine and serine residues.

mRNA was generated by in vitro transcription as described by Kreiter et al. (Kreiter, S. et al. *Cancer Immunol. Immunother.* 56, 1577-87 (2007)) with substitution of the normal nucleoside uridine by 1-methyl-pseudouridine. Resulting mRNAs were equipped with a Cap1-structure and double-stranded (dsRNA) molecules were depleted. Purified mRNA was eluted in H$_2$O and stored at −80° C. until further use. In vitro transcription of all described mRNA constructs was carried out at BioNTech RNA Pharmaceuticals GmbH. A list of all constructs used in subsequent experiments is shown in Table 1.

TABLE 1

| Amino acid sequences of mRNA encoded and expressed proteins. | |
| --- | --- |
| hAlb | MKWVTFISLLFLFSSAYSRGVFRRDAHKSEVAHRFKDLGEENFKALVLIAFAQYL<br>QQCPFEDHVKLVNEVTEFAKTCVADESAENCDKSLHTLFGDKLCTVATLRETYG<br>EMADCCAKQEPERNECFLQHKDDNPNLPRLVRPEVDVMCTAFHDNEETFLKKY<br>LYEIARRHPYFYAPELLFFAKRYKAAFTECCQAADKAACLLPKLDELRDEGKASS<br>AKQRLKCASLQKFGERAFKAWAVARLSQRFPKAEFAEVSKLVTDLTKVHTECCH<br>GDLLECADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRY<br>TKKVPQVSTPTLVEVSRNLGKVGSKCCKHPEAKRMPCAEDYLSVVLNQLCVLH<br>EKTPVSDRVTKCCTESLVNRRPCFSALEVDETYVPKEFNAETFTFHADICTLSEK<br>ERQIKKQTALVELVKHKPKATKEQLKAVMDDFAAFVEKCCKADDKETCFAEEGK<br>KLVAASQAALGL |
| hAlb-hIL2 | MKWVTFISLLFLFSSAYSRGVFRRDAHKSEVAHRFKDLGEENFKALVLIAFAQYL<br>QQCPFEDHVKLVNEVTEFAKTCVADESAENCDKSLHTLFGDKLCTVATLRETYG<br>EMADCCAKQEPERNECFLQHKDDNPNLPRLVRPEVDVMCTAFHDNEETFLKKY<br>LYEIARRHPYFYAPELLFFAKRYKAAFTECCQAADKAACLLPKLDELRDEGKASS<br>AKQRLKCASLQKFGERAFKAWAVARLSQRFPKAEFAEVSKLVTDLTKVHTECCH<br>GDLLECADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRY<br>TKKVPQVSTPTLVEVSRNLGKVGSKCCKHPEAKRMPCAEDYLSVVLNQLCVLH<br>EKTPVSDRVTKCCTESLVNRRPCFSALEVDETYVPKEFNAETFTFHADICTLSEK<br>ERQIKKQTALVELVKHKPKATKEQLKAVMDDFAAFVEKCCKADDKETCFAEEGK<br>KLVAASQAALGLGGSGGGGSGGAPTSSSTKKTQLQLEHLLLDLQMILNGINNYK<br>NPKLTRMLTFKFYMPKKATELKHLQCLEEELKPLEEVLNLAQSKNFHLRPRDLIS<br>NINVIVLELKGSETTFMCEYADETATIVEFLNRWITFCQSIISTLT |
| hAlb-hIL2_A4 | MKWVTFISLLFLFSSAYSRGVFRRDAHKSEVAHRFKDLGEENFKALVLIAFAQYL<br>QQCPFEDHVKLVNEVTEFAKTCVADESAENCDKSLHTLFGDKLCTVATLRETYG<br>EMADCCAKQEPERNECFLQHKDDNPNLPRLVRPEVDVMCTAFHDNEETFLKKY<br>LYEIARRHPYFYAPELLFFAKRYKAAFTECCQAADKAACLLPKLDELRDEGKASS<br>AKQRLKCASLQKFGERAFKAWAVARLSQRFPKAEFAEVSKLVTDLTKVHTECCH<br>GDLLECADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKTYETTL<br>EKCCAAADPHECYAKVFDEFKPLVEEPQNLIKQNCELFEQLGEYKFQNALLVRY<br>TKKVPQVSTPTLVEVSRNLGKVGSKCCKHPEAKRMPCAEDYLSVVLNQLCVLH<br>EKTPVSDRVTKCCTESLVNRRPCFSALEVDETYVPKEFNAETFTFHADICTLSEK<br>ERQIKKQTALVELVKHKPKATKEQLKAVMDDFAAFVEKCCKADDKETCFAEEGK<br>KLVAASQAALGLGGSGGGGSGGAPTSSSTKKTQLQLEHLLLDLQMILNGINNYK<br>NPKLTRMLTFEFYMPKKATELKHLQCLEKELKPLEEVLNLAQSKNFHLRPRDLIS<br>NINVIVLELKGSETTFMCEYADETATIVEFLNRWITFCQSIISTLT |

TABLE 1-continued

Amino acid sequences of mRNA encoded and expressed proteins.

```
hAlb-hIL2_A4s    MKWVTFISLLFLFSSAYSRGVFRRDAHKSEVAHRFKDLGEENFKALVLIAFAQYL
                 QQCPFEDHVKLVNEVTEFAKTCVADESAENCDKSLHTLFGDKLCTVATLRETYG
                 EMADCCAKQEPERNECFLQHKDDNPNLPRLVRPEVDVMCTAFHDNEETFLKKY
                 LYEIARRHPYFYAPELLFFAKRYKAAFTECCQAADKAACLLPKLDELRDEGKASS
                 AKQRLKCASLQKFGERAFKAWAVARLSQRFPKAEFAEVSKLVTDLTKVHTECCH
                 GDLLECADDRADLAKYICENQDSISSKLKECCEKPLLEKSHCIAEVENDEMPADL
                 PSLAADFVESKDVCKNYAEAKDVFLGMFLYEYARRHPDYSVVLLLRLAKTYETTL
                 EKCCAAADPHECYAKVFDEFKPLVEEPQNLIKQNCELFEQLGEYKFQNALLVRY
                 TKKVPQVSTPTLVEVSRNLGKVGSKCCKHPEAKRMPCAEDYLSVVLNQLCVLH
                 EKTPVSDRVTKCCTESLVNRRPCFSALEVDETYVPKEFNAETFTFHADICTLSEK
                 ERQIKKQTALVELVKHKPKATKEQLKAVMDDFAAFVEKCCKADDKETCFAEEGK
                 KLVAASQAALGLGGSGGGGSGGAPTSSSTKKTQLQLEHLLLDLQMILNGINNYK
                 NPKLTRMLTFEFYMPKKATELKHLQCLEKELKPLEEVLNLAQSKNFHFDPRDVV
                 SNINVFVLELKGSETTFMCEYADETATIVEFLNRWITFCQSIISTLT hAlb-hIL2_A4s1   MKWVTFISLLFLFSSAYSRGVFRRDAHKSEVAHRFKDLGEENFKALVLIAFAQYL
                 QQCPFEDHVKLVNEVTEFAKTCVADESAENCDKSLHTLFGDKLCTVATLRETYG
                 EMADCCAKQEPERNECFLQHKDDNPNLPRLVRPEVDVMCTAFHDNEETFLKKY
                 LYEIARRHPYFYAPELLFFAKRYKAAFTECCQAADKAACLLPKLDELRDEGKASS
                 AKQRLKCASLQKFGERAFKAWAVARLSQRFPKAEFAEVSKLVTDLTKVHTECCH
                 GDLLECADDRADLAKYICENQDSISSKLKECCEKPLLEKSHCIAEVENDEMPADL
                 PSLAADFVESKDVCKNYAEAKDVFLGMFLYEYARRHPDYSVVLLLRLAKTYETTL
                 EKCCAAADPHECYAKVFDEFKPLVEEPQNLIKQNCELFEQLGEYKFQNALLVRY
                 TKKVPQVSTPTLVEVSRNLGKVGSKCCKHPEAKRMPCAEDYLSVVLNQLCVLH
                 EKTPVSDRVTKCCTESLVNRRPCFSALEVDETYVPKEFNAETFTFHADICTLSEK
                 ERQIKKQTALVELVKHKPKATKEQLKAVMDDFAAFVEKCCKADDKETCFAEEGK
                 KLVAASQAALGLGGSGGGGSGGAPTSSSTKKTQLQLEHLLLDLQMILNGINNYK
                 NPKLTRMLTFEFYMPKKATELKHLQCLEKELKPLEEVLNLAQSKNFHFEPRDVVS
                 NINVFVLELKGSETTFMCEYADETATIVEFLNRWITFCQSIISTLT hAlb-hIL2_A4s2   MKWVTFISLLFLFSSAYSRGVFRRDAHKSEVAHRFKDLGEENFKALVLIAFAQYL
                 QQCPFEDHVKLVNEVTEFAKTCVADESAENCDKSLHTLFGDKLCTVATLRETYG
                 EMADCCAKQEPERNECFLQHKDDNPNLPRLVRPEVDVMCTAFHDNEETFLKKY
                 LYEIARRHPYFYAPELLFFAKRYKAAFTECCQAADKAACLLPKLDELRDEGKASS
                 AKQRLKCASLQKFGERAFKAWAVARLSQRFPKAEFAEVSKLVTDLTKVHTECCH
                 GDLLECADDRADLAKYICENQDSISSKLKECCEKPLLEKSHCIAEVENDEMPADL
                 PSLAADFVESKDVCKNYAEAKDVFLGMFLYEYARRHPDYSVVLLLRLAKTYETTL
                 EKCCAAADPHECYAKVFDEFKPLVEEPQNLIKQNCELFEQLGEYKFQNALLVRY
                 TKKVPQVSTPTLVEVSRNLGKVGSKCCKHPEAKRMPCAEDYLSVVLNQLCVLH
                 EKTPVSDRVTKCCTESLVNRRPCFSALEVDETYVPKEFNAETFTFHADICTLSEK
                 ERQIKKQTALVELVKHKPKATKEQLKAVMDDFAAFVEKCCKADDKETCFAEEGK
                 KLVAASQAALGLGGSGGGGSGGAPTSSSTKKTQLQLEHLLLDLQMILNGINNYK
                 NPKLTRMLTFEFYMPKKATELKHLQCLEKELKPLEEVLNLAQSKNFHFEPRDVVS
                 NINVWVLELKGSETTFMCEYADETATIVEFLNRWITFCQSIISTLT hAlb-hIL2_A4s3   MKWVTFISLLFLFSSAYSRGVFRRDAHKSEVAHRFKDLGEENFKALVLIAFAQYL
                 QQCPFEDHVKLVNEVTEFAKTCVADESAENCDKSLHTLFGDKLCTVATLRETYG
                 EMADCCAKQEPERNECFLQHKDDNPNLPRLVRPEVDVMCTAFHDNEETFLKKY
                 LYEIARRHPYFYAPELLFFAKRYKAAFTECCQAADKAACLLPKLDELRDEGKASS
                 AKQRLKCASLQKFGERAFKAWAVARLSQRFPKAEFAEVSKLVTDLTKVHTECCH
                 GDLLECADDRADLAKYICENQDSISSKLKECCEKPLLEKSHCIAEVENDEMPADL
                 PSLAADFVESKDVCKNYAEAKDVFLGMFLYEYARRHPDYSVVLLLRLAKTYETTL
                 EKCCAAADPHECYAKVFDEFKPLVEEPQNLIKQNCELFEQLGEYKFQNALLVRY
                 TKKVPQVSTPTLVEVSRNLGKVGSKCCKHPEAKRMPCAEDYLSVVLNQLCVLH
                 EKTPVSDRVTKCCTESLVNRRPCFSALEVDETYVPKEFNAETFTFHADICTLSEK
                 ERQIKKQTALVELVKHKPKATKEQLKAVMDDFAAFVEKCCKADDKETCFAEEGK
                 KLVAASQAALGLGGSGGGGSGGAPTSSSTKKTQLQLEHLLLDLQMILNGINNYK
                 NPKLTRMLTFEFYMPKKATELKHLQCLEKELKPLEEVLNLAQSKNFHFEPRDLIS
                 NINVFVLELKGSETTFMCEYADETATIVEFLNRWITFCQSIISTLT hAlb-hIL2_A4s4   MKWVTFISLLFLFSSAYSRGVFRRDAHKSEVAHRFKDLGEENFKALVLIAFAQYL
                 QQCPFEDHVKLVNEVTEFAKTCVADESAENCDKSLHTLFGDKLCTVATLRETYG
                 EMADCCAKQEPERNECFLQHKDDNPNLPRLVRPEVDVMCTAFHDNEETFLKKY
                 LYEIARRHPYFYAPELLFFAKRYKAAFTECCQAADKAACLLPKLDELRDEGKASS
                 AKQRLKCASLQKFGERAFKAWAVARLSQRFPKAEFAEVSKLVTDLTKVHTECCH
                 GDLLECADDRADLAKYICENQDSISSKLKECCEKPLLEKSHCIAEVENDEMPADL
                 PSLAADFVESKDVCKNYAEAKDVFLGMFLYEYARRHPDYSVVLLLRLAKTYETTL
                 EKCCAAADPHECYAKVFDEFKPLVEEPQNLIKQNCELFEQLGEYKFQNALLVRY
                 TKKVPQVSTPTLVEVSRNLGKVGSKCCKHPEAKRMPCAEDYLSVVLNQLCVLH
                 EKTPVSDRVTKCCTESLVNRRPCFSALEVDETYVPKEFNAETFTFHADICTLSEK
                 ERQIKKQTALVELVKHKPKATKEQLKAVMDDFAAFVEKCCKADDKETCFAEEGK
                 KLVAASQAALGLGGSGGGGSGGAPTSSSTKKTQLQLEHLLLDLQMILNGINNYK
                 NPKLTRMLTFEFYMPKKATELKHLQCLEKELKPLEEVLNLAQSKNFHFDPRDLIS
                 NINVFVLELKGSETTFMCEYADETATIVEFLNRWITFCQSIISTLT hAlb-hIL2_A4s6   MKWVTFISLLFLFSSAYSRGVFRRDAHKSEVAHRFKDLGEENFKALVLIAFAQYL
                 QQCPFEDHVKLVNEVTEFAKTCVADESAENCDKSLHTLFGDKLCTVATLRETYG
                 EMADCCAKQEPERNECFLQHKDDNPNLPRLVRPEVDVMCTAFHDNEETFLKKY
```

TABLE 1-continued

Amino acid sequences of mRNA encoded and expressed proteins.

```
              LYEIARRHPYFYAPELLFFAKRYKAAFTECCQAADKAACLLPKLDELRDEGKASS
              AKQRLKCASLQKFGERAFKAWAVARLSQRFPKAEFAEVSKLVTDLTKVHTECCH
              GDLLECADDRADLAKYICENQDSISSKLKECCEKPLLEKSHCIAEVENDEMPADL
              PSLAADFVESKDVCKNYAEAKDVFLGMFLYEYARRHPDYSVVLLLRLAKTYETTL
              EKCCAAADPHECYAKVFDEFKPLVEEPQNLIKQNCELFEQLGEYKFQNALLVRY
              TKKVPQVSTPTLVEVSRNLGKVGSKCCKHPEAKRMPCAEDYLSVVLNQLCVLH
              EKTPVSDRVTKCCTESLVNRRPCFSALEVDETYVPKEFNAETFTFHADICTLSEK
              ERQIKKQTALVELVKHKPKATKEQLKAVMDDFAAFVEKCCKADDKETCFAEEGK
              KLVAASQAALGLGGSGGGGSGGAPTSSSTKKTQLQLEHLLLDLQMILNGINNYK
              NPKLTRMLTFEFYMPKKATELKHLQCLEKELKPLEEVLNLAHSKNFHFEPRDLIS
              NINVFVLELKGSETTFMCEYADETATIVEFLNRWITFCQSIISTLT hAlb-hIL2_A4s7 MKWVTFISLLFLFSSAYSRGVFRRDAHKSEVAHRFKDLGEENFKALVLIAFAQYL
              QQCPFEDHVKLVNEVTEFAKTCVADESAENCDKSLHTLFGDKLCTVATLRETYG
              EMADCCAKQEPERNECFLQHKDDNPNLPRLVRPEVDVMCTAFHDNEETFLKKY
              LYEIARRHPYFYAPELLFFAKRYKAAFTECCQAADKAACLLPKLDELRDEGKASS
              AKQRLKCASLQKFGERAFKAWAVARLSQRFPKAEFAEVSKLVTDLTKVHTECCH
              GDLLECADDRADLAKYICENQDSISSKLKECCEKPLLEKSHCIAEVENDEMPADL
              PSLAADFVESKDVCKNYAEAKDVFLGMFLYEYARRHPDYSVVLLLRLAKTYETTL
              EKCCAAADPHECYAKVFDEFKPLVEEPQNLIKQNCELFEQLGEYKFQNALLVRY
              TKKVPQVSTPTLVEVSRNLGKVGSKCCKHPEAKRMPCAEDYLSVVLNQLCVLH
              EKTPVSDRVTKCCTESLVNRRPCFSALEVDETYVPKEFNAETFTFHADICTLSEK
              ERQIKKQTALVELVKHKPKATKEQLKAVMDDFAAFVEKCCKADDKETCFAEEGK
              KLVAASQAALGLGGSGGGGSGGAPTSSSTKKTQLQLEHLLLDLQMILNGINNYK
              NPKLTRMLTFEFYMPKKATELKHLQCLEKELKPLEEVLNLAHSKNFHFEPRDLIS
              NINVWVLELKGSETTFMCEYADETATIVEFLNRWITFCQSIISTLT hAlb-hIL2_A4s8 MKWVTFISLLFLFSSAYSRGVFRRDAHKSEVAHRFKDLGEENFKALVLIAFAQYL
              QQCPFEDHVKLVNEVTEFAKTCVADESAENCDKSLHTLFGDKLCTVATLRETYG
              EMADCCAKQEPERNECFLQHKDDNPNLPRLVRPEVDVMCTAFHDNEETFLKKY
              LYEIARRHPYFYAPELLFFAKRYKAAFTECCQAADKAACLLPKLDELRDEGKASS
              AKQRLKCASLQKFGERAFKAWAVARLSQRFPKAEFAEVSKLVTDLTKVHTECCH
              GDLLECADDRADLAKYICENQDSISSKLKECCEKPLLEKSHCIAEVENDEMPADL
              PSLAADFVESKDVCKNYAEAKDVFLGMFLYEYARRHPDYSVVLLLRLAKTYETTL
              EKCCAAADPHECYAKVFDEFKPLVEEPQNLIKQNCELFEQLGEYKFQNALLVRY
              TKKVPQVSTPTLVEVSRNLGKVGSKCCKHPEAKRMPCAEDYLSVVLNQLCVLH
              EKTPVSDRVTKCCTESLVNRRPCFSALEVDETYVPKEFNAETFTFHADICTLSEK
              ERQIKKQTALVELVKHKPKATKEQLKAVMDDFAAFVEKCCKADDKETCFAEEGK
              KLVAASQAALGLGGSGGGGSGGAPTSSSTKKTQLQLEHLLLDLQMILNGINNYK
              NPKLTRMLTFEFYMPKKATELKHLQCLEKELKPLEEVLNLAHSKNFHFEPRDVIS
              NINVFVLELKGSETTFMCEYADETATIVEFLNRWITFCQSIISTLT
```

Example 2: Functional Activity of Novel hAlb-hIL2_A4 Variants with Mutations in the hIL2Rβ (CD122) Binding Region in Comparison to Parental hAlb-hIL2_A4 on Different Cell Subsets in Human PBMCs and Mouse Splenocytes Measured by IL2-Mediated Phosphorylation of STAT5

To assess the functional activity of novel hAlb-hIL2_A4 variants additionally mutated in the hIL2Rβ (CD122) binding region in comparison to hAlb-hIL2_A4 mutated only in the hIL2Rα (CD25) binding region, different CD25$^+$ and CD25$^-$ T-cell subsets as well as NK cells in bulk human PBMCs (FIG. 1) or mouse splenocytes (FIG. 2) were stimulated with cytokine-containing supernatants and assayed for STAT5 phosphorylation. In order to generate cytokine-containing supernatants, $1.2 \times 10^6$ HEK293T/17 cells were seeded in 3 mL DMEM (Life Technologies GmbH, cat. no. 31966-021)+10% fetal bovine serum (FBS, Biochrom GmbH, cat. no. S0115) in 6-well plates and incubated at 37° C., 5% $CO_2$ overnight. The next day, 3 μg cytokine-encoding mRNA was formulated under sterile and RNase-free conditions using 400 ng mRNA per μL Lipofectamine™ MessengerMax™ (Thermo Fisher Scientific, cat. No. LMRNA015) and applied per 10 cm$^2$ culture dish to the HEK293T/17 cells at approximately 80% confluence. After 20 h of expression, supernatants were collected under sterile conditions and stored at −20° C. until further use.

PBMCs were obtained from buffy coats of healthy donors by Ficoll-Paque™ (1.073 g/mL, VWR international, cat. no. 17-1440-03) density gradient separation. PBMCs were washed twice with D-PBS (Life Technologies GmbH, cat. no. 14190250) and collected by centrifugation for 8 min, 300×g at room temperature. For isolation of mouse splenocytes, one Balb/c mouse (Balb/c JRj, Janvier Labs) was euthanized by cervical dislocation and the spleen removed from the peritoneal cavity. The spleen was mechanically dissociated through a 70-μm cell strainer and the resulting cell suspension was washed once in D-PBS before separation of the cells by Ficoll-Paque™ (1.084 g/mL, VWR International, cat. no. 17-5446-02) density gradient centrifugation. Isolated splenocytes were washed twice with D-PBS and collected by centrifugation for 8 min, 300×g at room temperature. For STAT5 phosphorylation assay, PBMCs were re-suspended in Iscove's Modified Dulbecco's Medium (IMDM; Life Technologies GmbH, cat. no. 12440-053) supplemented with 5% plasma-derived human serum (PHS; One Lambda Inc., cat. no. A25761) and splenocytes were re-suspended in RPMI 1640 (Life Technologies GmbH, cat. no. 61870010) supplemented with 10% FBS and both were rested for 1 h at 37° C. and 5% $CO_2$. Next, 125,000 PBMCs or splenocytes were seeded per well of a 96-well V-bottom plate (Greiner Bio-One GmbH, cat. no. 651101) in the respective medium. In parallel, six four-fold serial dilutions of cytokine-containing supernatants were generated in IMDM supplemented with 5% PHS or RPMI 1640 supplemented with 10% FBS. Seeded cells were mixed 1:1 (referring to the volume of the culture medium of the seeded cells) with cytokine-containing supernatants and stimulated for 10 min at 37° C. and 5% $CO_2$. Next, 1:1000 fixable viability dye eFluor™ 780 was added and the cells stimulated for another 5 min at 37° C. and 5% $CO_2$. The cells were fixed by addition of formaldehyde (Carl Roth GmbH+ Co. KG, cat. no. P087.4) to 2% and incubated for 10 min on ice. Fixed cells were washed with ice cold D-PBS and permeabilized with 100% ice-cold methanol for 30 min on ice. Permeabilized PBMCs were washed twice with D-PBS supplemented with 2% FBS and 2 mM EDTA (Sigma-Aldrich, cat. no. 03690-100ML) and subsequently stained with 1:5 Alexa Fluor® 488 Anti-Stat5 (pY694) (Becton Dickinson GmbH, cat. no. 612598), 1:25 PerCP-Cy™ 5.5 Mouse Anti-Human CD25 (Becton Dickinson GmbH, cat. no. 560503), 1:50 BV421 Mouse Anti-Human CD4 (Becton Dickinson GmbH, cat. no. 565997), 1:25 BV510 Mouse Anti-Human CD8 (Becton Dickinson GmbH, cat. no. 563256) and 1:12.5 APC Mouse Anti-Human CD56 (Becton Dickinson GmbH, cat. no. 555518) in D-PBS supplemented with 2% FBS and 2 mM EDTA for 30 min at 2-8° C. protected from light. Permeabilized splenocytes were washed twice with D-PBS supplemented with 2% FBS and 2 mM EDTA (Sigma-Aldrich, cat. no. 03690-100ML) and subsequently stained with 1:5 Alexa Fluor® 488 Anti-Stat5 (pY694) (Becton Dickinson GmbH, cat. no. 612598), 1:25 PerCP-Cy™5.5 Rat Anti-Mouse CD25 (Becton Dickinson GmbH, cat. no. 551071), 1:50 BV786 Rat Anti-Mouse CD4 (Becton Dickinson GmbH, cat. no. 563727), 1:25 BV605 Rat Anti-Mouse CD8 (Becton Dickinson GmbH, cat. no. 563152) and 1:25 BV421 Rat Anti-Mouse CD49b (Becton Dickinson GmbH, cat. no. 563063) in D-PBS supplemented with 2% FBS and 2 mM EDTA for 30 min at 2-8° C. protected from light. Stained PBMCs and splenocytes were washed twice and finally re-suspended in D-PBS supplemented with 2% FBS and 2 mM EDTA. Flow cytometric analysis was performed on a BD FACSCanto™ II or FACS-Celesta™ flow cytometer (Becton Dickinson GmbH) and acquired data was analyzed using FlowJo™ software version 10. Dose-response curves and $EC_{50}$ values were calculated in GraphPad Prism version 6.04 (GraphPad Software, Inc.).

Figure 1:
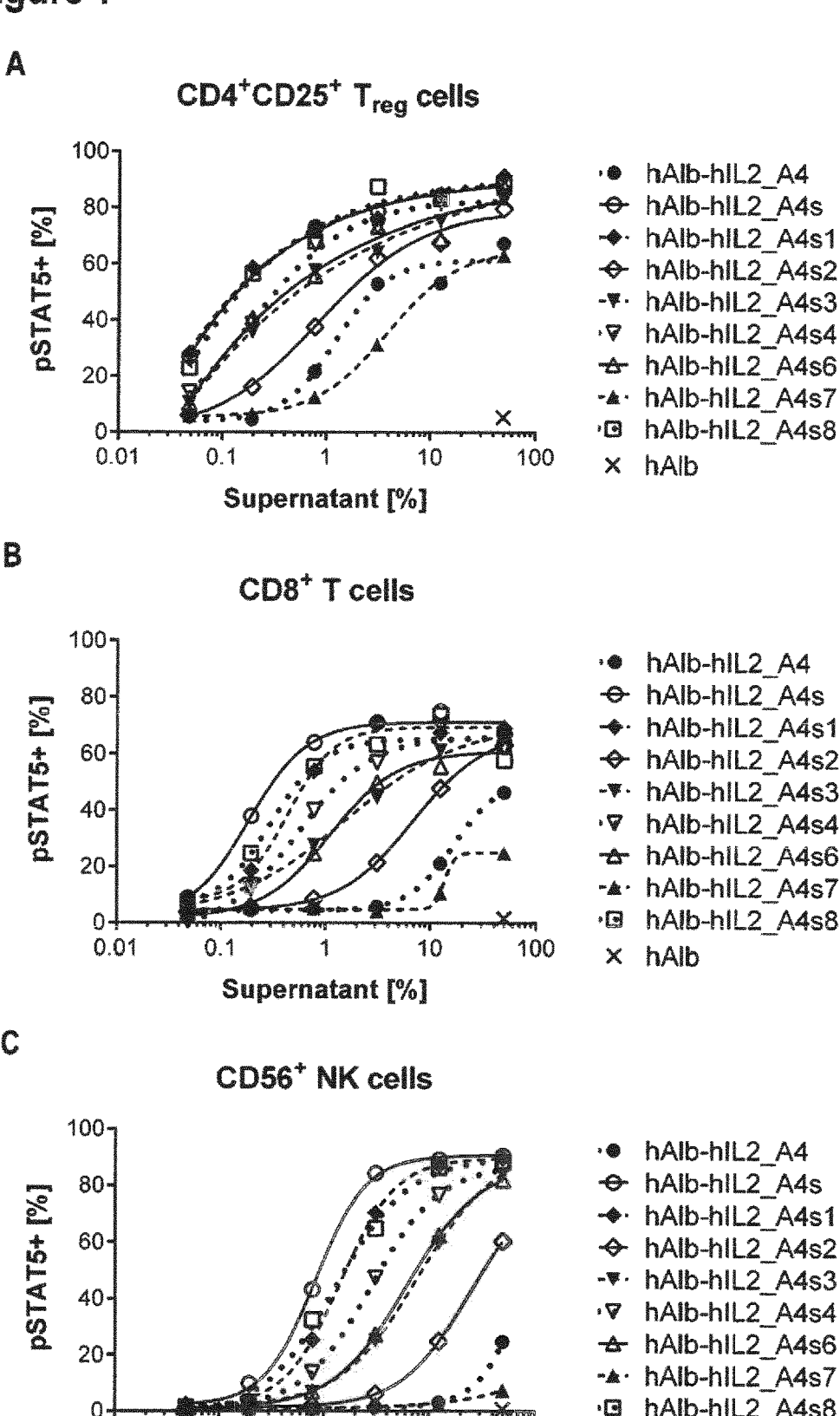
FIG. 1: Functional activity of hAlb-hIL2_A4 variants on different lymphocyte subsets in human PBMCs measured by IL2-mediated phosphorylation of STAT5.

On all analyzed PBMC subsets, independent of CD25 expression, all novel hAlb-hIL2_A4 variants designed for increased CD122 binding except for hAlb-hIL2_A4s7 displayed superior potency over hAlb-hIL2_A4. In detail, the biological activity of hAlb-hIL2_A4s, hAlb-hIL2_A4s1 and hAlb-hIL2_A4s8 was strongly increased by at least one log-step (CD4⁺CD25⁺ $T_{reg}$, $EC_{50}$ approx. 0.1%-supernatant) or up to two log-steps (CD8⁺ T cells, $EC_{50}$ 0.182%-supernatant) compared to hAlb-hIL2_A4 ($EC_{50}$ 1.247%-supernatant on $T_{reg}$, $EC_{50}$>20%-supernatant on CD8⁺ T cells) (FIG. 1, Table 2). hAlb-hIL2_A4s, hAlb-hIL2_A4s1 and hAlb-hIL2_A4s8 performed on par on CD4⁺CD25⁺ $T_{reg}$ cells and were similarly effective on CD8⁺ T cells and CD56+NK cells. Besides hAlb-hIL2_A4s7, hAlb-hIL2_A4s2 showed the least increase in biological activity, while the other variants hAlb-hIL2_A4s3, hAlb-hIL2_A4s4 and hAlb-hIL2_A4s6 exhibited an intermediate phenotype (FIG. 1). On mouse splenocytes comparable results were obtained regarding the performance of the various hAlb-hIL2_A4 variants among each other, however, mouse splenocytes showed an overall reduced sensitivity towards hAlb-hIL2_A4 variant-induced phosphorylation of STAT5 of around 30-fold (FIG. 2).

TABLE 2

| $EC_{50}$ values [%-supernatant] calculated based on STAT5 phosphorylation dose-response for the hAlb-hIL2_A4 variants in different human PBMC subsets. | | | |
| --- | --- | --- | --- |
| hAlb-hIL2 variant | CD4⁺CD25⁺ $T_{reg}$ cells | CD8⁺ T cells | CD56⁺ NK cells |
| hAlb-hIL2_A4 | 1.247 | >20 | >50 |
| hAlb-hIL2_A4s | ~0.1 | 0.182 | 0.829 |
| hAlb-hIL2_A4s1 | ~0.1 | 0.436 | 1.437 |
| hAlb-hIL2_A4s2 | 0.851 | 6.881 | >20 |
| hAlb-hIL2_A4s3 | ~0.5 | 1.550 | 7.802 |
| hAlb-hIL2_A4s4 | 0.176 | 0.546 | 2.803 |
| hAlb-hIL2_A4s6 | ~0.2 | 1.118 | 6.125 |
| hAlb-hIL2_A4s7 | 3.904 | >50 | n/a |
| hAlb-hIL2_A4s8 | ~0.1 | 0.298 | 1.282 |

Example 3: Relative Bioactivity of Novel hAlb-hIL2_A4 Variants with Mutations in the hIL2Rβ (CD122) Binding Region on Intermediate-Affinity IL2 Receptor (IL2Rβγ)- and High-Affinity IL2 Receptor (IL2Rαβγ)-Expressing IL-2 Dependent Reporter Cell Lines In order to dissect if specifically the hIL2Rα chain (CD25) influences the biological activity of the different novel hAlb-hIL2_A4 variants, the proliferation responses of TF-1_hIL2Rβγ and TF-1_hIL2Rαβγ cells, derived from the human erythroleukemic cell line TF-1 (ATCC CRL-2003) that naturally expresses the IL2R common γ-chain, were determined (FIG. 3). The cell lines were generated by transduction with retroviral vector encoding for the sequence of the human IL2Rβ chain (Gene ID: 3560) and optionally a second retroviral vector encoding the sequence of the human hIL2Rα chain (Gene ID: 3559) analogous to Farner, N. L. et al. Blood 86, 4568-4578 (1995). In short, TF-1_IL2Rβγ and TF-1_IL2Rαβγ cells were harvested from continuous culture, washed two times with D-PBS and resuspended in RPMI 1640 supplemented with 10% FBS and 1 mM sodium pyruvate (Life Technologies GmbH, cat. no. 11360070). A total of 5,000 cells/well were seeded in white 96-well flat-bottom plates (Fisher Scientific GmbH, cat. no. 10072151) and were incubated with eight four-fold serial dilutions of hAlb-hIL2_A4 variant-containing supernatants (generated as described in Example 2). After three days of culture proliferation was measured by quantitating viable cells via ATP amount using the CellTiter-Glo® 2.0 Assay (Promega, cat. no. G9242). Luminescence was recorded on a Tecan Infinite® F200 PRO reader (Tecan Deutschland GmbH) and dose-response curves were plotted as well as $EC_{50}$ values calculated in GraphPad Prism version 6.04 (GraphPad Software, Inc.).

On CD25-independent, IL2Rβγ-expressing TF-1_hIL2Rβγ cells, hAlb-hIL2_A4s, hAlb-hIL2_A4s1 and hAlb-hIL2_A4s8 performed on par with nearly superimposable dose response curves (FIG. 3A). This is also reflected in the calculated $EC_{50}$ values ranging from 0.712%-supernatant for hAlb-hIL2_A4s to 0.755%-supernatant for hAlb-hIL2_A4s1 and 0.807%-supernatant for hAlb-hIL2_A4s8 (Table 3). Variants hAlb-hIL2_A4s2 and hAlb-hIL2_A4s7 showed a more than 10-fold shift towards decreased biological activity as expected from results in Example 2. The remaining variants hAlb-hIL2_A4s3, hAlb-hIL2_A4s4 and hAlb-hIL2_A4s6 displayed an intermediate phenotype with $EC_{50}$ values between 1.270%-supernatant and 2.557%-supernatant (FIG. 3A, Table 3). In contrast, on CD25-dependent, IL2Rαβγ-expressing TF-1_hIL2Rαβγ cells the dose-response curves of all hAlb-hIL2 variants slightly shifted towards increased bioactivity and the differences between the individual variants were less pronounced (FIG. 3 B). While hAlb-hIL2_A4s1 and hAlb-hIL2_A4s8 were still identified as top-performers with $EC_{50}$ values of 0.216%-supernatant and 0.236%-supernatant, respectively, all other variants except for hAlb-hIL2_A4s7 ($EC_{50}$ 2.689%-supernatant) displayed similar $EC_{50}$ values between 0.314%-supernatant and 0.566%-supernatant (FIG. 3 B, Table 3).

TABLE 3

$EC_{50}$ values [%-supernatant] calculated based on proliferation dose-responses of intermediate-affinity IL2 receptor (IL2Rβγ)-dependent TF-1_IL2Rβγ cell culture and of high-affinity IL2 receptor (IL2Rαβγ)-dependent TF-1_IL2Rαβγ cell culture.

| hAlb-hIL2 variant | TF-1_IL2Rβγ | TF-1_IL2Rαβγ |
|---|---|---|
| hAlb-hIL2_A4s | 0.712 | 0.314 |
| hAlb-hIL2_A4s1 | 0.755 | 0.216 |
| hAlb-hIL2_A4s2 | 7.646 | 0.566 |
| hAlb-hIL2_A4s3 | 2.557 | 0.305 |
| hAlb-hIL2_A4s4 | 1.270 | 0.254 |
| hAlb-hIL2_A4s6 | 1.903 | 0.414 |
| hAlb-hIL2_A4s7 | >50 | 2.689 |
| hAlb-hIL2_A4s8 | 0.807 | 0.236 |

Among the hAlb-hIL2_A4s variants tested in Example 2 and 3, we have selected hAlb-hIL2_A4s8 for further characterization due to the overall promising results shown in FIGS. 1 to 3.

Example 4: Binding of hAlb-hIL2, hAlb-hIL2_A4 and hAlb-hIL2_A4s8 to Recombinant hIL2Rα (CD25) and hIL2Rβ (CD122)

The binding capacity of mRNA-encoded wild-type hAlb-hIL2, hAlb-hIL2_A4 (designed for reduced CD25 binding) and hAlb-hIL2_A4s8 (designed for reduced CD25 binding and increased CD122 binding) to hIL2Rα (CD25) and hIL2Rβ (CD122) was analyzed by ELISA (FIG. 4). Here, 1 µg/mL recombinant human CD25 (C-Fc, Novoprotein cat no. CJ78) or human CD122 (C-Fc, Novoprotein cat. no. CJ82) was coated overnight in 100 µL D-PBS to high protein-binding 96-well plates (Nunc MaxiSorp™, Thermo Fisher Scientific, cat. no. 439454). hAlb-hIL2 variant-containing supernatants generated as described in Example 2 were applied to coated CD25 or CD122 and bound protein was detected via an HRP-conjugated anti-human Serum Albumin antibody (Abcam, cat. no. ab8941). General ELISA reagents and procedures were applied according to the protocol of DuoSet ELISA Ancillary Reagent Kit 2 (R&D Systems, cat. No. DY008).

Binding to hIL2Rα (CD25) was only detected for wild-type hAlb-hIL2, while the two variants hAlb-hIL2_A4 and hAlb-hIL2_A4s8 carrying the K43E and E61K mutations for reduced hIL2Rα binding did not show any binding (FIG. 4A). In contrast, hIL2Rβ (CD122) was bound only by hAlb-hIL2_A4s8 equipped with mutations for increased hIL2Rβ binding (Q74H, L80F, R81E, L85V, I92F), but not by hAlb-hIL2 and hAlb-hIL2_A4 (FIG. 4 B). Taken together, both results clearly confirm the functionality of the mutations that were introduced into hAlb-hIL2_A4s8 to both decrease binding to hIL2Rα and increase binding to hIL2Rβ.

Example 5: Functional Activity and 'Regulatory T Cell Bias' of hAlb-hIL2_A4s8 Compared to hAlb-hIL2 on Different Cell Subsets in Human PBMCs and Mouse PBMCs Measured by IL2-Mediated Phosphorylation of STAT5

The functional activity of hAlb-hIL2_A4s8 in comparison to wild-type hAlb-hIL2 was assessed on CD4+CD25+ $T_{reg}$ cells, CD25-negative CD8+ T cells and CD56+NK cells in human PBMCs (FIG. 5) as well as CD4+CD25+ $T_{reg}$ cells and CD25-negative CD8+ T cells in mouse PBMCs (FIG. 6). For human PBMCS, IL2-mediated phosphorylation of STAT5 induced by hAlb-hIL2 variant-containing supernatant was analyzed as described in Example 2. Resulting dose-response curves were fitted with a four parameter logarithmic fit to calculate $EC_{50}$ values in GraphPad Prism version 6.04 (GraphPad Software, Inc.). Dose-response curves for hAlb-hIL2 on CD8+ T cells and CD56+NK cells were interpolated for supernatant concentrations above 12.5% in order to estimate $EC_{50}$ values (Table 4). The ratio of $EC_{50}$ values determined for hAlb-hIL2 or hAlb-hIL2_A4s8 on CD8+ T cells or CD56+NK cells versus $EC_{50}$ values determined on CD4+CD25+ $T_{reg}$ cells was calculated to determine the 'regulatory T cell bias' of hAlb-hIL2 and hAlb-hIL2_A4s8 (Table 5). For isolation of mouse PBMCs, 2-3 Balb/c mice (Balb/c JRj, Janvier Labs) were euthanized by cervical dislocation, terminally bled and whole blood collected in Li-Heparin tubes (Microvette®, VWR International, cat. no. SARS20.1309). 2.5 mL blood was mixed 1:1 with D-PBS and PBMCs isolated by Ficoll-Paque™ (1.084, cat. no. 17-5446-02) density gradient centrifugation. Isolated PBMCs were washed twice with D-PBS and collected by centrifugation for 8 min, 300×g at room temperature. IL2-mediated phosphorylation of STAT5 in hAlb-hIL2 variant-containing supernatant-treated mouse PBMCs was analyzed as described for mouse splenocytes in Example 2.

In line with the ELISA data given in Example 4, hAlb-hIL2 displayed superior potency on human CD4+CD25+ Tregs (FIG. 5A) but showed only very limited activity on CD25-negative CD8+ T cells and CD56+NK cells (FIG. 5 B-C). In contrast, hAlb-hIL2_A4s8 displayed a 10-fold reduced bioactivity on CD4+CD25+ Tregs compared to hAlb-hIL2 (FIG. 5A) but outperformed hAlb-hIL2 on CD25-negative immune cells (CD8+ T cells and CD56+NK cells, FIG. 5 B-C). Comparison of the $EC_{50}$ values on CD4+CD25+ Tregs versus CD25-negative cell subsets was used to calculate the 'regulatory T cell bias' for both hAlb-hIL2 and hAlb-hIL2_A4s8 (Table 4 and Table 5). hAlb-hIL2 exhibits a calculated bias of more than 400-fold towards CD4+CD25+ Tregs when compared to its biological effect on CD8+ cytotoxic T cells and CD56+ NK cells. In contrast, the regulatory T cell bias is largely reduced to only 1.3 to 3.1-fold for hAlb-hIL2_A4s8 depending on the respective comparator immune cell subset. Consequently, hAlb-hIL2_A4s8 designed with point mutations that decrease hIL2Rα binding (K43E, E61K) while increasing hIL2Rβ binding (Q74H, L80F, R81E, L85V, I92F) was confirmed to be an hIL2Rβ-biased variant of hAlb-hIL2 that shows a markedly reduced capacity to activate CD4+CD25+ Tregs coming along with the ability to stimulate effector immune cells (e.g. CD8+ T cells) already at lower concentrations. On mouse PBMCs, comparable results were obtained regarding the performance of hAlb-hIL2_A4s8 versus hAlb-hIL2. hAlb-hIL2 by far outperformed hAlb-hIL2_A4s8 on CD4+CD25+ Tregs, whereas hAlb-hIL2_A4s8 was superior to hAlb-hIL2 on mouse CD8+ T cells (FIG. 6A-B).

67

TABLE 4

EC$_{50}$ values [%-supernatant] calculated based on STAT5 phosphorylation dose-response for hAlb-hIL2 and hAlb-hIL2_A4s8 in different human PBMC subsets.

| hAlb-hIL2 variant | CD4$^+$CD25$^+$ T$_{reg}$ cells | CD8$^+$ T cells | CD56$^+$ NK cells |
|---|---|---|---|
| hAlb-hIL2 | 0.0311 | 25.68 * | 12.99 * |
| hAlb-hIL2_A4s8 | 0.360 | 1.471 | 0.476 |

* projected EC$_{50}$ value

TABLE 5

The 'regulatory T cell bias' of hAlb-hIL2 and hAlb-hIL2_A4s8 given as fold-reduced potency on human CD8$^+$ T cells or CD56$^+$ NK cells compared to CD4$^+$CD25$^+$ T$_{reg}$ cells.

| hAlb-hIL2 variant | CD8$^+$ T cells | CD56$^+$ NK cells |
|---|---|---|
| hAlb-hIL2 | 825-fold * | 418-fold * |
| hAlb-hIL2_A4s8 | 3.1-fold | 1.3-fold |

* approximation; calculated on basis of projected EC$_{50}$ values

Example 6: The IL2 Variant hAlb-hIL2_A4s8 with Combined Mutations in hILRα and hILRβ Binding Regions is Superior to hAlb-hIL2 in Boosting Anti-Tumoral Immunity in Combination with a Therapeutic RNA Vaccine in the Murine Colon Carcinoma Model CT26

We subsequently characterized the potency of the selected IL2 variant hAlb-hIL2_A4s8 to improve therapeutic anti-tumoral efficacy of an RNA vaccine in vivo. BALB/c mice (n=11 per group) were inoculated with 5×10$^5$ CT26 tumor cells subcutaneously (s.c.) and vaccinated intravenously (i.v.) four times weekly (day 10, 17, 24 and 31) with 20 μg RNA-LPX encoding the CD8$^+$ T-cell antigen gp70 (SPSYAYHQF) as described in Kranz et al. (Kranz, L. M. et al. Nature 534, 396-401 (2016). gp70 is a tumor antigen which can be found in the colon carcinoma cell line CT26. Anti-tumor efficacy of a gp70 targeting vaccine increases with rising numbers of induced gp70 specific T cells (Kranz, L. M. et al. Nature 534, 396-401 (2016) and unpublished). Concomitantly with the RNA vaccine, RNAs coding for hAlb-hIL2_A4s8 or hAlb-hIL2 (3 μg each) and formulated as lipid nanoparticles (LNPs) were administered i.v. The control group received RNA vaccine and hAlb RNA (not coding for any cytokine) formulated as LNPs. Blood lymphocyte subsets and gp70-specific T-cell responses were determined seven days after the first three treatments (day 17, 24 and 31) via flow cytometry (BD FACSCelesta™) (staining as described in Kranz, L. M. et al. Nature 534, 396-401 (2016)). Anti-tumor efficacy was determined as tumor growth inhibition in the test groups compared to the control group and overall survival during an observation period of up to day 104 after tumor inoculation.

Combination treatment of the vaccine with hAlb-hIL2 and hAlb-hIL2_A4s8 resulted in significantly reduced tumor growth and prolonged survival compared to the control (FIG. 7A, B). In the group treated with hAlb-hIL2, seven of 11 (64%) animals showed a complete response. The most potent effect was observed in the group treated with hAlb-hIL2_A4s8, leading to a complete response in 11 of 11 (100%) animals. In comparison, all mice in the control group had to be sacrificed before day 39.

Tumor antigen-specific T cells and NK cells play important roles in tumor control whereas T$_{reg}$ cells are known to inhibit anti-tumor immunity. Increased gp70 tumor antigen-specific CD8$^+$ T-cell numbers were observed in the groups treated with hAlb-hIL2 and hAlb-hIL2_A4s8 across all measurement days (FIG. 8 A). In concordance to the IL2R binding profile, only hAlb-hIL2_A4s8 resulted in a potent expansion of NK cells seven days after the first treatment (day 17). NK cells, once activated, quickly disappeared from the blood which explains the significant reduction of NK cell numbers on day 24 (FIG. 8 B). Both hAlb-hIL2 and hAlb-hIL2_A4s8 led to a significant increase of CD8$^+$ T cells not specific for gp70 (non-antigen-specific), with hAlb-hIL2_A4s8 inducing the strongest cell expansions (FIG. 9A). CD4$^+$ T cells were not elevated by hAlb-hIL2 or hAlb-hIL2_A4s8 treatment. Only hAlb-hIL2 but not hAlb-hIL2_A4s8 led to an expansion of T$_{reg}$ cells. The ratio of effector T cells to T$_{reg}$ cells critically impacts the efficacy of T-cell based immunotherapies. hAlb-hIL2 and hAlb-hIL2_A4s8 both and equally improved the ratio of gp70-specific T cells over T$_{reg}$ cells. In addition, treatment with hAlb-hIL2_A4s8 increased the ratio of non-gp70-specific CD8$^+$ T cells to T$_{reg}$ cells (FIG. 9 B).

In summary, in combination with an antigen-specific vaccine, both hAlb-hIL2 and the variant hAlb-hIL2_A4s8 resulted in tumor control with hAlb-hIL2_A4s8 being most effective. Whereas hAlb-hIL2 increases mainly antigen-specific T cells and T$_{reg}$ cells, hAlb-hIL2_A4s8 activates NK cells and elevates both antigen-specific and non-antigen-specific CD8$^+$ T-cell numbers without expanding T$_{reg}$ cells.

Example 7: The IL2 Variant hAlb-hIL2_A4s8 Improves Anti-Tumoral Immunity as Monotherapy in the Murine Colon Carcinoma Model CT26

We investigated further whether hAlb-hIL2_A4s8 was efficient as monotherapy. BALB/c mice (n=11 per group) were inoculated with 5×10$^5$ CT26 tumor cells subcutaneously (s.c.) and treated intravenously (i.v.) four times weekly (day 10, 17, 24 and 31) with RNA coding for hAlb-hIL2_A4s8 and formulated as LNP, with or without concomitant i.v. vaccination with 20 μg gp70 RNA-LPX described in Example 6. The control group received hAlb RNA (not coding for any cytokine) formulated as LNPs and an RNA vaccine not coding for any antigen (irr vaccine), or gp70 vaccine alone. Blood lymphocyte subsets and gp70-specific T-cell responses were determined seven days after the first three treatments (day 17, 24 and 31) via flow cytometry as described in Example 6. Anti-tumor efficacy was determined as tumor growth inhibition in the test groups compared to the control group and overall survival during an observation period of up to day 100 after tumor inoculation.

Treatment with hAlb-hIL2_A4s8 resulted in significantly reduced tumor growth and prolonged survival compared to the control receiving hAlb with irr vaccine or gp70 vaccine alone (FIG. 10A, B). In the group treated with hAlb and irr vaccine, one of 11 (9%) animals rejected the tumor and survived until day 100. In the group treated with gp70 vaccine, two of 11 (18%) animals survived this period. In the group that received hAlb-hIL2_A4s8 as monotherapy, tumor growth inhibition and survival improved to five of 11 (45%) mice. Combination of hAlb-hIL2_A4s8 with gp70 vaccination increased the fraction of complete responses further, and 10 of 11 (91%) animals rejected their tumors and survived.

Similarly to the previous study (Example 6), hAlb-hIL2_A4s8 treatment combined with the gp70 vaccine led to a drastic increase of antigen-specific CD8$^+$ T-cell and NK-cell numbers after the first treatment and over time (FIG.

11A, B). hAlb-hIL2_A4s8 alone also increased the number of antigen-specific CD8$^+$ T cells, but only slightly, albeit significantly (FIG. 11A, FIG. 12A). hAlb-hIL2_A4s8 alone also expanded NK cells equally well as the combination. Again, NK cells quickly disappeared from the blood after initial expansion. T$_{reg}$ cells, as shown before, were not expanded by treatment with hAlb-hIL2_A4s8, and dropped further with continuous treatment (FIG. 11 C). Similarly to the combination with the gp70 vaccine, hAlb-hIL2_A4s8 expanded the number of CD8$^+$ T cells while not changing the number of CD4$^+$ T cells (FIG. 12A). Expansion of antigen-specific as well as total CD8$^+$ T cells while stabilizing the number of T$_{reg}$ cells led to a highly significant increase of the antigen-specific CD8$^+$ T cell to T$_{reg}$ cell ratio, as well as the ratio of CD8$^+$ T cells over T$_{reg}$ cells (FIG. 12 B). While hAlb-hIL2_A4s8 monotherapy expanded CD8$^+$ T cells irrespective of their antigen specificity, the combination with gp70 vaccine synergized in expanding preferentially gp70-specific CD8$^+$ T cells over non-gp70-specific CD8$^+$ T cells (FIG. 12 C). gp70 vaccination alone did not induce any measurable alteration of the analyzed cell subsets.

Taken together it was shown that hAlb-hIL2_A4s8 treatment leads to a potent increase of CD8$^+$ T cells and NK cells without any measurable increase of T$_{reg}$ cells in turn, thereby resulting in anti-tumor efficacy as monotherapy or in combination with a tumor-antigen specific T-cell vaccine.

Example 8: The IL2 Variant hAlb-hIL2_A4s8 is Superior to hAlb-hIL2 in Boosting Anti-Tumoral Immunity in Combination with a Therapeutic RNA Vaccine in the Murine Melanoma Model B16

In order to confirm the potency of hAlb-hIL2_A4s8 in a low immunogenic murine tumor model, C57BL/6 mice (n=15 per group) were inoculated subcutaneously (s.c.) with $3 \times 10^5$ B16-F10 melanoma cells and treated intravenously (i.v.) five times weekly (day 8, 15, 22, 29 and 36) with RNA coding for hAlb-hIL2_A4s8 or hAlb-hIL2 formulated as LNP, with or without concomitant i.v. vaccination with 20 μg TRP1 RNA-LPX. TRP1 is the murine melanosomal antigen tyrosine-related protein-1 and is a self-antigen expressed constitutively on B16-F10 melanoma cells as well as in normal melanocytes. Anti-tumor efficacy of this TRP1 vaccine was demonstrated in Kranz et al. (Kranz, L. M. et al. *Nature* 534, 396-401 (2016)). The control groups received hAlb RNA (not coding for any cytokine) formulated as LNPs and an RNA vaccine not coding for any antigen (irr vaccine), or hAlb with the TRP1 vaccine. Blood lymphocyte subsets and TRP1-specific T-cell responses were determined seven days after the first three treatments (day 15, 22 and 29) via flow cytometry as described in Example 6. Anti-tumor efficacy was determined as tumor growth inhibition in the test groups compared to the control group and overall survival during an observation period of up to day 75 after tumor inoculation.

Compared to the control group treated with hAlb and irr vaccine, TRP1 vaccination alone demonstrated little therapeutic efficacy with a modest tendency for tumor growth reduction and increased median survival (FIG. 13A, B). Treatment with both hAlb-hIL2 and Alb-hIL2_A4s8 led to significant tumor growth reduction resulting in complete rejection of tumors in five of 15 (33%) animals for both treatments. Whereas TRP1 vaccination did not improve survival of hAlb-hIL2-treated animals, hAlb-hIL2_A4s8 treatment benefited from simultaneous TRP1 vaccination, resulting in further tumor growth reduction and strongly enhanced survival compared to each individual therapy. Of the animals treated with the combination of hAlb-hIL2_A4s8 and TRP1 vaccine, six of 15 (40%) rejected their tumor and 50% survived the observation period.

Treatment with hAlb-hIL2 or hAlb-hIL2-A4s8 alone did not induce TRP1-specific CD8$^+$ T cells, while TRP1 vaccination resulted in a weak TRP1-specific CD8$^+$ T-cell response (FIG. 14A). As observed in the colon carcinoma model (Example 6 and Example 7), the combination of hAlb-hIL2_A4s8 with the TRP1 vaccine strongly boosted TRP1-specific CD8$^+$ T-cell numbers over time. Despite higher initial numbers of TRP1-specific CD8$^+$ T cells, the combination of hAlb-hIL2 with the TRP1 vaccine took longer for TRP1-specific CD8$^+$ T cells to reach levels similar to hAlb-hIL2_A4s8 over time. Again, hAlb-hIL2_A4s8 expanded NK cells after the first treatment, which dropped to baseline levels subsequently (FIG. 14 B). Neither alone nor in combination with the TRP1 vaccine did hAlb-hIL2_A4s8 expand T$_{reg}$ cells, while hAlb-hIL2 boosted T$_{reg}$ cell numbers after the first treatment (FIG. 14 C). Initial expansion of T$_{reg}$ cells by hAlb-hIL2 may explain the delayed increase in TRP1-specific CD8$^+$ T cells observed in FIG. 14A, based on the more T$_{reg}$-sensitive and susceptible mouse model. Confirming prior experiments, both hAlb-hIL2 and hAlb-hIL2_A4s8 alone or in combination significantly increased the number of total CD8$^+$ T cells, where hAlb-hIL2_A4s8 was superior, and only hAlb-hIL2 affected the number of CD4$^+$ T cells (FIG. 15 A). As observed before, expansion of these CD8$^+$ T cell subsets resulted in preferential total CD8$^+$ T cell to T$_{reg}$ cell ratios in response to treatment with hAlb-hIL2_A4s8 alone or in combination with the TRP1 vaccine (FIG. 15 B). While treatment with either hAlb-hIL2 alone, hAlb-hIL2_A4s8 alone or TRP1 vaccine alone had no or only little effect on the ratio of antigen-specific CD8$^+$ T cells over T$_{reg}$ cells, the combination boosted this ratio in favor of antigen-specific CD8$^+$ T cells and increased it further with continuing treatment, for both hAlb-hIL2 and hAlb-hIL2_A4s8 (FIG. 15 B). Similarly to observations in the colon carcinoma model (Example 7, FIG. 12 C), hAlb-hIL2_A4s8 monotherapy expanded CD8$^+$ T cells irrespective of their antigen specificity, whereas the combination with the TRP1 vaccine synergized in expanding preferentially TRP1-specific CD8$^+$ T cells over non-TRP1-specific CD8$^+$ T cells (FIG. 15 C). The same was true for treatment with hAlb-hIL2 and the combination with the TRP1 vaccine.

In summary, hAlb-hIL2_A4s8 is effective as monotherapy also in a low immunogenic tumor model and, in contrast to hAlb-hIL2, synergizes with T-cell vaccination by expanding vaccine-induced T-cell responses while avoiding stimulation and expansion of T$_{reg}$ cells.

Example 9: The IL2 Variant hAlb-hIL2_A4s8 Boosts Anti-Tumoral Immunity Alone and in Combination with PD-L1 Blockade in the Murine Colon Carcinoma Model MC38

As multiple studies have shown that IL2 or modified IL2 variants synergize with PD-1/PD-L1 blocking antibodies (Moynihan, K D et al. Nat. Med. 22 (12): 1402-10 (2016), Castro, D T et al. SITC Abstract #P557 (2018)), we anticipated that the potency of hAlb-hIL2_A4s8 could be further augmented by combination with immune checkpoint blockade. C57BL/6 mice (n=14 per group) were inoculated subcutaneously (s.c.) with $7.5 \times 10^5$ MC38 colon carcinoma cells and treated intravenously (i.v.) four times weekly (day 17, 24, 32 and 39) with RNA coding for hAlb-hIL2_A4s8 and formulated as LNP, with or without concomitant intraperitoneal (i.p.) treatment with anti-PD-L1 antibody (first injection 200 µg, then 100 µg for all consecutive injections). Control groups received hAlb RNA (not coding for any cytokine) formulated as LNPs and isotype control antibody, as well as hAlb and anti-PD-L1. Blood lymphocyte subsets and Adpgk-specific T-cell responses were determined seven days after the second treatment (day 31) via flow cytometry as described in Example 6. Adpgk is a neoantigen expressed specifically by MC38 tumor cells but not by normal cells (Yadav, M et al., Nature 515 (7528): 572-6 (2014). Antitumor efficacy was determined as tumor growth inhibition in the test groups compared to the control groups and overall survival during an observation period of up to day 74 after tumor inoculation.

Compared to the control group treated with hAlb and isotype control antibody, hAlb-hIL2_A4s8 and anti-PD-L1 treatment alone showed a tendency for reduced tumor growth and increased survival (FIG. 16 A, B). The combination of hAlb-hIL2_A4s8 and anti-PD-L1 strongly synergized and improved the anti-tumor effect of anti-PD-L1. With the combination, nine of 14 (64%) animals rejected their tumors. None of the tumors was rejected in the control group.

Treatment with hAlb-hIL2_A4s8 alone elevated CD8$^+$ T cell numbers, which were significantly higher than in the control group when combined with anti-PD-L1 antibody treatment (FIG. 17A). Similarly, antigen-specific CD8$^+$ T cells specific for the tumor-specific neoantigen Adpgk were expanded above background level by hAlb-hIL2_A4s8 alone, and were boosted significantly when combined with anti-PD-L1 antibody. Treatment did not affected the number of CD4$^+$ T cells, and T$_{reg}$ cell numbers remained equally unaffected by treatment with hAlb-hIL2_A4s8 (FIG. 17A). The ratios of total CD8$^+$ T cells, and antigen-specific CD8$^+$ T cells over T$_{reg}$ cells profited from treatment with hAlb-hIL2_A4s8, with a tendency for anti-PD-L1 antibody to be beneficial on top (FIG. 17 B). Anti-PD-L1 alone did not affect any of the cell subsets or ratios analyzed.

Taken together, hAlb-hIL2_A4s8 improved the anti-tumoral efficacy of PD-L1 immune checkpoint blockade by expanding CD8$^+$ T cells, and specifically pre-existing antigen-specific CD8$^+$ T cells.

Example 10: Treatment with hAlb-hIL2-A4s8 Monotherapy or in Combination with PD-L1 Checkpoint Blockade or Therapeutic RNA Vaccination Modulates Lymphocyte Numbers in the Tumor in the Murine Tumor Model MC38

In the previous examples, we determined the effect of hAlb-hIL2_A4s8 alone or in combination with RNA vaccination, or PD-L1 checkpoint blockade on tumor growth, survival and lymphocyte numbers in the blood. Therapeutic activity was associated with an increase in CD8$^+$ and CD4$^+$ T lymphocytes, NK cells and tumor antigen-specific T cells. No significant increase in T$_{reg}$ cells was observed, which led to an overall increase of the T cell to T$_{reg}$ cell ratio. However, whether increase of effector lymphocytes in the blood also corresponded to an increase in the tumor where they are believed to promote tumor cell killing, was not shown so far.

In this experiment, the modulation of the tumor microenvironment was investigated upon hAlb-hIL2_A4s8 treatment in the highly immunogenic colon carcinoma model MC38. MC38 tumors contain several mutated neoantigens recognized by CD8$^+$ T cells originating from point-mutated genes (Yadav, M. et al. Nature 515, 572-576 (2014); Capietto, A. et al. The Journal of experimental medicine 217, e20190179 (2020). As described in Example 9, treatment with hAlb-hIL2_A4s8 synergizes with PD-L1 checkpoint blockade and increases the induction of T-cell responses against tumor-specific neoantigens in the blood (FIG. 17). A subsequent experiment in MC38 tumor-bearing mice was performed to analyze infiltration of tumor neoantigen-specific T cells into the tumor.

C57BL/6 mice (n=7-8 per group) were inoculated subcutaneously (s.c.) with $7.5 \times 10^5$ MC38 colon carcinoma cells and 19 days later treated i.v. with LNP formulated RNA coding for hAlb-hIL2_A4s8 (3 µg) and concomitant i.p. treatment with anti-PD-L1 antibody (200 µg). Control groups received one out of the two therapies or received no treatment at all (control for hAlb-hIL2_A4s8: hAlb RNA formulated as LNPs ('hAlb'); control for anti-PD-L1 antibody: Isotype antibody ('iso')). Tumor and blood of mice were sampled on day 24 and analyzed by flow cytometry (BD FACSCelesta™). Blood was processed and stained as described earlier (Kranz, L. M. et al. Nature 534, 396-401 (2016). Tumors were digested using the Tumor Dissociation Kit, mouse (Miltenyi Biotec) and the GentleMACS™ Dissociator (Miltenyi Biotec, Cat. 130-093-235). Upon erythrocyte lysis with standard ACK buffer (8.25 g NH$_4$CL, 1 g KHCO$_3$, 0.2 ml EDTA, 1 L distilled H$_2$O), cells were stained for flow cytometry analysis as described before (Kranz, L. M. et al. Nature 534, 396-401 (2016)). Analysis was performed using FlowJo™ software version 10 and GraphPad Prism version 8.

As shown in FIGS. 18A and B, CD8$^+$ T cells and NK cells in the tumor were significantly elevated in all hAlb-hIL2_A4s8 treated groups. Combination with an anti-PD-L1 antibody (αPD-L1) further elevated T-cell numbers although PD-L1 blockade on its own had no effect. In this model, no significant elevation of intratumoral CD4$^+$ T cells was detected (FIG. 18 C). As observed in TC-1 tumors, the intratumoral T$_{reg}$ fraction among CD4$^+$ T cells was not altered by any of the treatments, resulting in an overall increase of the CD8$^+$ T cell to T$_{reg}$ cell ratio in the tumor upon hAlb-hIL2_A4s8 administration (FIGS. 18 D and E). Importantly, tumor-specific CD8$^+$ T cells recognizing neoantigens derived from mutated Adpgk, Rpl18 or N4pb2l2 were significantly elevated in both hAlb-hIL2_A4s8 treated groups (FIG. 18 F-H). Similarly, hAlb-hIL2_A4s8 treatment resulted in increased numbers of CD8$^+$ and CD4$^+$ T cells as well as Adpgk, Rpl18 and N4pb2l2 neoantigen-specific T cells in the blood (FIG. 18 I-M).

In summary, hAlb-hIL2_A4s8 treatment alone or in combination with PD-L1 checkpoint blockade and/or RNA vaccination coincided with an increase of (tumor antigen-specific) effector T cells and NK cells in the tumor and the blood.

The invention claimed is:

1. A polypeptide comprising a mutein of human interleukin (IL2) according to SEQ ID NO: 1 or of a variant having at least 90% sequence identity to SEQ ID NO: 1, wherein the human IL2 or the variant thereof is substituted, relative to SEQ ID NO: 1, at leucine 80 by phenylalanine, arginine 81 by glutamic acid, leucine 85 by valine and isoleucine 92 by phenylalanine.

2. The polypeptide of claim 1, wherein the human IL2 or the variant is further substituted, relative to SEQ ID NO: 1, at glutamine 74 by histidine.

3. The polypeptide of claim 1, wherein the human IL2 or the variant is further substituted, relative to SEQ ID NO: 1, at lysine 43 and glutamic acid 61.

4. The polypeptide of claim 3, wherein lysine 43 is substituted by glutamic acid and glutamic acid 61 is substituted by lysine.

5. The polypeptide of claim 1, wherein the human IL2 or the variant is not substituted, relative to SEQ ID NO: 1, at isoleucine 86.

6. The polypeptide of claim 1, further comprising a half-life extending moiety.

7. The polypeptide of claim 6, wherein the half-life extending moiety selected from the group consisting of serum albumin, an immunoglobulin fragment, transferrin, Fn3, and variants thereof.

8. A pharmaceutical composition comprising the polypeptide of claim 1.

*    *    *    *    *

SEQUENCE LISTING

<160> NUMBER OF SEQ ID NOS: 23

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 2
<211> LENGTH: 133
<212> TYPE: PRT
<213> ORGANISM: Artificial Sequence
<220> FEATURE:
<223> OTHER INFORMATION: hIL2_s8

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Glu Pro Arg Asp Val Ile Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 3
<211> LENGTH: 133
<212> TYPE: PRT
<213> ORGANISM: Artificial Sequence

```
<220> FEATURE:
<223> OTHER INFORMATION: hIL2_A4

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Glu Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 4
<211> LENGTH: 133
<212> TYPE: PRT
<213> ORGANISM: Artificial Sequence
<220> FEATURE:
<223> OTHER INFORMATION: hIL2_A4s

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Glu Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 5
<211> LENGTH: 133
<212> TYPE: PRT
<213> ORGANISM: Artificial Sequence
<220> FEATURE:
<223> OTHER INFORMATION: hIL2_A4s1

<400> SEQUENCE: 5
```

-continued

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Glu Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Phe
65                  70                  75                  80

Glu Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130
```

```
<210> SEQ ID NO 6
<211> LENGTH: 133
<212> TYPE: PRT
<213> ORGANISM: Artificial Sequence
<220> FEATURE:
<223> OTHER INFORMATION: hIL2_A4s2

<400> SEQUENCE: 6
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Glu Phe Tyr Met Pro Lys
        35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Phe
65                  70                  75                  80

Glu Pro Arg Asp Val Val Ser Asn Ile Asn Val Trp Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130
```

```
<210> SEQ ID NO 7
<211> LENGTH: 133
<212> TYPE: PRT
<213> ORGANISM: Artificial Sequence
<220> FEATURE:
<223> OTHER INFORMATION: hIL2_A4s3

<400> SEQUENCE: 7
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

-continued

```
Asn Pro Lys Leu Thr Arg Met Leu Thr Phe Glu Phe Tyr Met Pro Lys
    35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Phe
65                  70                  75                  80

Glu Pro Arg Asp Leu Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
    130

<210> SEQ ID NO 8
<211> LENGTH: 133
<212> TYPE: PRT
<213> ORGANISM: Artificial Sequence
<220> FEATURE:
<223> OTHER INFORMATION: hIL2_A4s4

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Glu Phe Tyr Met Pro Lys
    35                  40                  45

Lys Ala Thr Glu Leu Lys His Leu Gln Cys Leu Glu Lys Glu Leu Lys
    50                  55                  60

Pro Leu Glu Glu Val Leu Asn Leu Ala Gln Ser Lys Asn Phe His Phe
65                  70                  75                  80

Asp Pro Arg Asp Leu Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
    130

<210> SEQ ID NO 9
<211> LENGTH: 133
<212> TYPE: PRT
<213> ORGANISM: Artificial Sequence
<220> FEATURE:
<223> OTHER INFORMATION: hIL2_A4s6

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Glu Phe Tyr Met Pro Lys
    35                  40                  45

Lys Ala Thr Glu Leu Lys His Leu Gln Cys Leu Glu Lys Glu Leu Lys
```

-continued

```
        50              55              60

Pro Leu Glu Glu Val Leu Asn Leu Ala His Ser Lys Asn Phe His Phe
65              70              75              80

Glu Pro Arg Asp Leu Ile Ser Asn Ile Asn Val Phe Val Leu Glu Leu
                85              90              95

Lys Gly Ser Glu Thr Thr Phe Met Cys Glu Tyr Ala Asp Glu Thr Ala
                100             105             110

Thr Ile Val Glu Phe Leu Asn Arg Trp Ile Thr Phe Cys Gln Ser Ile
            115             120             125

Ile Ser Thr Leu Thr
        130

<210> SEQ ID NO 10
<211> LENGTH: 133
<212> TYPE: PRT
<213> ORGANISM: Artificial Sequence
<220> FEATURE:
<223> OTHER INFORMATION: hIL2_A4s7

<400> SEQUENCE: 10

Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
                20              25              30

Asn Pro Lys Leu Thr Arg Met Leu Thr Phe Glu Phe Tyr Met Pro Lys
            35              40              45

Lys Ala Thr Glu Leu Lys His Leu Gln Cys Leu Glu Lys Glu Leu Lys
        50              55              60

Pro Leu Glu Glu Val Leu Asn Leu Ala His Ser Lys Asn Phe His Phe
65              70              75              80

Glu Pro Arg Asp Leu Ile Ser Asn Ile Asn Val Trp Val Leu Glu Leu
                85              90              95

Lys Gly Ser Glu Thr Thr Phe Met Cys Glu Tyr Ala Asp Glu Thr Ala
                100             105             110

Thr Ile Val Glu Phe Leu Asn Arg Trp Ile Thr Phe Cys Gln Ser Ile
            115             120             125

Ile Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: hIL2_A4s8

<400> SEQUENCE: 11

Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
                20              25              30

Asn Pro Lys Leu Thr Arg Met Leu Thr Phe Glu Phe Tyr Met Pro Lys
            35              40              45

Lys Ala Thr Glu Leu Lys His Leu Gln Cys Leu Glu Lys Glu Leu Lys
        50              55              60

Pro Leu Glu Glu Val Leu Asn Leu Ala His Ser Lys Asn Phe His Phe
65              70              75              80
```

-continued

```
Glu Pro Arg Asp Val Ile Ser Asn Ile Asn Val Phe Val Leu Glu Leu
                85              90              95

Lys Gly Ser Glu Thr Thr Phe Met Cys Glu Tyr Ala Asp Glu Thr Ala
            100             105             110

Thr Ile Val Glu Phe Leu Asn Arg Trp Ile Thr Phe Cys Gln Ser Ile
        115             120             125

Ile Ser Thr Leu Thr
    130

<210> SEQ ID NO 12
<211> LENGTH: 752
<212> TYPE: PRT
<213> ORGANISM: Artificial Sequence
<220> FEATURE:
<223> OTHER INFORMATION: hAlb-hIL2

<400> SEQUENCE: 12

Met Lys Trp Val Thr Phe Ile Ser Leu Leu Phe Leu Phe Ser Ser Ala
1               5               10              15

Tyr Ser Arg Gly Val Phe Arg Arg Asp Ala His Lys Ser Glu Val Ala
            20              25              30

His Arg Phe Lys Asp Leu Gly Glu Glu Asn Phe Lys Ala Leu Val Leu
        35              40              45

Ile Ala Phe Ala Gln Tyr Leu Gln Gln Cys Pro Phe Glu Asp His Val
    50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
                85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
        115             120             125

His Lys Asp Asp Asn Pro Asn Leu Pro Arg Leu Val Arg Pro Glu Val
    130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
            165             170             175

Glu Leu Leu Phe Phe Ala Lys Arg Tyr Lys Ala Ala Phe Thr Glu Cys
            180             185             190

Cys Gln Ala Ala Asp Lys Ala Ala Cys Leu Leu Pro Lys Leu Asp Glu
        195             200             205

Leu Arg Asp Glu Gly Lys Ala Ser Ser Ala Lys Gln Arg Leu Lys Cys
    210             215             220

Ala Ser Leu Gln Lys Phe Gly Glu Arg Ala Phe Lys Ala Trp Ala Val
225             230             235             240

Ala Arg Leu Ser Gln Arg Phe Pro Lys Ala Glu Phe Ala Glu Val Ser
            245             250             255

Lys Leu Val Thr Asp Leu Thr Lys Val His Thr Glu Cys Cys His Gly
            260             265             270

Asp Leu Leu Glu Cys Ala Asp Asp Arg Ala Asp Leu Ala Lys Tyr Ile
        275             280             285

Cys Glu Asn Gln Asp Ser Ile Ser Ser Lys Leu Lys Glu Cys Cys Glu
    290             295             300
```

-continued

```
Lys Pro Leu Leu Glu Lys Ser His Cys Ile Ala Glu Val Glu Asn Asp
305             310             315             320

Glu Met Pro Ala Asp Leu Pro Ser Leu Ala Ala Asp Phe Val Glu Ser
                325             330             335

Lys Asp Val Cys Lys Asn Tyr Ala Glu Ala Lys Asp Val Phe Leu Gly
            340             345             350

Met Phe Leu Tyr Glu Tyr Ala Arg Arg His Pro Asp Tyr Ser Val Val
            355             360             365

Leu Leu Leu Arg Leu Ala Lys Thr Tyr Glu Thr Thr Leu Glu Lys Cys
        370             375             380

Cys Ala Ala Ala Asp Pro His Glu Cys Tyr Ala Lys Val Phe Asp Glu
385             390             395             400

Phe Lys Pro Leu Val Glu Glu Pro Gln Asn Leu Ile Lys Gln Asn Cys
                405             410             415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
        435             440             445

Glu Val Ser Arg Asn Leu Gly Lys Val Gly Ser Lys Cys Cys Lys His
        450             455             460

Pro Glu Ala Lys Arg Met Pro Cys Ala Glu Asp Tyr Leu Ser Val Val
465             470             475             480

Leu Asn Gln Leu Cys Val Leu His Glu Lys Thr Pro Val Ser Asp Arg
                485             490             495

Val Thr Lys Cys Cys Thr Glu Ser Leu Val Asn Arg Arg Pro Cys Phe
                500             505             510

Ser Ala Leu Glu Val Asp Glu Thr Tyr Val Pro Lys Glu Phe Asn Ala
            515             520             525

Glu Thr Phe Thr Phe His Ala Asp Ile Cys Thr Leu Ser Glu Lys Glu
        530             535             540

Arg Gln Ile Lys Lys Gln Thr Ala Leu Val Glu Leu Val Lys His Lys
545             550             555             560

Pro Lys Ala Thr Lys Glu Gln Leu Lys Ala Val Met Asp Asp Phe Ala
                565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
            595             600             605

Leu Gly Gly Ser Gly Gly Gly Gly Ser Gly Gly Ala Pro Thr Ser Ser
        610             615             620

Ser Thr Lys Lys Thr Gln Leu Gln Leu Glu His Leu Leu Leu Asp Leu
625             630             635             640

Gln Met Ile Leu Asn Gly Ile Asn Asn Tyr Lys Asn Pro Lys Leu Thr
                645             650             655

Arg Met Leu Thr Phe Lys Phe Tyr Met Pro Lys Lys Ala Thr Glu Leu
            660             665             670

Lys His Leu Gln Cys Leu Glu Glu Glu Leu Lys Pro Leu Glu Glu Val
            675             680             685

Leu Asn Leu Ala Gln Ser Lys Asn Phe His Leu Arg Pro Arg Asp Leu
        690             695             700

Ile Ser Asn Ile Asn Val Ile Val Leu Glu Leu Lys Gly Ser Glu Thr
705             710             715             720

Thr Phe Met Cys Glu Tyr Ala Asp Glu Thr Ala Thr Ile Val Glu Phe
```

-continued

```
                   725             730             735
Leu Asn Arg Trp Ile Thr Phe Cys Gln Ser Ile Ile Ser Thr Leu Thr
            740             745             750

<210> SEQ ID NO 13
<211> LENGTH: 752
<212> TYPE: PRT
<213> ORGANISM: Artificial Sequence
<220> FEATURE:
<223> OTHER INFORMATION: hAlb-hIL2_S8

<400> SEQUENCE: 13

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
```

-continued

```
                340             345               350

Met Phe Leu Tyr Glu Tyr Ala Arg Arg His Pro Asp Tyr Ser Val Val
            355             360                 365

Leu Leu Leu Arg Leu Ala Lys Thr Tyr Glu Thr Thr Leu Glu Lys Cys
        370             375             380

Cys Ala Ala Ala Asp Pro His Glu Cys Tyr Ala Lys Val Phe Asp Glu
385             390             395                 400

Phe Lys Pro Leu Val Glu Glu Pro Gln Asn Leu Ile Lys Gln Asn Cys
            405             410             415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
            435             440             445

Glu Val Ser Arg Asn Leu Gly Lys Val Gly Ser Lys Cys Cys Lys His
            450             455             460

Pro Glu Ala Lys Arg Met Pro Cys Ala Glu Asp Tyr Leu Ser Val Val
465             470             475                 480

Leu Asn Gln Leu Cys Val Leu His Glu Lys Thr Pro Val Ser Asp Arg
            485             490             495

Val Thr Lys Cys Cys Thr Glu Ser Leu Val Asn Arg Arg Pro Cys Phe
            500             505             510

Ser Ala Leu Glu Val Asp Glu Thr Tyr Val Pro Lys Glu Phe Asn Ala
            515             520             525

Glu Thr Phe Thr Phe His Ala Asp Ile Cys Thr Leu Ser Glu Lys Glu
            530             535             540

Arg Gln Ile Lys Lys Gln Thr Ala Leu Val Glu Leu Val Lys His Lys
545             550             555                 560

Pro Lys Ala Thr Lys Glu Gln Leu Lys Ala Val Met Asp Asp Phe Ala
            565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
            595             600             605

Leu Gly Gly Ser Gly Gly Gly Ser Gly Gly Ala Pro Thr Ser Ser
            610             615             620

Ser Thr Lys Lys Thr Gln Leu Gln Leu Glu His Leu Leu Leu Asp Leu
625             630             635                 640

Gln Met Ile Leu Asn Gly Ile Asn Asn Tyr Lys Asn Pro Lys Leu Thr
            645             650             655

Arg Met Leu Thr Phe Lys Phe Tyr Met Pro Lys Lys Ala Thr Glu Leu
            660             665             670

Lys His Leu Gln Cys Leu Glu Glu Glu Leu Lys Pro Leu Glu Glu Val
            675             680             685

Leu Asn Leu Ala Gln Ser Lys Asn Phe His Phe Glu Pro Arg Asp Val
            690             695             700

Ile Ser Asn Ile Asn Val Phe Val Leu Glu Leu Lys Gly Ser Glu Thr
705             710             715                 720

Thr Phe Met Cys Glu Tyr Ala Asp Glu Thr Ala Thr Ile Val Glu Phe
            725             730             735

Leu Asn Arg Trp Ile Thr Phe Cys Gln Ser Ile Ile Ser Thr Leu Thr
            740             745             750
```

<210> SEQ ID NO 14

```
<211> LENGTH: 752
<212> TYPE: PRT
<213> ORGANISM: Artificial Sequence
<220> FEATURE:
<223> OTHER INFORMATION: hAlb-hIL2_A4

<400> SEQUENCE: 14

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
    370                 375                 380
```

-continued

```
Cys Ala Ala Ala Asp Pro His Glu Cys Tyr Ala Lys Val Phe Asp Glu
385             390             395             400

Phe Lys Pro Leu Val Glu Glu Pro Gln Asn Leu Ile Lys Gln Asn Cys
                405             410             415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
            435             440             445

Glu Val Ser Arg Asn Leu Gly Lys Val Gly Ser Lys Cys Cys Lys His
        450             455             460

Pro Glu Ala Lys Arg Met Pro Cys Ala Glu Asp Tyr Leu Ser Val Val
465             470             475             480

Leu Asn Gln Leu Cys Val Leu His Glu Lys Thr Pro Val Ser Asp Arg
                485             490             495

Val Thr Lys Cys Cys Thr Glu Ser Leu Val Asn Arg Arg Pro Cys Phe
            500             505             510

Ser Ala Leu Glu Val Asp Glu Thr Tyr Val Pro Lys Glu Phe Asn Ala
            515             520             525

Glu Thr Phe Thr Phe His Ala Asp Ile Cys Thr Leu Ser Glu Lys Glu
        530             535             540

Arg Gln Ile Lys Lys Gln Thr Ala Leu Val Glu Leu Val Lys His Lys
545             550             555             560

Pro Lys Ala Thr Lys Glu Gln Leu Lys Ala Val Met Asp Asp Phe Ala
            565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
        595             600             605

Leu Gly Gly Ser Gly Gly Gly Gly Ser Gly Gly Ala Pro Thr Ser Ser
    610             615             620

Ser Thr Lys Lys Thr Gln Leu Gln Leu Glu His Leu Leu Leu Asp Leu
625             630             635             640

Gln Met Ile Leu Asn Gly Ile Asn Asn Tyr Lys Asn Pro Lys Leu Thr
                645             650             655

Arg Met Leu Thr Phe Glu Phe Tyr Met Pro Lys Lys Ala Thr Glu Leu
            660             665             670

Lys His Leu Gln Cys Leu Glu Lys Glu Leu Lys Pro Leu Glu Glu Val
            675             680             685

Leu Asn Leu Ala Gln Ser Lys Asn Phe His Leu Arg Pro Arg Asp Leu
        690             695             700

Ile Ser Asn Ile Asn Val Ile Val Leu Glu Leu Lys Gly Ser Glu Thr
705             710             715             720

Thr Phe Met Cys Glu Tyr Ala Asp Glu Thr Ala Thr Ile Val Glu Phe
            725             730             735

Leu Asn Arg Trp Ile Thr Phe Cys Gln Ser Ile Ile Ser Thr Leu Thr
            740             745             750
```

```
<210> SEQ ID NO 15
<211> LENGTH: 752
<212> TYPE: PRT
<213> ORGANISM: Artificial Sequence
<220> FEATURE:
<223> OTHER INFORMATION: hAlb-hIL2_A4s

<400> SEQUENCE: 15
```

-continued

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415
```

-continued

```
Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Gly Gly Ser Gly Gly Gly Gly Ser Gly Gly Ala Pro Thr Ser Ser
            610                 615                 620

Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Lys Leu Thr
                645                 650                 655

Arg Met Leu Thr Phe Glu Phe Tyr Met Pro Lys Lys Ala Thr Glu Leu
            660                 665                 670

Lys His Leu Gln Cys Leu Glu Lys Glu Leu Lys Pro Leu Glu Glu Val
            675                 680                 685

Leu Asn Leu Ala Gln Ser Lys Asn Phe His Phe Asp Pro Arg Asp Val
            690                 695                 700

Val Ser Asn Ile Asn Val Phe Val Leu Glu Leu Lys Gly Ser Glu Thr
705                 710                 715                 720

Thr Phe Met Cys Glu Tyr Ala Asp Glu Thr Ala Thr Ile Val Glu Phe
                725                 730                 735

Leu Asn Arg Trp Ile Thr Phe Cys Gln Ser Ile Ile Ser Thr Leu Thr
            740                 745                 750
```

```
<210> SEQ ID NO 16
<211> LENGTH: 752
<212> TYPE: PRT
<213> ORGANISM: Artificial Sequence
<220> FEATURE:
<223> OTHER INFORMATION: hAlb-hIL2_A4s1

<400> SEQUENCE: 16

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30
```

-continued

```
His Arg Phe Lys Asp Leu Gly Glu Glu Asn Phe Lys Ala Leu Val Leu
        35              40              45

Ile Ala Phe Ala Gln Tyr Leu Gln Gln Cys Pro Phe Glu Asp His Val
        50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
                85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
            115             120             125

His Lys Asp Asp Asn Pro Asn Leu Pro Arg Leu Val Arg Pro Glu Val
        130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
                165             170             175

Glu Leu Leu Phe Phe Ala Lys Arg Tyr Lys Ala Ala Phe Thr Glu Cys
            180             185             190

Cys Gln Ala Ala Asp Lys Ala Ala Cys Leu Leu Pro Lys Leu Asp Glu
            195             200             205

Leu Arg Asp Glu Gly Lys Ala Ser Ser Ala Lys Gln Arg Leu Lys Cys
        210             215             220

Ala Ser Leu Gln Lys Phe Gly Glu Arg Ala Phe Lys Ala Trp Ala Val
225             230             235             240

Ala Arg Leu Ser Gln Arg Phe Pro Lys Ala Glu Phe Ala Glu Val Ser
                245             250             255

Lys Leu Val Thr Asp Leu Thr Lys Val His Thr Glu Cys Cys His Gly
            260             265             270

Asp Leu Leu Glu Cys Ala Asp Asp Arg Ala Asp Leu Ala Lys Tyr Ile
            275             280             285

Cys Glu Asn Gln Asp Ser Ile Ser Ser Lys Leu Lys Glu Cys Cys Glu
        290             295             300

Lys Pro Leu Leu Glu Lys Ser His Cys Ile Ala Glu Val Glu Asn Asp
305             310             315             320

Glu Met Pro Ala Asp Leu Pro Ser Leu Ala Ala Asp Phe Val Glu Ser
                325             330             335

Lys Asp Val Cys Lys Asn Tyr Ala Glu Ala Lys Asp Val Phe Leu Gly
            340             345             350

Met Phe Leu Tyr Glu Tyr Ala Arg Arg His Pro Asp Tyr Ser Val Val
            355             360             365

Leu Leu Leu Arg Leu Ala Lys Thr Tyr Glu Thr Thr Leu Glu Lys Cys
        370             375             380

Cys Ala Ala Ala Asp Pro His Glu Cys Tyr Ala Lys Val Phe Asp Glu
385             390             395             400

Phe Lys Pro Leu Val Glu Glu Pro Gln Asn Leu Ile Lys Gln Asn Cys
                405             410             415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
            435             440             445

Glu Val Ser Arg Asn Leu Gly Lys Val Gly Ser Lys Cys Cys Lys His
```

```
      450              455              460

Pro Glu Ala Lys Arg Met Pro Cys Ala Glu Asp Tyr Leu Ser Val Val
465              470              475              480

Leu Asn Gln Leu Cys Val Leu His Glu Lys Thr Pro Val Ser Asp Arg
              485              490              495

Val Thr Lys Cys Cys Thr Glu Ser Leu Val Asn Arg Arg Pro Cys Phe
              500              505              510

Ser Ala Leu Glu Val Asp Glu Thr Tyr Val Pro Lys Glu Phe Asn Ala
              515              520              525

Glu Thr Phe Thr Phe His Ala Asp Ile Cys Thr Leu Ser Glu Lys Glu
              530              535              540

Arg Gln Ile Lys Lys Gln Thr Ala Leu Val Glu Leu Val Lys His Lys
545              550              555              560

Pro Lys Ala Thr Lys Glu Gln Leu Lys Ala Val Met Asp Asp Phe Ala
              565              570              575

Ala Phe Val Glu Lys Cys Cys Lys Ala Asp Asp Lys Glu Thr Cys Phe
              580              585              590

Ala Glu Glu Gly Lys Lys Leu Val Ala Ala Ser Gln Ala Ala Leu Gly
              595              600              605

Leu Gly Gly Ser Gly Gly Gly Ser Gly Gly Ala Pro Thr Ser Ser
              610              615              620

Ser Thr Lys Lys Thr Gln Leu Gln Leu Glu His Leu Leu Leu Asp Leu
625              630              635              640

Gln Met Ile Leu Asn Gly Ile Asn Asn Tyr Lys Asn Pro Lys Leu Thr
              645              650              655

Arg Met Leu Thr Phe Glu Phe Tyr Met Pro Lys Lys Ala Thr Glu Leu
              660              665              670

Lys His Leu Gln Cys Leu Glu Lys Glu Leu Lys Pro Leu Glu Glu Val
              675              680              685

Leu Asn Leu Ala Gln Ser Lys Asn Phe His Phe Glu Pro Arg Asp Val
              690              695              700

Val Ser Asn Ile Asn Val Phe Val Leu Glu Leu Lys Gly Ser Glu Thr
705              710              715              720

Thr Phe Met Cys Glu Tyr Ala Asp Glu Thr Ala Thr Ile Val Glu Phe
              725              730              735

Leu Asn Arg Trp Ile Thr Phe Cys Gln Ser Ile Ile Ser Thr Leu Thr
              740              745              750
```

<210> SEQ ID NO 17
<211> LENGTH: 752
<212> TYPE: PRT
<213> ORGANISM: Artificial Sequence
<220> FEATURE:
<223> OTHER INFORMATION: hAlb-hIL2_A4s2

<400> SEQUENCE: 17

```
Met Lys Trp Val Thr Phe Ile Ser Leu Leu Phe Leu Phe Ser Ser Ala
1                5                10               15

Tyr Ser Arg Gly Val Phe Arg Arg Asp Ala His Lys Ser Glu Val Ala
                20               25               30

His Arg Phe Lys Asp Leu Gly Glu Glu Asn Phe Lys Ala Leu Val Leu
              35               40               45

Ile Ala Phe Ala Gln Tyr Leu Gln Gln Cys Pro Phe Glu Asp His Val
              50               55               60

Lys Leu Val Asn Glu Val Thr Glu Phe Ala Lys Thr Cys Val Ala Asp
```

-continued

```
65                   70                   75                   80

Glu Ser Ala Glu Asn Cys Asp Lys Ser Leu His Thr Leu Phe Gly Asp
                85                   90                   95

Lys Leu Cys Thr Val Ala Thr Leu Arg Glu Thr Tyr Gly Glu Met Ala
            100                  105                  110

Asp Cys Cys Ala Lys Gln Glu Pro Glu Arg Asn Glu Cys Phe Leu Gln
            115                  120                  125

His Lys Asp Asp Asn Pro Asn Leu Pro Arg Leu Val Arg Pro Glu Val
        130                  135                  140

Asp Val Met Cys Thr Ala Phe His Asp Asn Glu Glu Thr Phe Leu Lys
145                  150                  155                  160

Lys Tyr Leu Tyr Glu Ile Ala Arg Arg His Pro Tyr Phe Tyr Ala Pro
                165                  170                  175

Glu Leu Leu Phe Phe Ala Lys Arg Tyr Lys Ala Ala Phe Thr Glu Cys
            180                  185                  190

Cys Gln Ala Ala Asp Lys Ala Ala Cys Leu Leu Pro Lys Leu Asp Glu
            195                  200                  205

Leu Arg Asp Glu Gly Lys Ala Ser Ser Ala Lys Gln Arg Leu Lys Cys
        210                  215                  220

Ala Ser Leu Gln Lys Phe Gly Glu Arg Ala Phe Lys Ala Trp Ala Val
225                  230                  235                  240

Ala Arg Leu Ser Gln Arg Phe Pro Lys Ala Glu Phe Ala Glu Val Ser
                245                  250                  255

Lys Leu Val Thr Asp Leu Thr Lys Val His Thr Glu Cys Cys His Gly
                260                  265                  270

Asp Leu Leu Glu Cys Ala Asp Asp Arg Ala Asp Leu Ala Lys Tyr Ile
            275                  280                  285

Cys Glu Asn Gln Asp Ser Ile Ser Ser Lys Leu Lys Glu Cys Cys Glu
        290                  295                  300

Lys Pro Leu Leu Glu Lys Ser His Cys Ile Ala Glu Val Glu Asn Asp
305                  310                  315                  320

Glu Met Pro Ala Asp Leu Pro Ser Leu Ala Ala Asp Phe Val Glu Ser
                325                  330                  335

Lys Asp Val Cys Lys Asn Tyr Ala Glu Ala Lys Asp Val Phe Leu Gly
            340                  345                  350

Met Phe Leu Tyr Glu Tyr Ala Arg Arg His Pro Asp Tyr Ser Val Val
            355                  360                  365

Leu Leu Leu Arg Leu Ala Lys Thr Tyr Glu Thr Thr Leu Glu Lys Cys
        370                  375                  380

Cys Ala Ala Ala Asp Pro His Glu Cys Tyr Ala Lys Val Phe Asp Glu
385                  390                  395                  400

Phe Lys Pro Leu Val Glu Glu Pro Gln Asn Leu Ile Lys Gln Asn Cys
                405                  410                  415

Glu Leu Phe Glu Gln Leu Gly Glu Tyr Lys Phe Gln Asn Ala Leu Leu
            420                  425                  430

Val Arg Tyr Thr Lys Lys Val Pro Gln Val Ser Thr Pro Thr Leu Val
            435                  440                  445

Glu Val Ser Arg Asn Leu Gly Lys Val Gly Ser Lys Cys Cys Lys His
        450                  455                  460

Pro Glu Ala Lys Arg Met Pro Cys Ala Glu Asp Tyr Leu Ser Val Val
465                  470                  475                  480

Leu Asn Gln Leu Cys Val Leu His Glu Lys Thr Pro Val Ser Asp Arg
                485                  490                  495
```

-continued

```
Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Gly Gly Ser Gly Gly Gly Gly Ser Gly Gly Ala Pro Thr Ser Ser
            610                 615                 620

Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Lys Leu Thr
                645                 650                 655

Arg Met Leu Thr Phe Glu Phe Tyr Met Pro Lys Lys Ala Thr Glu Leu
                660                 665                 670

Lys His Leu Gln Cys Leu Glu Lys Glu Leu Lys Pro Leu Glu Glu Val
            675                 680                 685

Leu Asn Leu Ala Gln Ser Lys Asn Phe His Phe Glu Pro Arg Asp Val
            690                 695                 700

Val Ser Asn Ile Asn Val Trp Val Leu Glu Leu Lys Gly Ser Glu Thr
705                 710                 715                 720

Thr Phe Met Cys Glu Tyr Ala Asp Glu Thr Ala Thr Ile Val Glu Phe
                725                 730                 735

Leu Asn Arg Trp Ile Thr Phe Cys Gln Ser Ile Ile Ser Thr Leu Thr
            740                 745                 750
```

```
<210> SEQ ID NO 18
<211> LENGTH: 752
<212> TYPE: PRT
<213> ORGANISM: Artificial Sequence
<220> FEATURE:
<223> OTHER INFORMATION: hAlb-hIL2_A4s3

<400> SEQUENCE: 18

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110
```

-continued

```
Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
            165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525
```

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Gly Gly Ser Gly Gly Gly Ser Gly Gly Ala Pro Thr Ser Ser
    610                 615                 620

Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Lys Leu Thr
                645                 650                 655

Arg Met Leu Thr Phe Glu Phe Tyr Met Pro Lys Lys Ala Thr Glu Leu
            660                 665                 670

Lys His Leu Gln Cys Leu Glu Lys Glu Leu Lys Pro Leu Glu Glu Val
            675                 680                 685

Leu Asn Leu Ala Gln Ser Lys Asn Phe His Phe Glu Pro Arg Asp Leu
        690                 695                 700

Ile Ser Asn Ile Asn Val Phe Val Leu Glu Leu Lys Gly Ser Glu Thr
705                 710                 715                 720

Thr Phe Met Cys Glu Tyr Ala Asp Glu Thr Ala Thr Ile Val Glu Phe
            725                 730                 735

Leu Asn Arg Trp Ile Thr Phe Cys Gln Ser Ile Ile Ser Thr Leu Thr
            740                 745                 750

<210> SEQ ID NO 19
<211> LENGTH: 752
<212> TYPE: PRT
<213> ORGANISM: Artificial Sequence
<220> FEATURE:
<223> OTHER INFORMATION: hAlb-hIL2_A4s4

<400> SEQUENCE: 19

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

-continued

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
                195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala

-continued

```
            565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
            595             600             605

Leu Gly Gly Ser Gly Gly Gly Ser Gly Gly Ala Pro Thr Ser Ser
            610             615             620

Ser Thr Lys Lys Thr Gln Leu Gln Leu Glu His Leu Leu Leu Asp Leu
625             630             635             640

Gln Met Ile Leu Asn Gly Ile Asn Asn Tyr Lys Asn Pro Lys Leu Thr
            645             650             655

Arg Met Leu Thr Phe Glu Phe Tyr Met Pro Lys Lys Ala Thr Glu Leu
            660             665             670

Lys His Leu Gln Cys Leu Glu Lys Glu Leu Lys Pro Leu Glu Glu Val
            675             680             685

Leu Asn Leu Ala Gln Ser Lys Asn Phe His Phe Asp Pro Arg Asp Leu
            690             695             700

Ile Ser Asn Ile Asn Val Phe Val Leu Glu Leu Lys Gly Ser Glu Thr
705             710             715             720

Thr Phe Met Cys Glu Tyr Ala Asp Glu Thr Ala Thr Ile Val Glu Phe
            725             730             735

Leu Asn Arg Trp Ile Thr Phe Cys Gln Ser Ile Ile Ser Thr Leu Thr
            740             745             750
```

<210> SEQ ID NO 20
<211> LENGTH: 752
<212> TYPE: PRT
<213> ORGANISM: Artificial Sequence
<220> FEATURE:
<223> OTHER INFORMATION: hAlb-hIL2_A4s6

<400> SEQUENCE: 20

```
Met Lys Trp Val Thr Phe Ile Ser Leu Leu Phe Leu Phe Ser Ser Ala
1               5               10              15

Tyr Ser Arg Gly Val Phe Arg Arg Asp Ala His Lys Ser Glu Val Ala
            20              25              30

His Arg Phe Lys Asp Leu Gly Glu Glu Asn Phe Lys Ala Leu Val Leu
            35              40              45

Ile Ala Phe Ala Gln Tyr Leu Gln Gln Cys Pro Phe Glu Asp His Val
            50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
            85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
            115             120             125

His Lys Asp Asp Asn Pro Asn Leu Pro Arg Leu Val Arg Pro Glu Val
            130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
            165             170             175

Glu Leu Leu Phe Phe Ala Lys Arg Tyr Lys Ala Ala Phe Thr Glu Cys
```

-continued

```
            180               185               190

Cys Gln Ala Ala Asp Lys Ala Ala Cys Leu Leu Pro Lys Leu Asp Glu
        195               200               205

Leu Arg Asp Glu Gly Lys Ala Ser Ser Ala Lys Gln Arg Leu Lys Cys
    210               215               220

Ala Ser Leu Gln Lys Phe Gly Glu Arg Ala Phe Lys Ala Trp Ala Val
225               230               235               240

Ala Arg Leu Ser Gln Arg Phe Pro Lys Ala Glu Phe Ala Glu Val Ser
            245               250               255

Lys Leu Val Thr Asp Leu Thr Lys Val His Thr Glu Cys Cys His Gly
            260               265               270

Asp Leu Leu Glu Cys Ala Asp Asp Arg Ala Asp Leu Ala Lys Tyr Ile
        275               280               285

Cys Glu Asn Gln Asp Ser Ile Ser Ser Lys Leu Lys Glu Cys Cys Glu
        290               295               300

Lys Pro Leu Leu Glu Lys Ser His Cys Ile Ala Glu Val Glu Asn Asp
305               310               315               320

Glu Met Pro Ala Asp Leu Pro Ser Leu Ala Ala Asp Phe Val Glu Ser
            325               330               335

Lys Asp Val Cys Lys Asn Tyr Ala Glu Ala Lys Asp Val Phe Leu Gly
            340               345               350

Met Phe Leu Tyr Glu Tyr Ala Arg Arg His Pro Asp Tyr Ser Val Val
        355               360               365

Leu Leu Leu Arg Leu Ala Lys Thr Tyr Glu Thr Thr Leu Glu Lys Cys
        370               375               380

Cys Ala Ala Ala Asp Pro His Glu Cys Tyr Ala Lys Val Phe Asp Glu
385               390               395               400

Phe Lys Pro Leu Val Glu Glu Pro Gln Asn Leu Ile Lys Gln Asn Cys
            405               410               415

Glu Leu Phe Glu Gln Leu Gly Glu Tyr Lys Phe Gln Asn Ala Leu Leu
            420               425               430

Val Arg Tyr Thr Lys Lys Val Pro Gln Val Ser Thr Pro Thr Leu Val
            435               440               445

Glu Val Ser Arg Asn Leu Gly Lys Val Gly Ser Lys Cys Cys Lys His
    450               455               460

Pro Glu Ala Lys Arg Met Pro Cys Ala Glu Asp Tyr Leu Ser Val Val
465               470               475               480

Leu Asn Gln Leu Cys Val Leu His Glu Lys Thr Pro Val Ser Asp Arg
            485               490               495

Val Thr Lys Cys Cys Thr Glu Ser Leu Val Asn Arg Arg Pro Cys Phe
            500               505               510

Ser Ala Leu Glu Val Asp Glu Thr Tyr Val Pro Lys Glu Phe Asn Ala
        515               520               525

Glu Thr Phe Thr Phe His Ala Asp Ile Cys Thr Leu Ser Glu Lys Glu
        530               535               540

Arg Gln Ile Lys Lys Gln Thr Ala Leu Val Glu Leu Val Lys His Lys
545               550               555               560

Pro Lys Ala Thr Lys Glu Gln Leu Lys Ala Val Met Asp Asp Phe Ala
            565               570               575

Ala Phe Val Glu Lys Cys Cys Lys Ala Asp Asp Lys Glu Thr Cys Phe
            580               585               590

Ala Glu Glu Gly Lys Lys Leu Val Ala Ala Ser Gln Ala Ala Leu Gly
            595               600               605
```

```
Leu Gly Gly Ser Gly Gly Gly Ser Gly Gly Ala Pro Thr Ser Ser
    610             615             620

Ser Thr Lys Lys Thr Gln Leu Gln Leu Glu His Leu Leu Leu Asp Leu
625             630             635             640

Gln Met Ile Leu Asn Gly Ile Asn Asn Tyr Lys Asn Pro Lys Leu Thr
            645             650             655

Arg Met Leu Thr Phe Glu Phe Tyr Met Pro Lys Lys Ala Thr Glu Leu
            660             665             670

Lys His Leu Gln Cys Leu Glu Lys Glu Leu Lys Pro Leu Glu Glu Val
        675             680             685

Leu Asn Leu Ala His Ser Lys Asn Phe His Phe Glu Pro Arg Asp Leu
    690             695             700

Ile Ser Asn Ile Asn Val Phe Val Leu Glu Leu Lys Gly Ser Glu Thr
705             710             715             720

Thr Phe Met Cys Glu Tyr Ala Asp Glu Thr Ala Thr Ile Val Glu Phe
            725             730             735

Leu Asn Arg Trp Ile Thr Phe Cys Gln Ser Ile Ile Ser Thr Leu Thr
            740             745             750

<210> SEQ ID NO 21
<211> LENGTH: 752
<212> TYPE: PRT
<213> ORGANISM: Artificial Sequence
<220> FEATURE:
<223> OTHER INFORMATION: hAlb-hIL2_A4s7

<400> SEQUENCE: 21

Met Lys Trp Val Thr Phe Ile Ser Leu Leu Phe Leu Phe Ser Ser Ala
1               5               10              15

Tyr Ser Arg Gly Val Phe Arg Arg Asp Ala His Lys Ser Glu Val Ala
            20              25              30

His Arg Phe Lys Asp Leu Gly Glu Glu Asn Phe Lys Ala Leu Val Leu
        35              40              45

Ile Ala Phe Ala Gln Tyr Leu Gln Gln Cys Pro Phe Glu Asp His Val
    50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
            85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
        115             120             125

His Lys Asp Asp Asn Pro Asn Leu Pro Arg Leu Val Arg Pro Glu Val
        130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
            165             170             175

Glu Leu Leu Phe Phe Ala Lys Arg Tyr Lys Ala Ala Phe Thr Glu Cys
            180             185             190

Cys Gln Ala Ala Asp Lys Ala Ala Cys Leu Leu Pro Lys Leu Asp Glu
        195             200             205

Leu Arg Asp Glu Gly Lys Ala Ser Ser Ala Lys Gln Arg Leu Lys Cys
    210             215             220
```

-continued

```
Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu Gly Gly Ser Gly Gly Gly Ser Gly Gly Ala Pro Thr Ser Ser
        610                 615                 620

Ser Thr Lys Lys Thr Gln Leu Gln Leu Glu His Leu Leu Leu Asp Leu
625                 630                 635                 640
```

-continued

```
Gln Met Ile Leu Asn Gly Ile Asn Asn Tyr Lys Asn Pro Lys Leu Thr
            645             650             655

Arg Met Leu Thr Phe Glu Phe Tyr Met Pro Lys Lys Ala Thr Glu Leu
            660             665             670

Lys His Leu Gln Cys Leu Glu Lys Glu Leu Lys Pro Leu Glu Glu Val
        675             680             685

Leu Asn Leu Ala His Ser Lys Asn Phe His Phe Glu Pro Arg Asp Leu
    690             695             700

Ile Ser Asn Ile Asn Val Trp Val Leu Glu Leu Lys Gly Ser Glu Thr
705             710             715             720

Thr Phe Met Cys Glu Tyr Ala Asp Glu Thr Ala Thr Ile Val Glu Phe
            725             730             735

Leu Asn Arg Trp Ile Thr Phe Cys Gln Ser Ile Ile Ser Thr Leu Thr
            740             745             750

<210> SEQ ID NO 22
<211> LENGTH: 752
<212> TYPE: PRT
<213> ORGANISM: Artificial Sequence
<220> FEATURE:
<223> OTHER INFORMATION: hAlb-hIL2_A4s8

<400> SEQUENCE: 22

Met Lys Trp Val Thr Phe Ile Ser Leu Leu Phe Leu Phe Ser Ser Ala
1               5               10              15

Tyr Ser Arg Gly Val Phe Arg Arg Asp Ala His Lys Ser Glu Val Ala
            20              25              30

His Arg Phe Lys Asp Leu Gly Glu Glu Asn Phe Lys Ala Leu Val Leu
        35              40              45

Ile Ala Phe Ala Gln Tyr Leu Gln Gln Cys Pro Phe Glu Asp His Val
    50              55              60

Lys Leu Val Asn Glu Val Thr Glu Phe Ala Lys Thr Cys Val Ala Asp
65              70              75              80

Glu Ser Ala Glu Asn Cys Asp Lys Ser Leu His Thr Leu Phe Gly Asp
            85              90              95

Lys Leu Cys Thr Val Ala Thr Leu Arg Glu Thr Tyr Gly Glu Met Ala
            100             105             110

Asp Cys Cys Ala Lys Gln Glu Pro Glu Arg Asn Glu Cys Phe Leu Gln
        115             120             125

His Lys Asp Asp Asn Pro Asn Leu Pro Arg Leu Val Arg Pro Glu Val
    130             135             140

Asp Val Met Cys Thr Ala Phe His Asp Asn Glu Glu Thr Phe Leu Lys
145             150             155             160

Lys Tyr Leu Tyr Glu Ile Ala Arg Arg His Pro Tyr Phe Tyr Ala Pro
            165             170             175

Glu Leu Leu Phe Phe Ala Lys Arg Tyr Lys Ala Ala Phe Thr Glu Cys
            180             185             190

Cys Gln Ala Ala Asp Lys Ala Ala Cys Leu Leu Pro Lys Leu Asp Glu
        195             200             205

Leu Arg Asp Glu Gly Lys Ala Ser Ser Ala Lys Gln Arg Leu Lys Cys
    210             215             220

Ala Ser Leu Gln Lys Phe Gly Glu Arg Ala Phe Lys Ala Trp Ala Val
225             230             235             240

Ala Arg Leu Ser Gln Arg Phe Pro Lys Ala Glu Phe Ala Glu Val Ser
            245             250             255
```

-continued

```
Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
            370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu Gly Gly Ser Gly Gly Gly Ser Gly Gly Ala Pro Thr Ser Ser
            610                 615                 620

Ser Thr Lys Lys Thr Gln Leu Gln Leu Glu His Leu Leu Leu Asp Leu
625                 630                 635                 640

Gln Met Ile Leu Asn Gly Ile Asn Asn Tyr Lys Asn Pro Lys Leu Thr
                645                 650                 655

Arg Met Leu Thr Phe Glu Phe Tyr Met Pro Lys Lys Ala Thr Glu Leu
            660                 665                 670

Lys His Leu Gln Cys Leu Glu Lys Glu Leu Lys Pro Leu Glu Glu Val
```

US 12,643,930 B2

125                    126

-continued

```
                675                 680                 685

Leu Asn Leu Ala His Ser Lys Asn Phe His Phe Glu Pro Arg Asp Val
    690                 695                 700

Ile Ser Asn Ile Asn Val Phe Val Leu Glu Leu Lys Gly Ser Glu Thr
705                 710                 715                 720

Thr Phe Met Cys Glu Tyr Ala Asp Glu Thr Ala Thr Ile Val Glu Phe
                725                 730                 735

Leu Asn Arg Trp Ile Thr Phe Cys Gln Ser Ile Ile Ser Thr Leu Thr
                740                 745                 750

<210> SEQ ID NO 23
<211> LENGTH: 609
<212> TYPE: PRT
<213> ORGANISM: Homo sapiens

<400> SEQUENCE: 23

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65              70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
    290                 295                 300
```

-continued

```
Lys Pro Leu Leu Glu Lys Ser His Cys Ile Ala Glu Val Glu Asn Asp
305             310             315             320

Glu Met Pro Ala Asp Leu Pro Ser Leu Ala Ala Asp Phe Val Glu Ser
                325             330             335

Lys Asp Val Cys Lys Asn Tyr Ala Glu Ala Lys Asp Val Phe Leu Gly
            340             345             350

Met Phe Leu Tyr Glu Tyr Ala Arg Arg His Pro Asp Tyr Ser Val Val
        355             360             365

Leu Leu Leu Arg Leu Ala Lys Thr Tyr Glu Thr Thr Leu Glu Lys Cys
    370             375             380

Cys Ala Ala Ala Asp Pro His Glu Cys Tyr Ala Lys Val Phe Asp Glu
385             390             395             400

Phe Lys Pro Leu Val Glu Glu Pro Gln Asn Leu Ile Lys Gln Asn Cys
            405             410             415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
        435             440             445

Glu Val Ser Arg Asn Leu Gly Lys Val Gly Ser Lys Cys Cys Lys His
    450             455             460

Pro Glu Ala Lys Arg Met Pro Cys Ala Glu Asp Tyr Leu Ser Val Val
465             470             475             480

Leu Asn Gln Leu Cys Val Leu His Glu Lys Thr Pro Val Ser Asp Arg
            485             490             495

Val Thr Lys Cys Cys Thr Glu Ser Leu Val Asn Arg Arg Pro Cys Phe
            500             505             510

Ser Ala Leu Glu Val Asp Glu Thr Tyr Val Pro Lys Glu Phe Asn Ala
        515             520             525

Glu Thr Phe Thr Phe His Ala Asp Ile Cys Thr Leu Ser Glu Lys Glu
    530             535             540

Arg Gln Ile Lys Lys Gln Thr Ala Leu Val Glu Leu Val Lys His Lys
545             550             555             560

Pro Lys Ala Thr Lys Glu Gln Leu Lys Ala Val Met Asp Asp Phe Ala
            565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
        595             600             605

Leu
```